(12) United States Patent
Salter et al.

(10) Patent No.: US 10,589,051 B2
(45) Date of Patent: Mar. 17, 2020

(54) CPAP COMPLIANCE NOTIFICATION APPARATUS AND METHOD

(71) Applicants: Steven Salter, Tacoma, WA (US); Milt Turco, Puyallup, WA (US)

(72) Inventors: Steven Salter, Tacoma, WA (US); Milt Turco, Puyallup, WA (US)

(*) Notice: Subject to any disclaimer, the term of this patent is extended or adjusted under 35 U.S.C. 154(b) by 730 days.

(21) Appl. No.: 15/299,447

(22) Filed: Oct. 20, 2016

(65) Prior Publication Data

US 2017/0348498 A1  Dec. 7, 2017

Related U.S. Application Data

(60) Provisional application No. 62/243,842, filed on Oct. 20, 2015.

(51) Int. Cl.
*A61M 16/00* (2006.01)
*A61M 16/16* (2006.01)
(Continued)

(52) U.S. Cl.
CPC ............ *A61M 16/16* (2013.01); *A61B 5/1115* (2013.01); *A61B 5/4833* (2013.01); *A61M 16/00* (2013.01);
(Continued)

(58) Field of Classification Search
CPC .......... A47C 27/081; A61B 2562/0247; A61B 2562/043; A61B 5/0816; A61B 5/103; A61B 5/11; A61B 5/113; A61B 5/4806; A61B 5/4818; A61B 5/682; A61B 5/6822; A61B 5/6831; A61B 5/6892; A61B 5/7225; A61B 5/725; A61B 5/7257; A61B 5/7264; A61B 5/7278; A61B 5/7282; A61F 5/56; A61G 2203/30; A61G 7/05;
(Continued)

(56) References Cited

U.S. PATENT DOCUMENTS 3,946,285 A   3/1976  Beery
4,172,216 A  10/1979  O'Shea
(Continued)

FOREIGN PATENT DOCUMENTS

DE  102011012449 A1  4/2012
EP      0722747 A2    7/1996
(Continued)

OTHER PUBLICATIONS

Future Shape, SensFloor Matten, SensFloor Mats, Catalog, 2005, 3 pages, publisher Future Shape GmbH, AltaufstraBe 34, 85635 Hohenkirchen-Siegertsbrunn, Germany.

*Primary Examiner* — Samchuan C Yao
*Assistant Examiner* — Margaret M Luarca
(74) *Attorney, Agent, or Firm* — Elizabeth Reilly; Patentpending, PLLC

(57) ABSTRACT

A CPAP compliance notification apparatus for use with a CPAP device having a flow generator, a CPAP hose, and a CPAP mask, the CPAP compliance notification apparatus, including a patient occupancy mat, an air pressure sensor, an air pressure tube, a compliance notification controller unit, a housing, a user interface, a programmable logic controller together with a patient to control parameters of the CPAP compliance notification apparatus in implementing a compliant CPAP treatment to the patient.

24 Claims, 23 Drawing Sheets

(51) Int. Cl.
*A61M 16/06* (2006.01)
*A61B 5/11* (2006.01)
*A61B 5/00* (2006.01)

(52) U.S. Cl.
CPC ..... *A61M 16/06* (2013.01); *A61M 2016/0027* (2013.01); *A61M 2205/13* (2013.01); *A61M 2205/18* (2013.01); *A61M 2205/332* (2013.01); *A61M 2205/3561* (2013.01); *A61M 2205/505* (2013.01); *A61M 2205/52* (2013.01); *A61M 2205/581* (2013.01); *A61M 2205/583* (2013.01); *A61M 2205/8206* (2013.01); *A61M 2205/8262* (2013.01)

(58) Field of Classification Search
CPC .......... A61M 16/0051; A61M 16/0057; A61M 16/08; A61M 16/0816; A61M 16/0825; A61M 16/0875; A61M 16/107; A61M 16/109; A61M 16/16; A61M 16/201; A61M 16/208; A61M 2205/0216; A61M 2205/10; A61M 2205/15; A61M 2205/332; A61M 2205/3375; A61M 2205/42; A61M 2205/502; A61M 2205/52; A61M 2205/583; A61M 2205/59; A61M 2205/75; A61M 2205/82; A61M 2205/8243; A61M 2205/825; A61M 2209/06; A61M 2209/08; A61M 2209/082; A61M 2209/084; A61M 2209/088; A61M 2230/62; A61M 2230/63; A61M 39/08; A61M 16/0066; A61M 16/024; A61M 16/06; A61M 16/0605; A61M 16/0633; A61M 16/0666; A61M 16/0683; F16L 11/12; F16L 11/22; G01D 5/2405

See application file for complete search history.

(56) References Cited

U.S. PATENT DOCUMENTS

| | | | |
|---|---|---|---|
| 4,314,305 A | 2/1982 | Williams et al. | |
| 4,595,016 A | 6/1986 | Fertig | |
| 4,803,471 A | 2/1989 | Rowlan | |
| 5,038,137 A | 8/1991 | Lloyd | |
| 5,052,400 A | 10/1991 | Dietz | |
| 5,199,424 A | 4/1993 | Sullivan | |
| 5,551,419 A | 9/1996 | Froehlich et al. | |
| 5,598,838 A | 2/1997 | Servidio | |
| 6,028,537 A | 2/2000 | Suman et al. | |
| 6,205,801 B1 | 3/2001 | Riglos et al. | |
| 6,240,921 B1 | 6/2001 | Brydon | |
| 6,326,898 B1 | 12/2001 | O'Leyar | |
| 6,349,724 B1 | 2/2002 | Burton | |
| 6,360,741 B2 | 3/2002 | Truschel | |
| 6,488,634 B1 | 12/2002 | Rapoport | |
| 6,546,930 B1 | 4/2003 | Emerson et al. | |
| 6,701,247 B2 | 3/2004 | Lee | |
| 6,895,798 B2 | 5/2005 | Sosnowski | |
| 6,910,481 B2 | 6/2005 | Kimmel et al. | |
| 7,115,097 B2 | 10/2006 | Johnson | |
| 7,225,793 B2 | 6/2007 | Schwulst | |
| 7,331,349 B2 | 2/2008 | Brady et al. | |
| 7,398,115 B2 | 7/2008 | Lynn | |
| 7,734,350 B2 | 6/2010 | Dubnov | |
| 7,793,660 B2 | 9/2010 | Kimmel et al. | |
| 7,913,692 B2 | 3/2011 | Kwok | |
| 8,064,278 B2 | 11/2011 | Yu et al. | |
| 8,287,452 B2 | 10/2012 | Young et al. | |
| 8,322,339 B2 | 12/2012 | Gottlib et al. | |
| 8,607,793 B2 | 12/2013 | Armistead | |
| 8,672,853 B2 | 3/2014 | Young | |
| 8,833,368 B2 | 9/2014 | Rapoport | |
| 8,931,483 B2 | 1/2015 | Alder et al. | |
| 8,944,057 B2 | 2/2015 | Hill et al. | |
| 8,955,513 B1 | 2/2015 | Kayyall | |
| 8,985,109 B2 | 3/2015 | Bateman | |
| 9,016,277 B2 | 4/2015 | Kniewasser | |
| 9,038,900 B2 | 5/2015 | Ganlanti et al. | |
| 9,052,715 B2 | 6/2015 | Kirchner | |
| 9,053,709 B2 | 6/2015 | Chinen | |
| 9,055,599 B2 | 6/2015 | Cheng | |
| 9,055,605 B2 | 6/2015 | Pratone | |
| 2003/0189492 A1 | 10/2003 | Harvie | |
| 2004/0187871 A1 | 9/2004 | Kimmel | |
| 2005/0076906 A1 | 4/2005 | Johnson | |
| 2006/0118112 A1 | 6/2006 | Cattano et al. | |
| 2008/0216835 A1 | 9/2008 | McGinnis | |
| 2008/0251076 A1 | 10/2008 | Goeldi | |
| 2009/0194109 A1 | 8/2009 | Doshi et al. | |
| 2010/0026499 A1 | 2/2010 | Lamb | |
| 2011/0160619 A1 | 6/2011 | Gabara | |
| 2011/0164002 A1 | 7/2011 | Hill et al. | |
| 2011/0172552 A1 | 7/2011 | Rothman | |
| 2011/0275939 A1 | 11/2011 | Walsh et al. | |
| 2011/0295083 A1 | 12/2011 | Doelling et al. | |
| 2012/0053424 A1 | 3/2012 | Kenalty et al. | |
| 2012/0080034 A1 | 4/2012 | Mansour | |
| 2013/0239960 A1* | 9/2013 | Bertinetti | A61M 16/0066 128/202.22 |
| 2013/0284166 A1 | 10/2013 | Colla | |
| 2014/0123977 A1 | 5/2014 | Lalonde | |
| 2014/0144445 A1 | 5/2014 | Bowditch | |
| 2014/0228711 A1 | 8/2014 | Mireshghi | |
| 2014/0283826 A1 | 9/2014 | Murray | |
| 2014/0299132 A1 | 10/2014 | Librett | |
| 2014/0332005 A1 | 11/2014 | Kunz et al. | |
| 2015/0047639 A1 | 2/2015 | Farrugia et al. | |
| 2015/0054317 A1 | 2/2015 | Fortune et al. | |
| 2015/0114390 A1 | 4/2015 | Hill et al. | |
| 2015/0164438 A1* | 6/2015 | Halperin | A61B 5/746 340/573.1 |

FOREIGN PATENT DOCUMENTS

| | | |
|---|---|---|
| EP | 1495779 A2 | 1/2005 |
| EP | 1948276 A1 | 7/2008 |
| JP | 2008200447 A | 9/2008 |
| WO | 2011082346 A2 | 7/2011 |

* cited by examiner

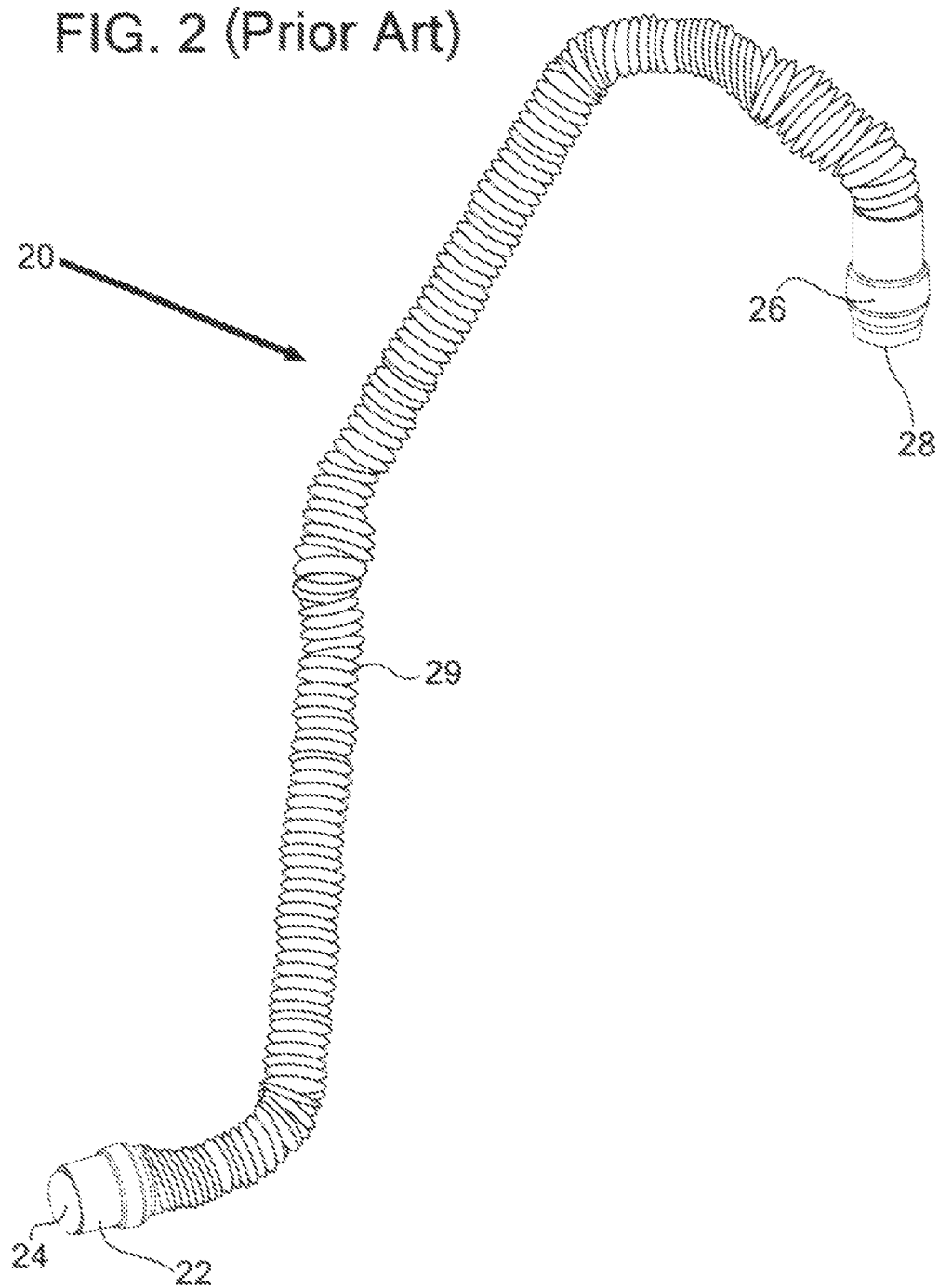

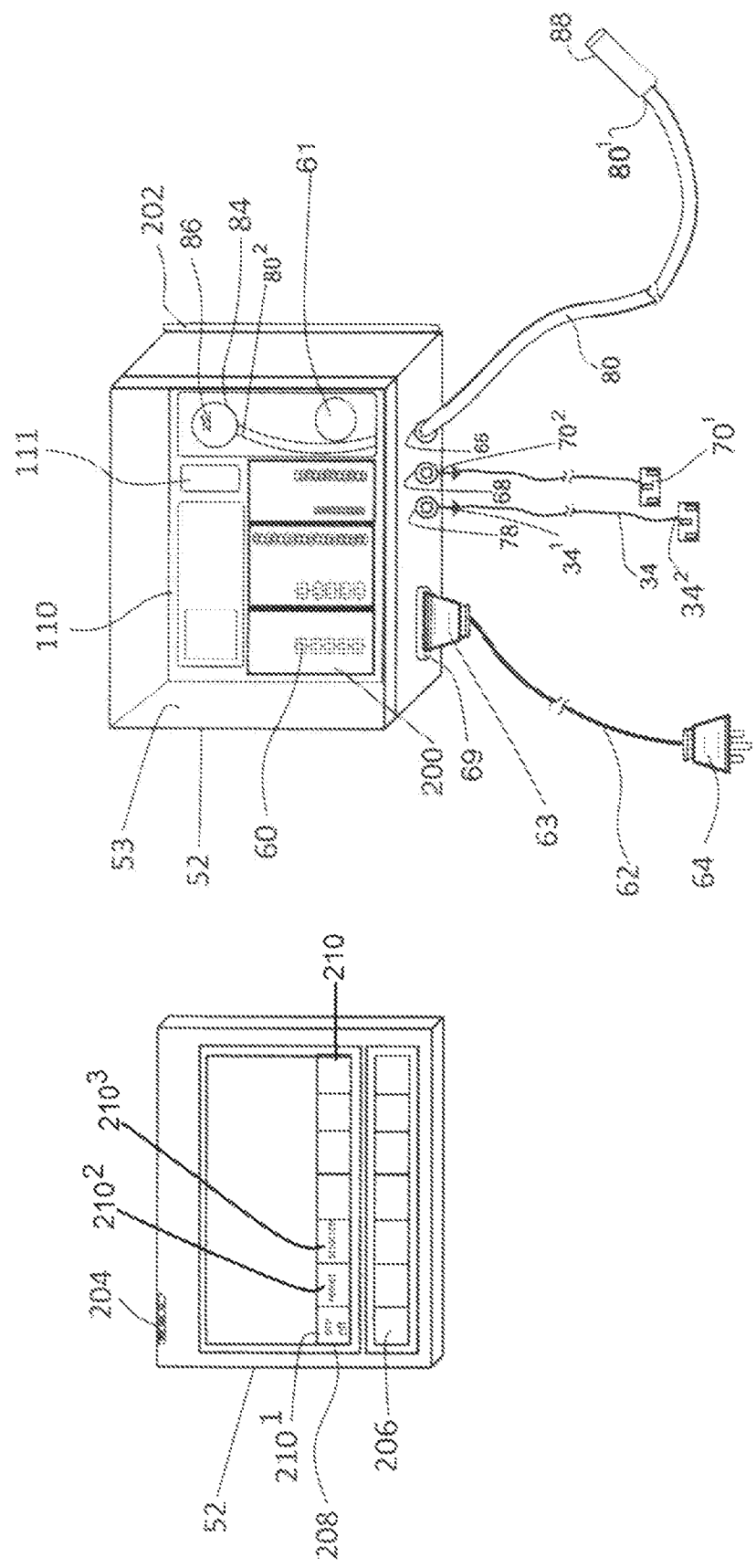

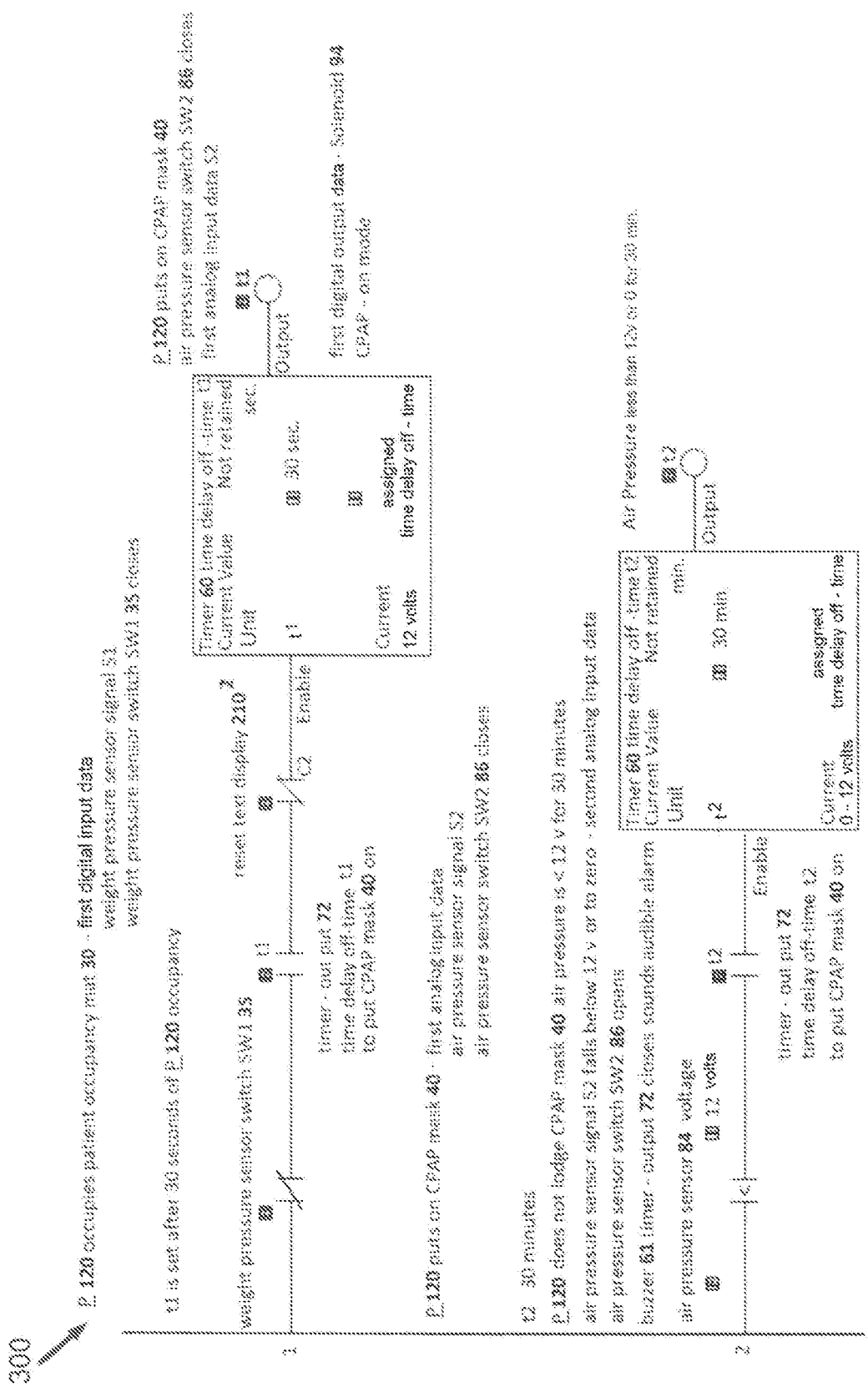

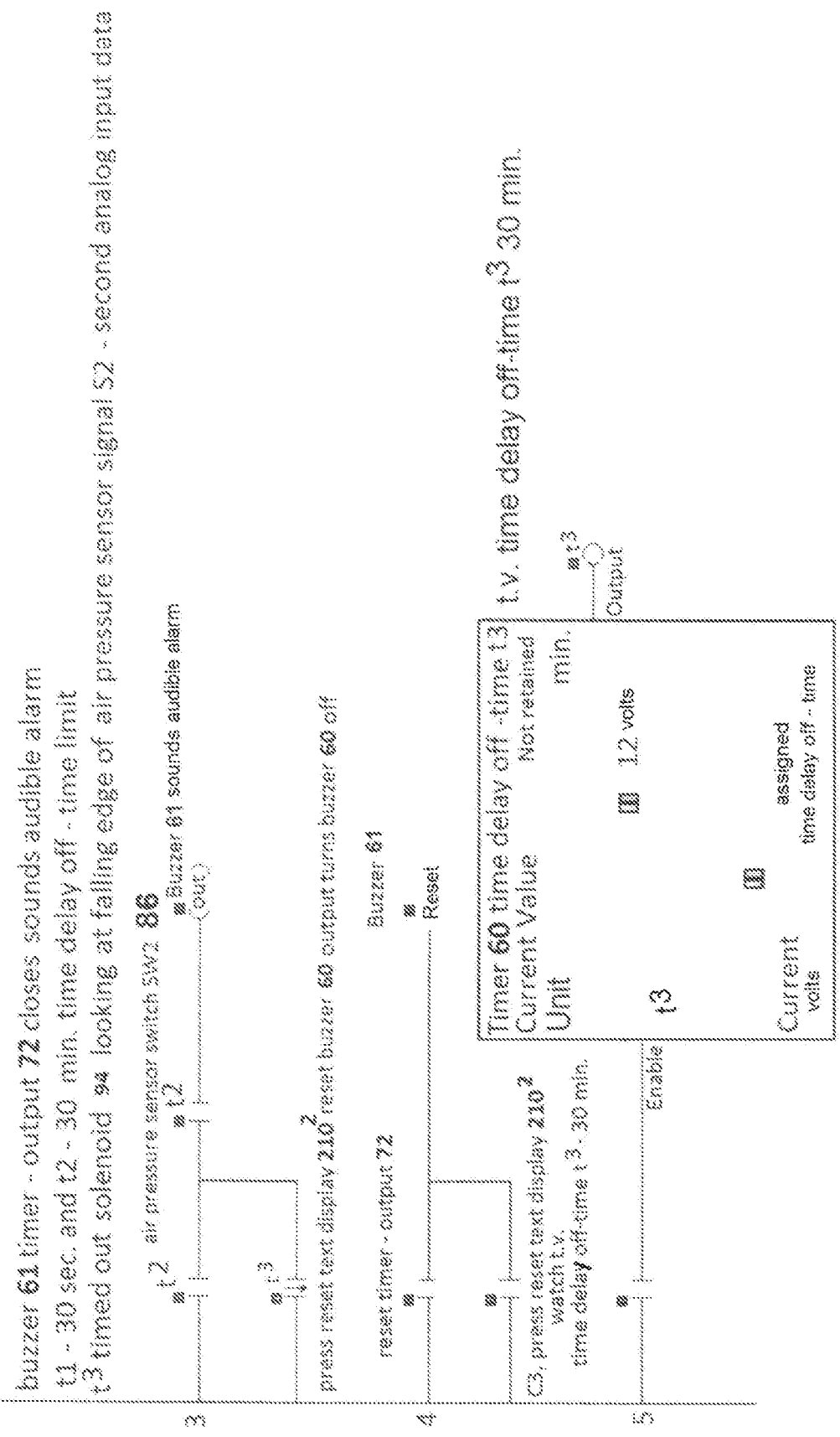

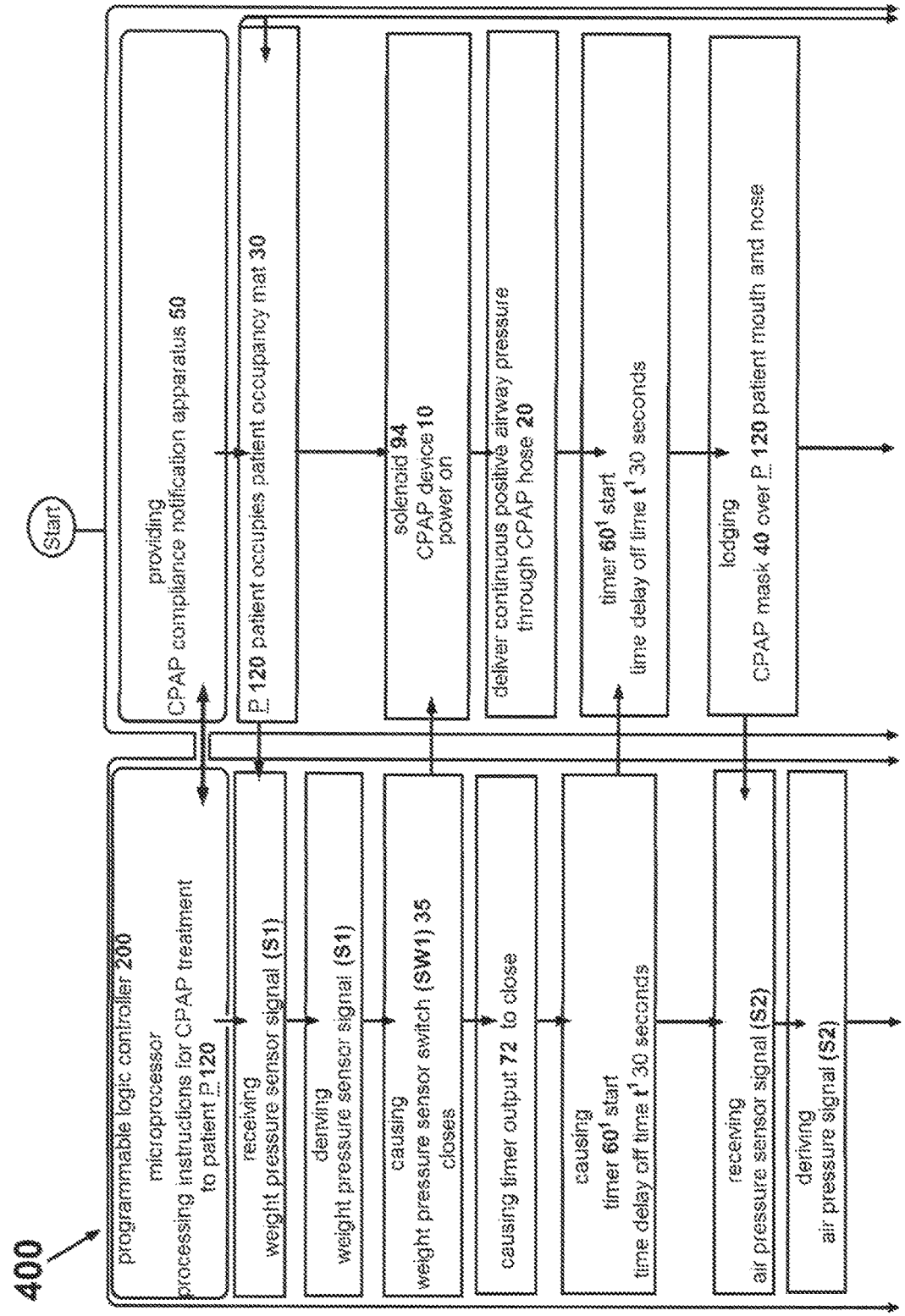

CPAP COMPLIANCE NOTIFICATION APPARATUS AND METHOD

FIELD OF THE INVENTION

An embodiment relates to a compliance notification apparatus and method configured for use with a conventional continuous positive air pressure device ("CPAP device") for alerting a patient to lodge a CPAP mask utilized for treatment of sleep apnea disorders within an assigned delay time.

In particular, an embodiment relates to a compliance notification and method for alerting a patient prior to or during continuous positive air pressure therapy to lodge a continuous positive air pressure mask ("CPAP mask") while detecting the patient's occupancy or vacancy upon a supportive substrate, and in simultaneous consideration detecting changes in air pressure in an air tube remotely positioned from the airways of the patient as indicative of the patient's compliance with use of a CPAP device so that the patient can receive the prescribed continuous positive air pressure therapy for sleep apnea.

BACKGROUND OF THE INVENTION

The need is known in the field of CPAP devices, systems and methods, and in particular, of a CPAP compliance apparatus and method to be able to detect a signal of a patient's instantaneous presence upon a supporting substrate while in simultaneous consideration able to detect a signal of changes in air pressure through an air pressure tube remotely positioned from the airways of the patient so as to employ such signals to a compliance notification controller unit adapted to provide the patient receiving the CPAP treatment an alert at the end limit of a time delay off-time relating to the patient's initial lodging of a mask or re-lodging of the patient's CPAP mask in the event the CPAP mask has become dislodged during CPAP treatment utilized for treatment of sleep apnea with the purpose of delivering of continuous positive airway pressure to the patient so that the patient is compliant with his/her physician's prescribed CPAP treatment.

Apnea is a sleep disorder characterized by abnormal pauses in breathing or instances of abnormally low breathing during sleep. According to Sleep Medical Review, Continuous Positive Airway Pressure (CPAP) therapy is the gold standard treatment for people diagnosed with sleep apneas. CPAP is an acronym for "continuous positive airway pressure", which was developed by Dr. George Gregory and colleagues in the neonatal intensive care unit at the University of California, San Francisco (Gregory G A; Kitterman J A; Phibbs R H; Tooley W H; Hamilton W K (Jun. 17, 1971). "Treatment of the idiopathic respiratory-distress syndrome with continuous positive airway pressure. *The New England Journal of Medicine* 284 (24): 1333-40. ISSN 0028-4793. LCCN 20020456. OCLC 231027780. PMID 4930602. Retrieved 2015-03-22).

Sleep Apnea is a breathing disorder that occurs during periods of sleep. The Greek word "apnea" means "without breath". It is intermittent cessation of ventilation during sleep that results in a decrease in blood oxygen levels, a decrease in heart rate, and resultant illnesses such as cardiac arrhythmias, hypertension, heart disease, and/or heart failure. The consequences of sleep apnea are evident throughout the waking hours, and include sleepiness, non-attentiveness, headaches, memory problems, weight gain, safety-related accidents, personality disturbances, and other sleep-deprivation related afflictions. The causes of the various forms of sleep apnea are not fully understood. There are three general types of sleep apnea or Sleep Disordered Breathing (SDB): Obstructive Sleep Apnea (OSA), Central Sleep Apnea (CSA) and Mixed Sleep Apnea.

Obstructive sleep apnea results from a blockage or occlusion of the oropharyngeal (upper) airway. With obstructive sleep apnea, respiratory functions continue, but blockage or occlusion of the airway results in reduced or halted airflow. Obstructive sleep apnea syndrome is indicated by a narrowing of the upper airway, resulting in a progressive asphyxia that continues until the individual is briefly woken from sleep, which restores airway patency and airflow through the upper airway. These frequent arousals, although necessary for proper airway ventilation to resume, deprive the individual from restorative deep sleep. These partial awakenings throughout sleep result in both mental and physical strain on the individual. Obstructive sleep apnea is the most common form of sleep apnea.

Central sleep apnea results from the brain failing to signal the muscles to breathe. The neural drive to the respiratory muscles discontinues for a brief period of time. These transients may continue throughout the night for periods from ten seconds to as long as 2 to 3 minutes. Often time individuals with central sleep apnea have a history of pulmonary hypertension, heart disease or heart failure, respiratory problems, or polycythemia. Central sleep apnea, similar to obstructive sleep apnea, causes a gradual asphyxiation during sleep, resulting is a brief arousal from sleep, at which time the individual's respiratory function returns to normal. consequences of central sleep apnea during the waking hours is similar to those of obstructive sleep apnea, and include sleepiness, non-attentiveness, headaches, memory problems, weight gain, safety-related accidents, personality disturbances, and other sleep-deprivation related afflictions.

In sum, the sleeper who suffers from OSA periodically struggles to breathe but is unable to inhale effectively because his or her airway has collapsed. The sleeper whose problem is CSA periodically doesn't breathe at all, or breathes so shallowly that oxygen intake is ineffectual. In either type of sleep apnea, the lack of oxygen usually causes the patient to wake up, at least briefly.

There are several known treatments for sleep apnea. They consist of physical or mechanical treatments, surgery, and attempts at pharmacological treatment. The treatment regimen is tailored to the individual, and is based on the medical profile of the patient being treated.

The most common effective treatment for patients with sleep apnea is continuous positive airway pressure (CPAP). The purpose of the CPAP device is to provide a positive pressure on the nasopharynx and the oropharynx to keep the airways open therein allowing the user to continue to breathe. In this form of treatment, the patient wears a face mask over the mouth and nose while sleeping. The CPAP mask is connected to a CPAP hose that is connected to a flow generator of the CPAP device. The flow generator provides a continuous positive air flow to an airway of the patient, for example, nasal airway, mouth airway, at an elevated air pressure to treat the sleep apnea disorder. The CPAP mask communicates the CPAP hose with the airway of the patient. Examples of patient masks include, a nasal mask, nasal and oral mask, full face mask, nasal cannula, oral mouthpiece, tracheal tube, endotracheal tube, or hood.

The flow generator creates a continuous positive air flow of breathing gas having a pressure greater than the ambient atmospheric pressure. The continuous positive airway pressure system prevents the airway from closing or becoming obstructed during sleep. The CPAP device is adapted to use a continuous positive air pressure to the airway of the patient to treat sleep apnea disorders. The CPAP device, also, provides a positive pressure therapy in which the pressure of air delivered to the patient varies with the patient's breathing cycles or varies with the patient's effort to increase the comfort to the patient.

The air pressure from the continuous positive airway system is constant, and can be adjusted to best suit the individual's apnea condition. The air pressure in the continuous positive airway pressure system must be adjusted so that it maintains an open airway in the patient during all periods of sleep, but does not provide excessive pressure such that the device is bothersome to the patient.

Obstructive sleep apnea occurs when the upper airway becomes narrow as the muscles relax naturally during sleep. As noted above, this reduces oxygen in the blood and causes arousal from sleep. The CPAP device stops this phenomenon by delivering a stream of compressed air via a hose to a nasal pillow, nose mask, full-face mask, or hybrid, splinting the airway (keeping it open under air pressure) so that unobstructed breathing becomes possible, therefore reducing and/or preventing apneas and hyponeas. It is important to understand, however, that it is the air pressure, and not the movement of the air, that prevents the apneas. When the device is turned on, but prior to the mask being placed on the head, a flow of air comes through the mask. After the mask is placed on the head, it is sealed to the face over the patient's nose and or nose and mouth and the air stops flowing. At this point, it is only the air pressure that accomplishes the desired result. This has the additional benefit of reducing or eliminating the extremely loud snoring that sometimes accompanies sleep apnea.

The CPAP device through a flow generator blows air at a prescribed pressure (also called the titrated pressure). The necessary pressure is usually determined by a sleep physician after review of a study supervised by a sleep technician during an overnight study (polysomnography) in a sleep laboratory. The titrated pressure is the pressure of air at which most (if not all) apneas and hypopneas have been prevented, and it is usually measured in centimeters of water ($cmH_2O$). The pressure required by most patients with sleep apnea ranges between 6 and 14 $cmH_2O$. A typical CPAP device can deliver pressures between 4 and 20 $cmH_2O$. More specialized units can deliver pressures up to 25 or 30 $cmH_2O$. Other CPAP devices can titrate a range of continuous positive air pressure automatically based upon input entered into the CPAP device by the patient through a setting dial on the CPAP flow generator unit.

CPAP treatment can be highly effective in treatment of sleep apnea disorders. For some patients, the improvement in the quality of sleep and quality of life due to CPAP treatment will be noticed after a single night's use. Often, the patient's sleep partner also benefits from markedly improved sleep quality, due to the amelioration of the patient's loud snoring. Given that sleep apnea is a chronic health issue which commonly doesn't go away, ongoing care is usually needed to maintain CPAP therapy.

Continuous positive airway pressure systems remain the most effective treatment for sleep apnea. A concern with the CPAP device is that many patients, however, fail to use the CPAP device for treatment because they fall asleep before lodging the CPAP mask. Another concern is that an air pressure sensor is located at the CPAP hose or at the CPAP mask and can become completely blocked or partially blocked by a buildup of secretion from the patient in an exhaust port in the mask. Blockage can, also, occur as a result of the patient's bedding, covering the air pressure sensor. Therefore, for example, a patient using the CPAP device during a sleep cycle at night to treat sleep apnea can be interrupted. This leaves many sleep apnea patients without an effective treatment regimen.

Patient compliance with CPAP therapy is a significant issue. At the forefront of non-compliant issues is the condition of patients at bedtime. Many patients are usually fatigued and exhausted from lack of sleep and will usually fall asleep before turning the CPAP device on; or fall asleep before lodging the mask on his/her face to receive the necessary CPAP therapy.

Amongst the other issues, is the factor that the mask becomes dislodged during the user's sleep and, consequently, the user does not receive the necessary CPAP therapy. Many patients have difficulty tolerating the mask fitted to, the patient's face during an entire night of treatment for sleep apnea. Typically, the patient will experience a sleep arousal period or will partially awaken to move about during the night, and will return to sleep without reapplying the dislodged mask. Frequently, the mask will be remain partially or fully removed by the patient's movement during the night. The effectiveness of the CPAP treatment for sleep apnea is significantly disrupted after the mask is partially or fully dislodged during sleep or during a brief waking event. Data logging records, basic compliance information or detailed event logging, allowing the sleep physician (or patient) to download and analyses data recorded by the device to verify treatment effectiveness.

If the patient is not able to use the CPAP device properly for failure to lodge the mask or continued dislodgement of the mask during the sleep cycle, the patient will continue to suffer from sleep apnea disorders, not be able to receive relief and at risk of related physiological complications. In addition, the CPAP devices typically detect excessive mask disruptions, leaks due to mouth breathing in order to provide an electronic log of the total time the CPAP device is used by the patient, whether the patient was breathing normal, whether apnea events occurred, and whether open mouth breathing occurs during the sleep cycle. If the electronic log reveals non-compliance by the patient, it is possible that the patient's diagnosis of OSA, or CSA becomes questionable, which may result in loss of the prescribed CPAP device from the physician, or an insurance company's coverage of costs related to home treatment of the CPAP device.

Hence, a CPAP compliance notification apparatus and method is necessitated as a solution to the problems associated with the CPAP device and more importantly for implementation while the patient is awake or asleep.

Hence, to further maximize the effectiveness of sleep apnea treatment utilizing CPAP the CPAP compliance notification apparatus and method is needed to promote compliant use of the CPAP device and, therefore, to maximize CPAP treatment of apnea while the patient is awake prior to CPAP treatment or through a sleep cycle during CPAP treatment. It is embodied that a mat weight pressure sensor senses the presence of the patient recumbent or sitting in bed and starts the timer counting down to a pre-assigned delay-time off time and sounds the auditory buzzer which alerts the patient in the situation when the mask has not been initially lodged on his/her nose or mouth at the inception of sleep within the pre-assigned time limit.

The patient is alerted by an auditory alarm which reminds the non-sleeping patient, or wakens the sleeping patient to lodge the mask to start the CPAP treatment if in fact the patient has failed to lodge the mask within the preferred pre-set time limit. In addition, it is preferred that a pre-set timer with the buzzer provides a preferred timed alert notification to a patient when the mask has dislodged during sleep and, subsequently, when the patient has not reapplied the dislodged mask within the pre-set time limit. It can be beneficial to give the patient a time range to lodge the mask on his/her own before the alarm sounds and not to alert the alarm immediately. The alarm may be loud and wake others. As soon as the patient lodges the mask in the proper position on his/her face or nose the alarm will not be triggered. It can also be beneficial to give the patient a shorter time to lodge his/her mask within a shorter time limit.

A known patient preference is to read before he/she lodges the CPAP, or another known patient preference is to watch t.v. before the patient lodges the CPAP mask. However, one of the interfering factors is the fact that the sleep apnea patient is chronically fatigued because of lack of sleep due to his/her sleep apnea. As a result, the patient, frequently, is in bed, or in a recliner chair, or on an air mattress, or any sleep medium, and turns on the CPAP device with intentions to use the CPAP device for CPAP treatment, after reading or watching t.v. but falls asleep before the patient lodges his/her CPAP mask onto his/her nose or nose and/or mouth. The effectiveness of the CPAP treatment for the sleep apnea patient is obviously diminished if the mask is not initially lodged onto the patient's nose or mouth. If a patient is not alerted to the event of failure to initially lodge the mask then treatment for sleep apnea is, obviously, compromised.

In addition, when the patient is in bed and has successfully lodged his/her CPAP mask and falls asleep, the CPAP mask can become dislodged during the patient's sleep cylce. In this instance, the patient may not wake up to re-lodge his/her CPAP mask and once again the patient is non-compliant and, consequently, the patient does not receive his/her prescribed continuous positive air pressure therapy for his/her sleep apnea.

Accordingly, embodiments of the invention are provided that meet at least one or more of the following objects of the invention.

It is an object of an embodiment of the invention that the patient occupancy mat upon a patient's occupancy of the patient occupancy mat, for example, gets into bed in preparation to receive CPAP therapy, to automatically power the CPAP device to the "on-mode" and in simultaneous communication automatically starting a timer pre-assigned with a delay time within which an buzzer will sound to alert the patient in the event the patient has not lodged his/her CPAP mask, initially, while the patient was awake, or the CPAP mask has become dislodged during the patient's sleep cycle. It is known the patient can fall asleep before the patient turns on the CPAP device or the timer due to fatigue, or the patient simply forgets to turn on the CPAP device and as a result does not receive the necessary CPAP therapy. And, similarly, it is embodied that the mat weight sensor triggers the CPAP device to power to the "off mode" automatically when the patient vacates his/her bed and automatically turns off the timer in case the patient inadvertently forgets to do so.

It is another object of the embodiment of the invention to provide a patient occupancy mat sensor to detect the patient's occupancy in bed, and to provide a buzzer directly to alert the patient upon failure to initially lodge the mask, to alert the patient of mask misalignment, or mask dislodgement to maximize CPAP treatment of apnea through a sleep cycle.

A CPAP device was initially used mainly by patients for the treatment of sleep apnea at home. Today, patients are very transient. Therefore, it is another object of the embodiment of the invention to provide a CPAP compliance notification apparatus and method which includes a portable patient occupancy mat of varied sizes so that patient's occupancy can be detected on a variety of supportive substrate, including any one of bed mattress, wheel chair, bed, or in a recliner chair, or on an air mattress, or any sleep medium, or any seating medium It is another object of an embodiment of the invention to provide a variety of assigned delay times thereby alerting the patient that his/her mask has not been initially lodged or is dislodged as soon as possible after dislodgement in order to have the mask refitted and to maximize CPAP treatment of apnea throughout the sleep cycle, or to alert the patient within a longer delay time that his/her CPAP has not been initially lodged or is dislodged so that the patient has time, for example, to watch t.v., read, or the like, or more time during his/her sleep-cycle before he/she is alerted to initially lodge his/her mask.

It is another object of the present invention to include a remotely positioned air pressure sensor remotely positioned from the air pressure being sensed from the air ways of the patient. The remote position of the air pressure sensor is advantageous because the air pressure sensor will not be dislodged when the patient moves during CPAP treatment and it will not become clogged with patient respiratory exudate from the patient's airways yielding incorrect air pressure signals.

It is another object of the present invention to include a remotely positioned reset button proximate to the patient.

The embodiment of the CPAP compliance notification device and method can be ascertained as mandatory of all CPAP users by physicians and insurance companies.

SUMMARY OF THE INVENTION

In view of the above, the Applicant has tackled the problem with the CPAP compliance notification apparatus for use with a CPAP device having a flow generator, a CPAP hose, and a CPAP mask, the CPAP compliance notification apparatus, including a patient occupancy mat, an air pressure sensor, an air pressure tube, a compliance notification controller unit, a housing, a user interface, a programmable logic controller together with a patient to control parameters of the CPAP compliance notification apparatus in implementing a compliant CPAP treatment to the patient. of improving the automatically and in simultaneous communication the timer begins to count down to the assigned delay time. If the timer output identifies that the patient is occupied on the patient occupancy mat and in simultaneous communication the timer output identifies detection that the CPAP mask is initially lodged and sealed on the patient's nose and/or nose and mouth in simultaneous communication with the timer output the timer is disengaged and stops counting down to the delay time.

If the patient does not lodge his/her CPAP mask within the delay time the buzzer will sound to alert the patient to lodge his/her mask or re-lodge his/her CPAP. The buzzer includes an audible alarm providing an audible alert signal and/or a directed to the patient in sufficient intensity to alert the awake patient to initially lodge his/her CPAP mask or awaken the sleeping patient to re-lodge or adjust his/her CPAP mask, thereby providing an audible alert to the patient to adjust the mask.

If the patient does not reoccupy the patient occupancy mat after vacating the mat within the delay time the buzzer will sound to alert the patient to reoccupy the patient occupancy mat to receive the CPAP treatment. The buzzer includes an audible alarm providing an audible alert signal and/or a directed to the patient in sufficient intensity to alert the patient to return to the patient occupancy mat, especially, in the case where the patient has fallen out of bed.

A system and method of operation of a CPAP compliance notification apparatus for CPAP treatment of a patient having a sleep disorder including sleep apnea is, also, disclosed.

Given that sleep apnea is a chronic health issue which commonly doesn't go away, ongoing compliance by means of the CPAP compliance notification apparatus is needed to maintain CPAP therapy in order for the patient to ameliorate the symptoms of his sleep apnea disorder and in order for the patient to be in compliance with the physicians prescribed CPAP therapy in order for the patient to maintain their health insurance benefits.

Therefore there is a need for a solution to non-compliance by a patient to CPAP treatment due to the patient failing to lodge or re-lodge a dislodged mask so that the patient can receive the prescribed continuous positive airway pressure treatment and accordingly the patient's condition can improve.

BRIEF DESCRIPTION OF THE DRAWINGS

The embodiments of the invention itself, as well as further features and the advantages thereof, will be best understood with reference to the following detailed description, given purely by way of a non-restrictive indication, to be read in conjunction with the accompanying figures. Particularly:

FIG. 2 shows a known conventional continuous positive air pressure hose (CPAP hose), according to an embodiment of the present disclosure.

FIG. 6A shows a top perspective view of the top interior portion of the compliance notification controller unit, according to an embodiment of the present disclosure.

FIG. 6B shows a top perspective view of the interior bottom portion of the compliance notification unit, according to an embodiment of the present disclosure.

FIG. 11A shows a first page of a CPAP compliance notification apparatus, according to an embodiment of the disclosure.

FIG. 11B shows a second page of the CPAP compliance notification apparatus of FIG. 11A, according to an embodiment of the disclosure.

FIG. 12A shows a first page of a schematic illustration of an embodiment of a CPAP compliance notification method implementing a CPAP compliance notification apparatus.

DICTIONARY

Figure 1B:
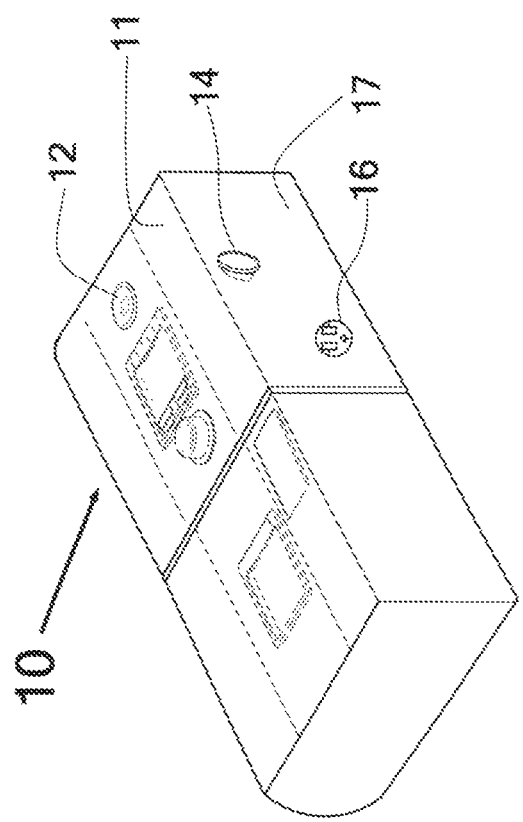
FIG. 1B shows a perspective rear view of the known conventional CPAP device of FIG. 1A.

Fluid—air, gas, water, gel, or combination thereof.
Patient—people, animal, subject, user of the CPAP device.
Positive air pressure—flow of air having a pressure greater than the ambient atmospheric pressure.

DETAILED DESCRIPTION OF THE PREFERRED EMBODIMENTS

In the following, a solution according to exemplary and non-limiting embodiments will be described in detail. Those skilled in the art will, however, recognize that several modifications to the described embodiments are possible. Embodiments of the disclosure may be understood by references to FIGS. 1A through 14 wherein like numbers are used to indicate like and corresponding parts.

As can be seen in FIGS. 1A-14, the CPAP compliance notification apparatus 50, in the embodiment of the disclosure of the subject matter the CPAP compliance notification apparatus 50, comprises a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, and together with a patient P 120, to control parameters of the CPAP compliance notification apparatus 50 in implementing a compliant CPAP treatment to the patient P 120 for use with a CPAP device 10, as shown in FIGS. 1A-3, having a flow generator 18, a flow generator outlet 18$^1$, a CPAP hose 20, and a CPAP mask 40.

The CPAP compliance notification apparatus 50, comprises the patient occupancy mat 30 having a weight pressure sensor 32 including a weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

Figure 10:
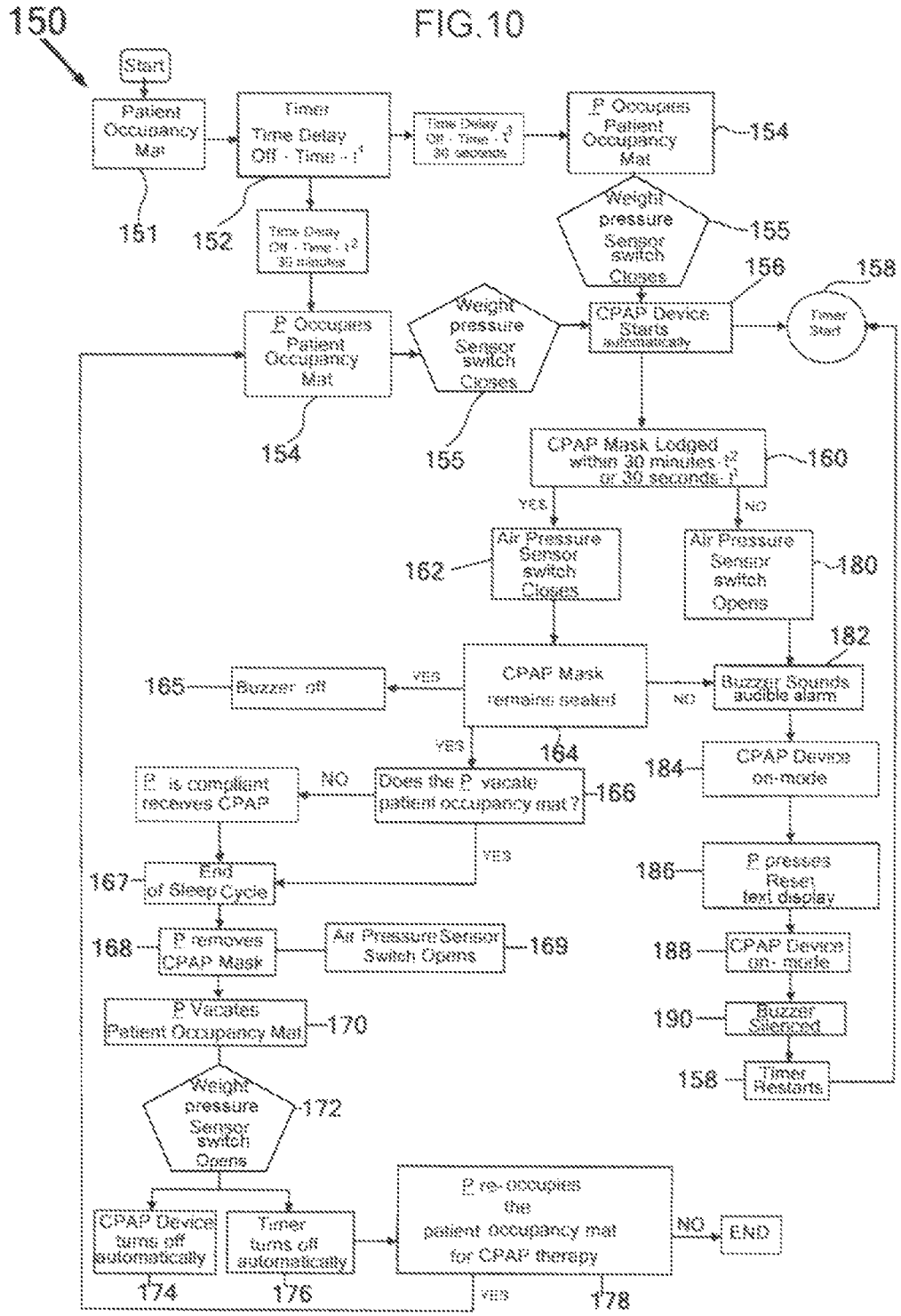
FIG. 10 shows a schematic of a method of the implementation of the CPAP compliance notification apparatus, according to an embodiment of the disclosure.
Figure 11C:
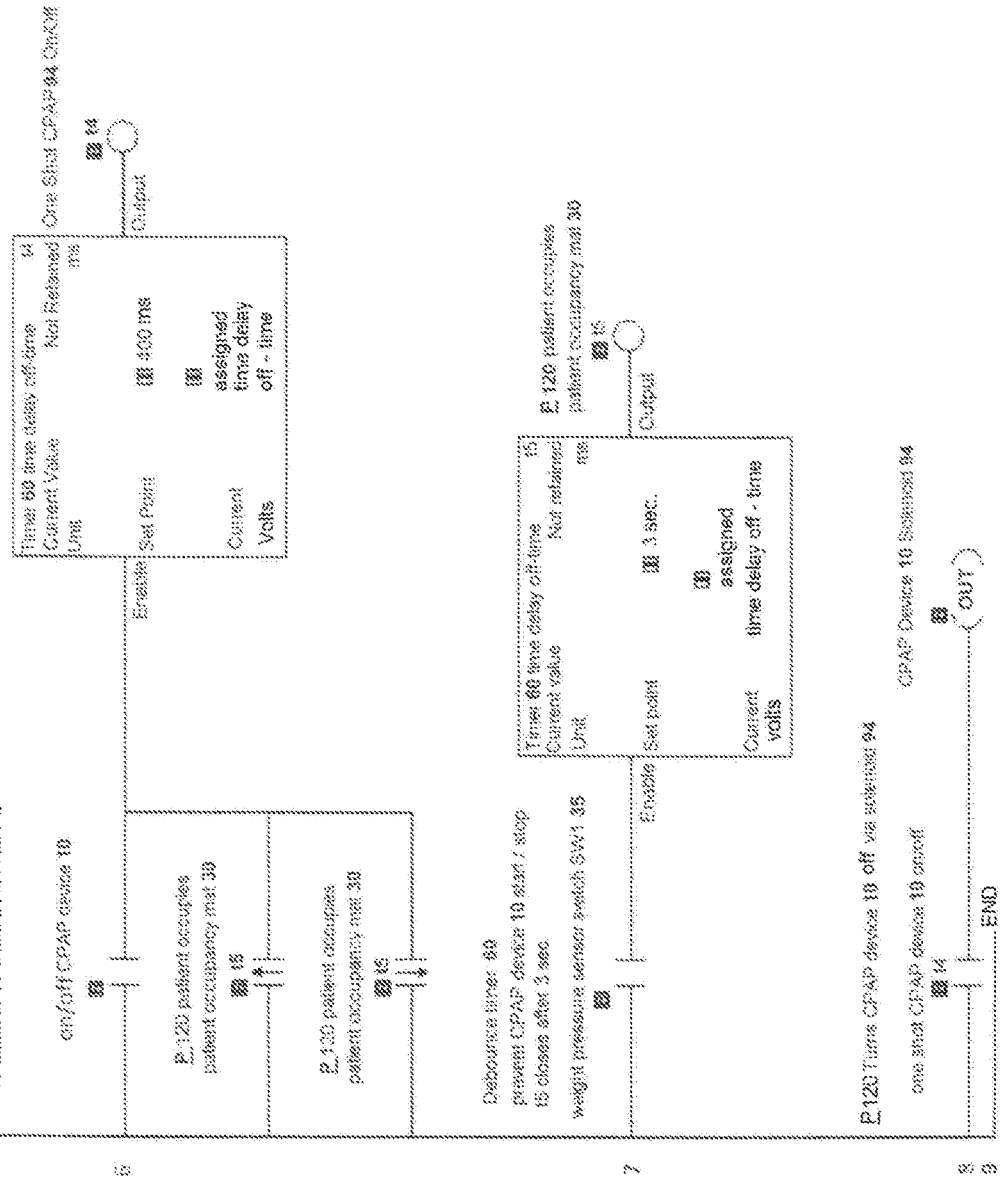
FIG. 11C shows a third page of the CPAP compliance notification apparatus of FIG. 11A, according to an embodiment of the disclosure.
Figure 12B:
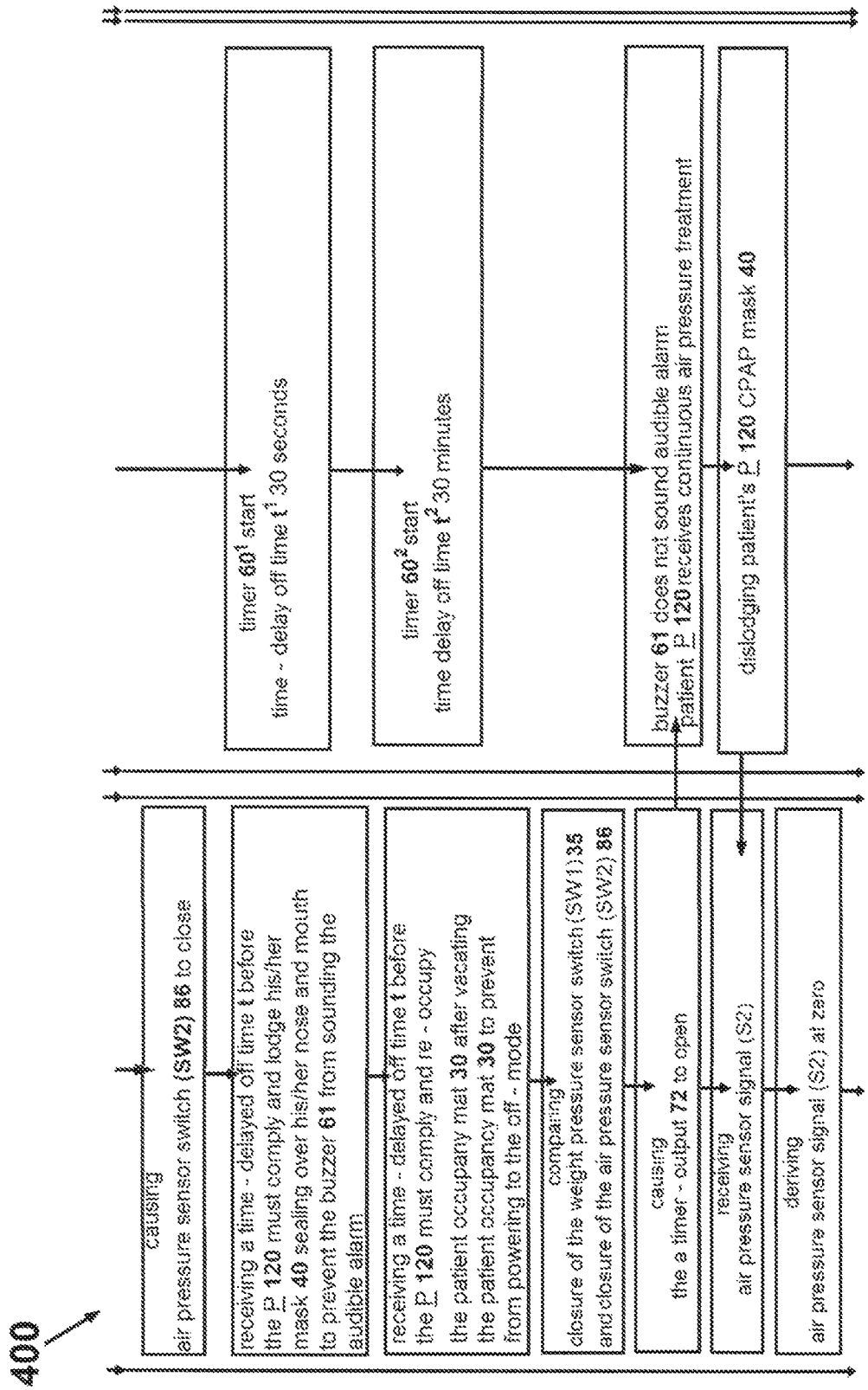
FIG. 12B shows a second page of the schematic illustration of an embodiment of the CPAP compliance notification method of FIG. 12A.
Figure 12C:
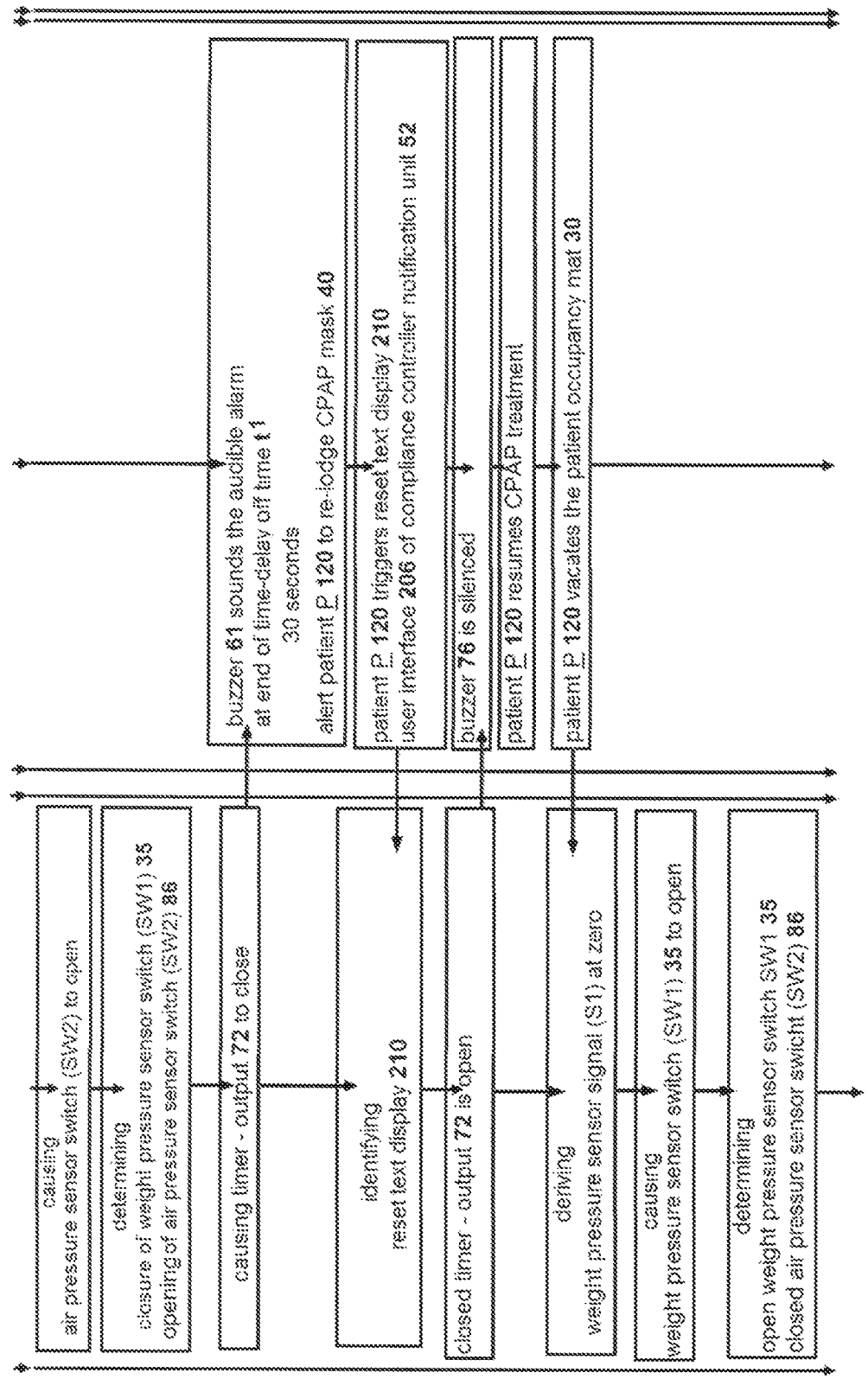
FIG. 12C shows a third page of the schematic illustration of an embodiment of the CPAP compliance notification method of FIG. 12A.
Figure 12D:
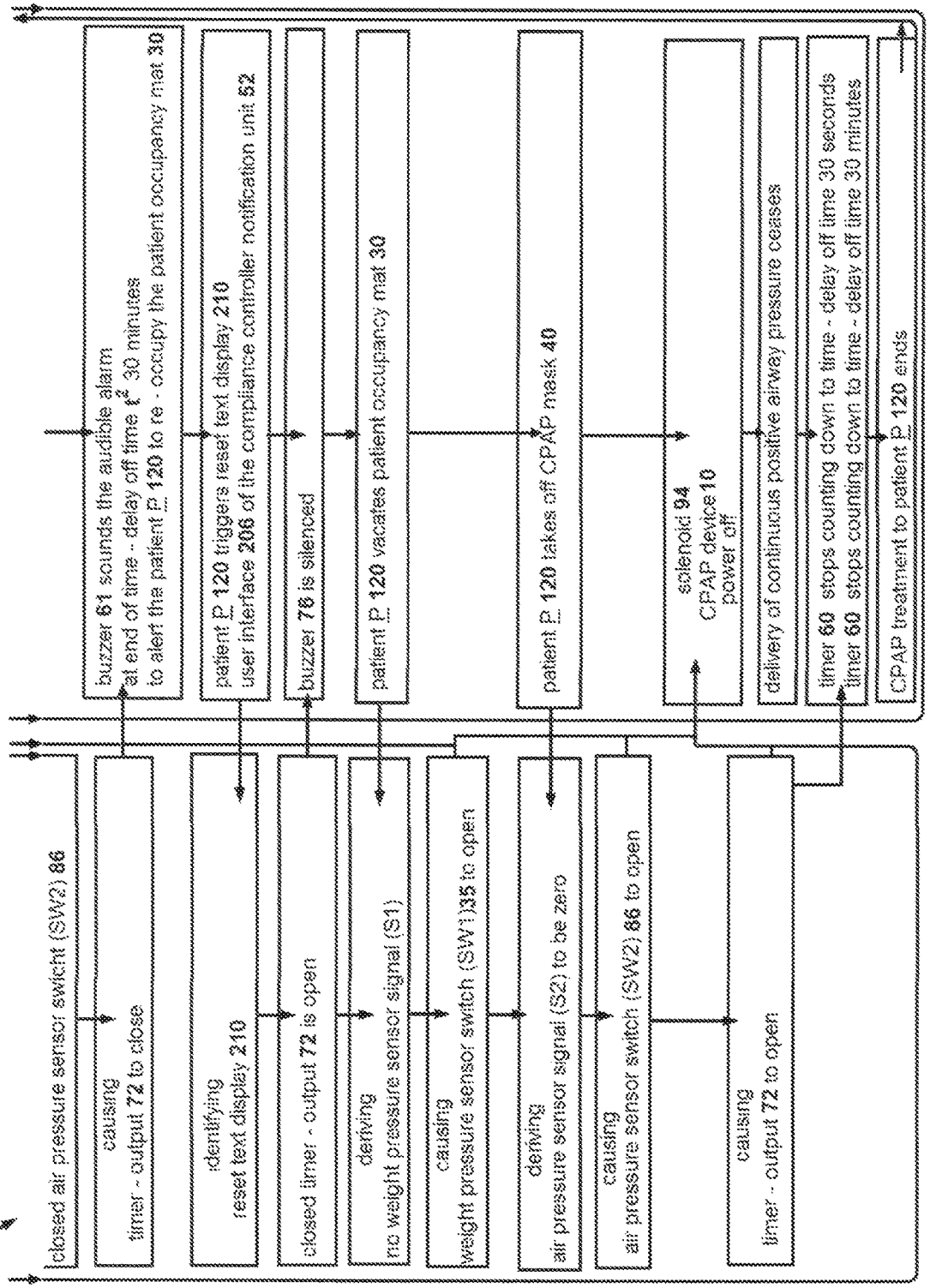
FIG. 12D shows a fourth page of the schematic illustration of an embodiment of the CPAP compliance notification method of FIG. 12A.
Figure 13A:
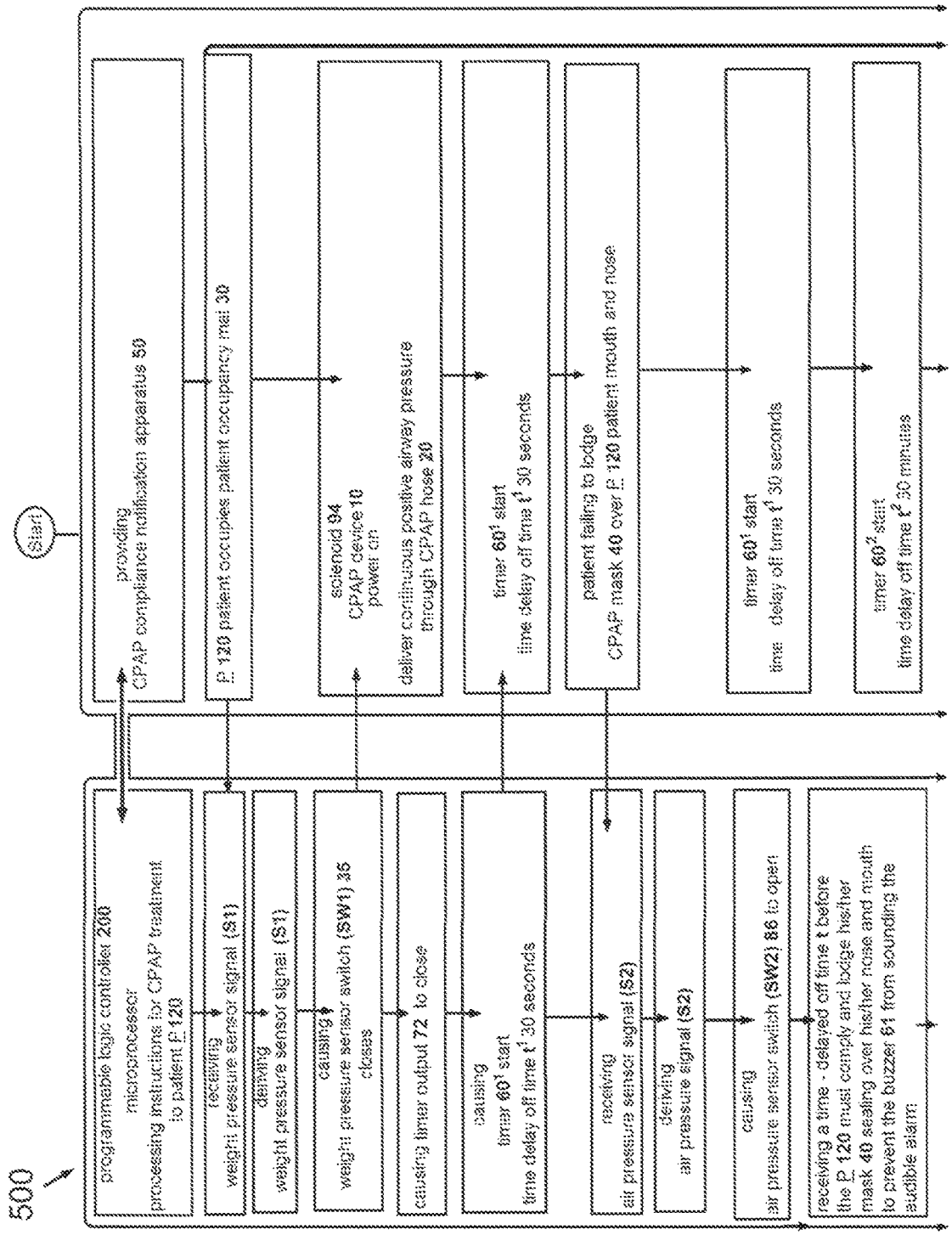
FIG. 13A shows a first page of a schematic illustration of an embodiment of a CPAP compliance notification method implementing a CPAP compliance notification apparatus.
Figure 13B:
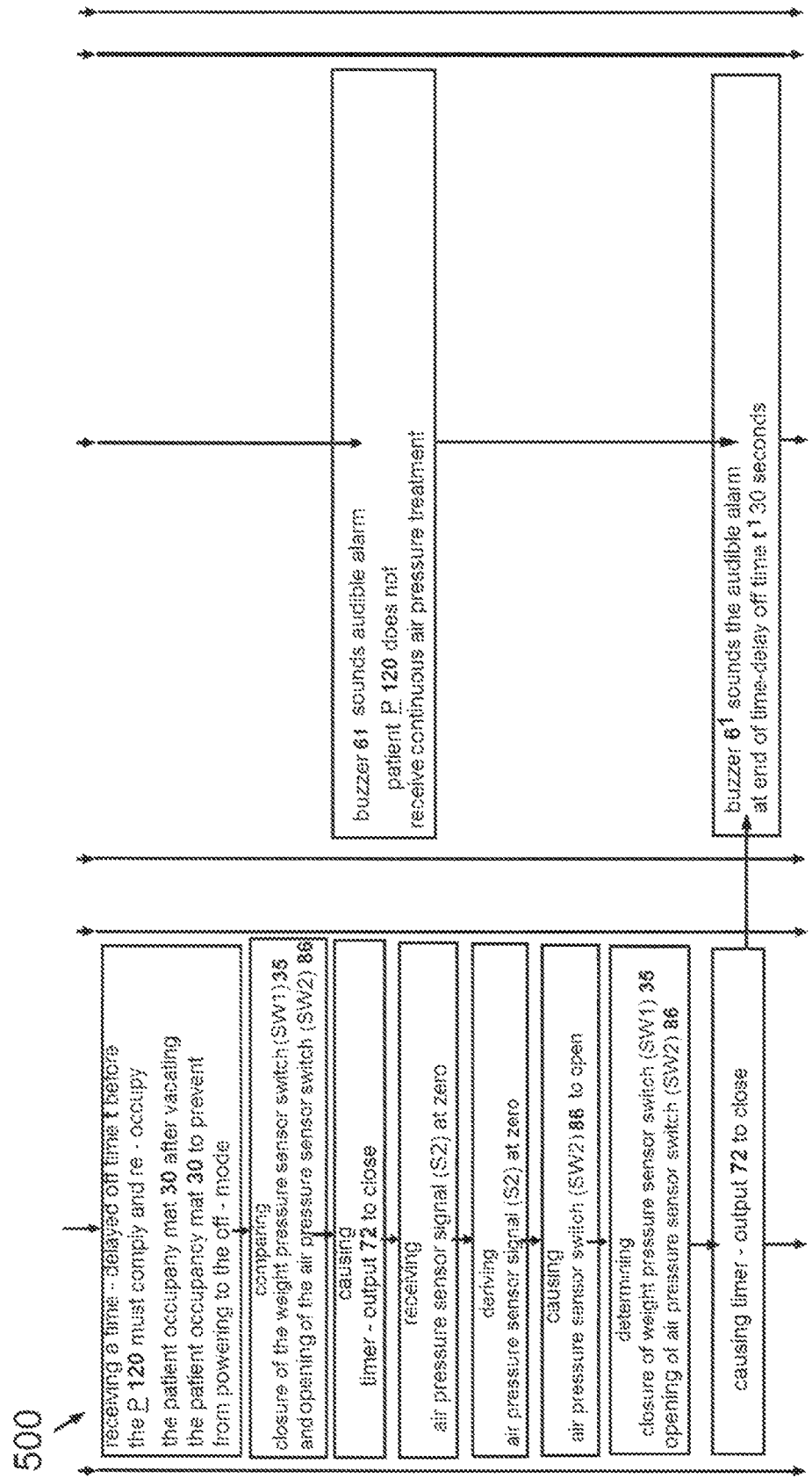
FIG. 13B shows a second page of the schematic illustration of an embodiment of a CPAP compliance notification method of FIG. 13A.
Figure 13C:
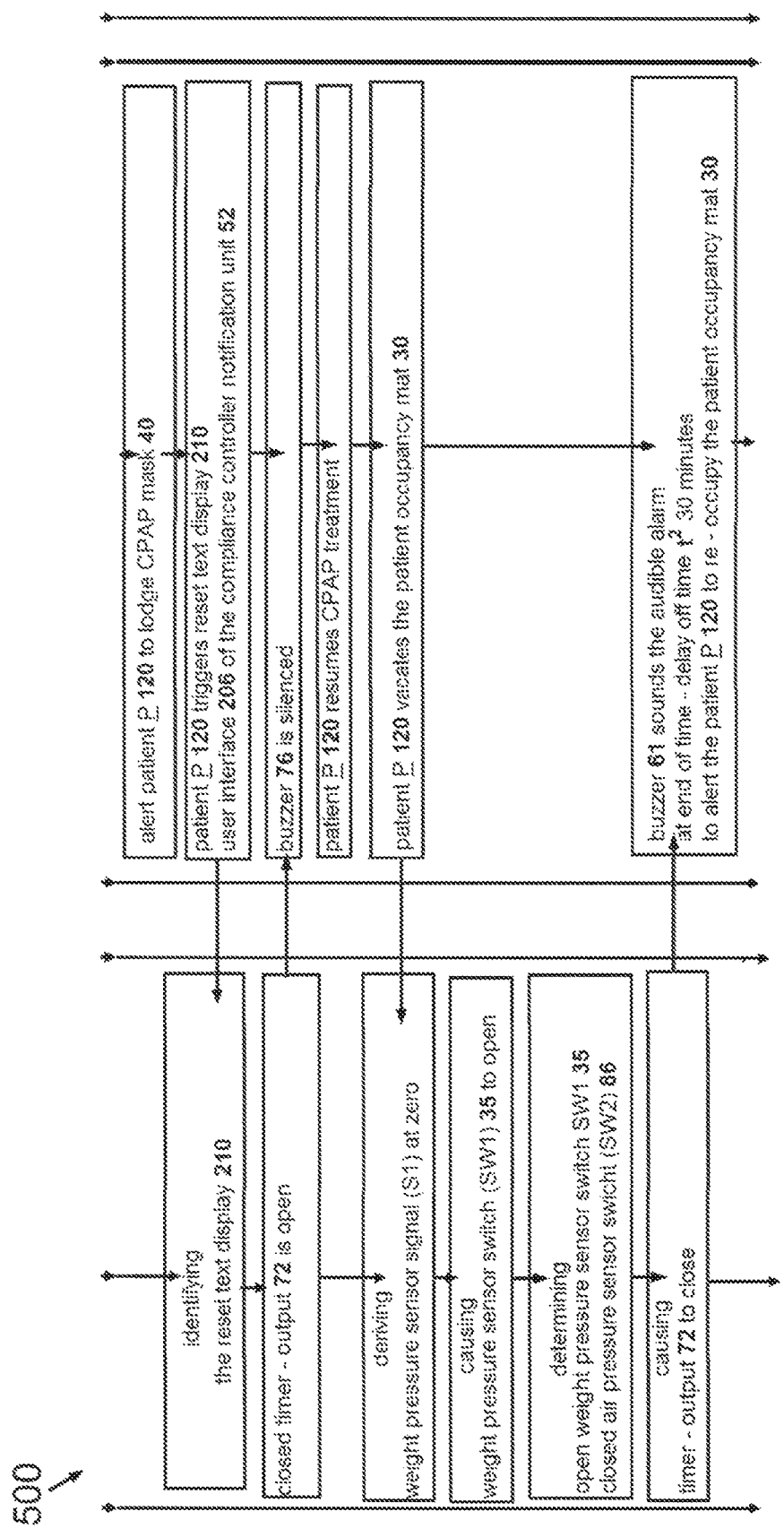
FIG. 13C shows a third page of a schematic illustration of an embodiment of a CPAP compliance notification method of FIG. 13A.
Figure 13D:
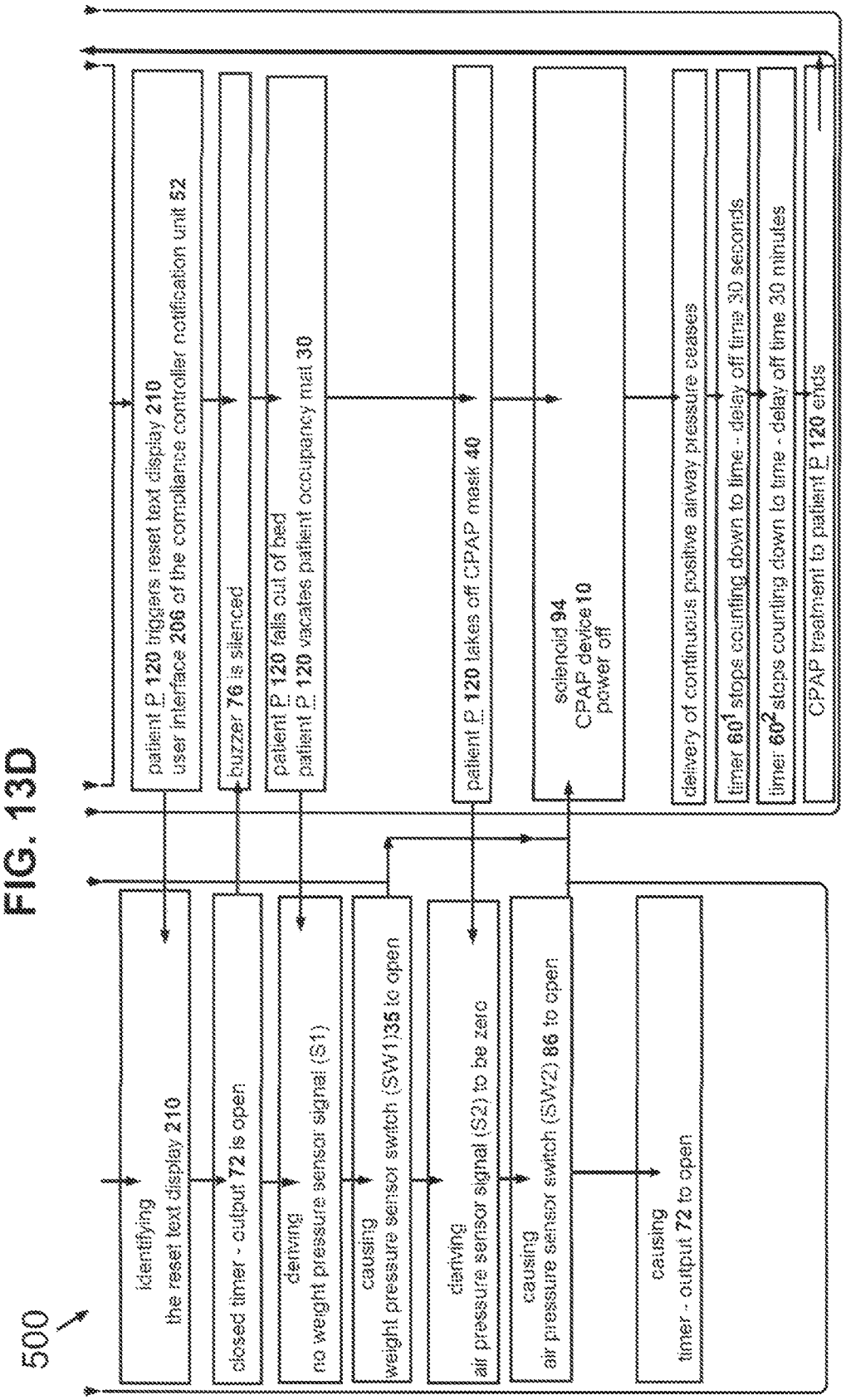
FIG. 13D shows a fourth page of a schematic illustration of an embodiment of a CPAP compliance notification method of FIG. 13A.

FIGS. 5A-6B, shows the CPAP compliance notification apparatus; FIG. 10 shows a schematic illustration of a CPAP compliance notification method 150 and FIGS. 11A-11C shows a CPAP compliance notification system 300, described in more detail below.

The CPAP compliance notification apparatus 50, CPAP compliance notification method 150, and CPAP compliance notification system 300 can be used with a plurality of types of conventional and specialty CPAP machines. However, for purposes of the disclosure, here, an exemplary embodiment of the CPAP compliance notification apparatus 50 and CPAP compliance notification method 150, and CPAP compliance notification system 300, is described for use with a conventional CPAP device 10, as shown in FIGS. 1A-1B, having a CPAP hose 20, and a CPAP mask 40.

In the embodiment of the disclosure, the CPAP compliance notification apparatus 50 comprises a CPAP device 10, CPAP hose 20, and CPAP mask 40 wherein the CPAP compliance notification apparatus includes the air pressure tube adaptor 88 to adapt an air pressure tube 80 to the air pressure sensor 84 housed within the compliance notification controller unit 52 and the CPAP hose 20 proximate to the flow generator outlet 18$^1$, of the CPAP flow generator 18. In the exemplary embodiment of the disclosure, the air pressure tube adapter 88 is an extension tube 88. The CPAP compliance notification apparatus 50 and CPAP compliance notification method 150, and CPAP compliance notification system 300 includes operation for detecting changes in weight pressure indicative of a patient's P 120 immediate occupancy or vacancy of the patient occupancy mat 30, placed immediately below a supportive substrate 124, wherein the patient occupancy mat 30 includes the weight pressure sensor 32 in simultaneous communication the CPAP compliance notification apparatus 50 includes the air pressure sensor 84 for detecting changes in air pressure channeled through an air pressure tube 80, wherein the air pressure tube 80 is releasably connected to the air pressure sensor 84 remotely positioned within the compliance notification controller unit 52 away from the source of air pressure at the patient's airways, and remotely from the flow generator, indicative of the patient P 120 initially lodging or failure to lodge a CPAP mask 40, or re-lodging or failure to re-lodge the CPAP mask 40, mis-aligned CPAP mask, or an un-sealed leaking CPAP mask 40 upon the patient's P's 120 nose, or nose and mouth, during the patient P's 120 occupancy upon the patient occupancy mat 30 when the patient P 120 is awake or asleep; includes operation of a buzzer 61 having an audible alarm to alert the P 120 to the patient's P's 120 non-conformance and, accordingly, for the patient P 120 to lodge the CPAP mask 40 for providing continuous positive air pressure to a patient P's 120 airways for treatment of people diagnosed with sleep apnea or related sleep apnea disorders.

In the exemplary embodiment of the disclosure, the air pressure tube adapter 88 is an extension tube 88.

Figure 1A:
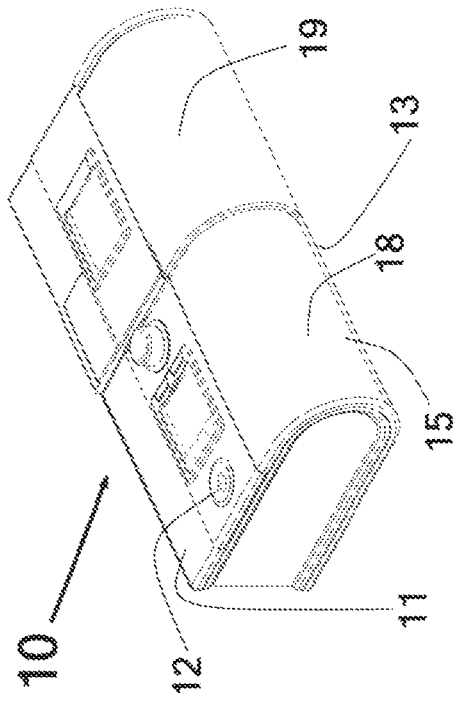
FIG. 1A shows a perspective front view of a known conventional continuous positive air pressure device (CPAP device), according to an embodiment of the present disclosure.
Figure 7:
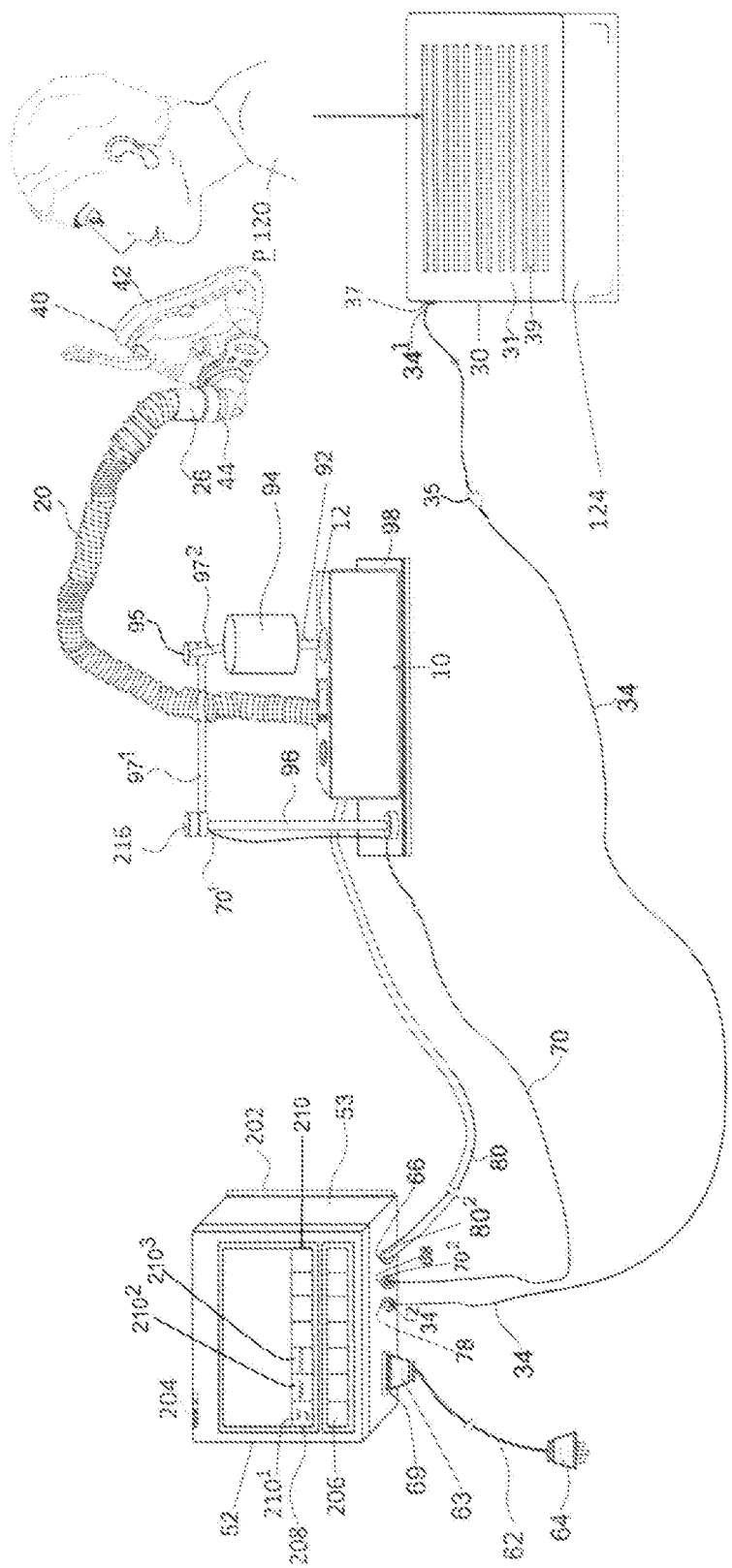
FIG. 7 shows the CPAP compliance notification apparatus implemented with the CPAP device of FIG. 1, the CPAP hose of FIG. 2, the CPAP mask of FIG. 3, the patient occupancy mat of FIG. 4, and a patient P, according to an embodiment of the present disclosure.
Figure 8:
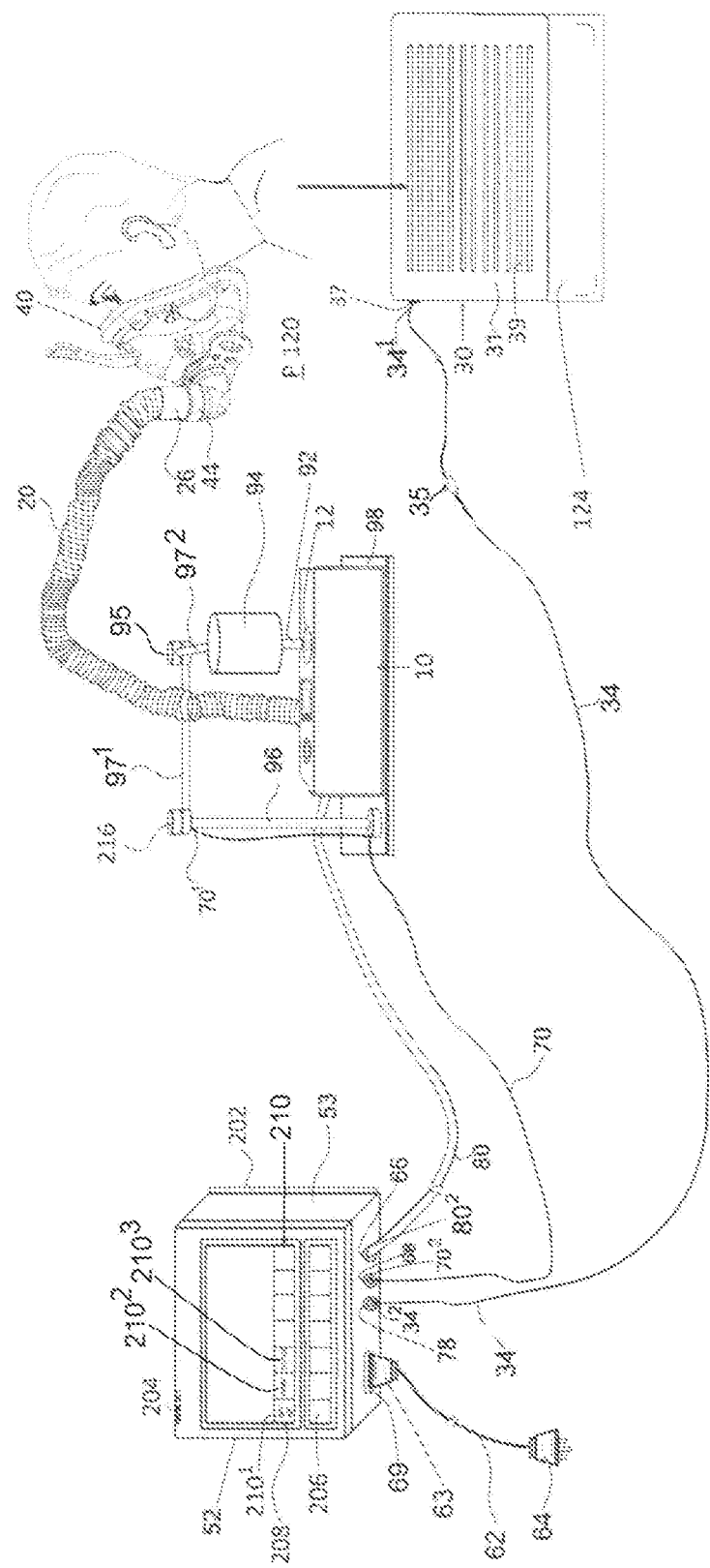
FIG. 8 shows the CPAP compliance notification apparatus implemented with the CPAP device of FIG. 1, the CPAP hose of FIG. 2, the CPAP mask of FIG. 3, the patient occupancy mat of FIG. 4, and a patient P having the CPAP mask lodged, according to an embodiment of the present disclosure.
Figure 9:
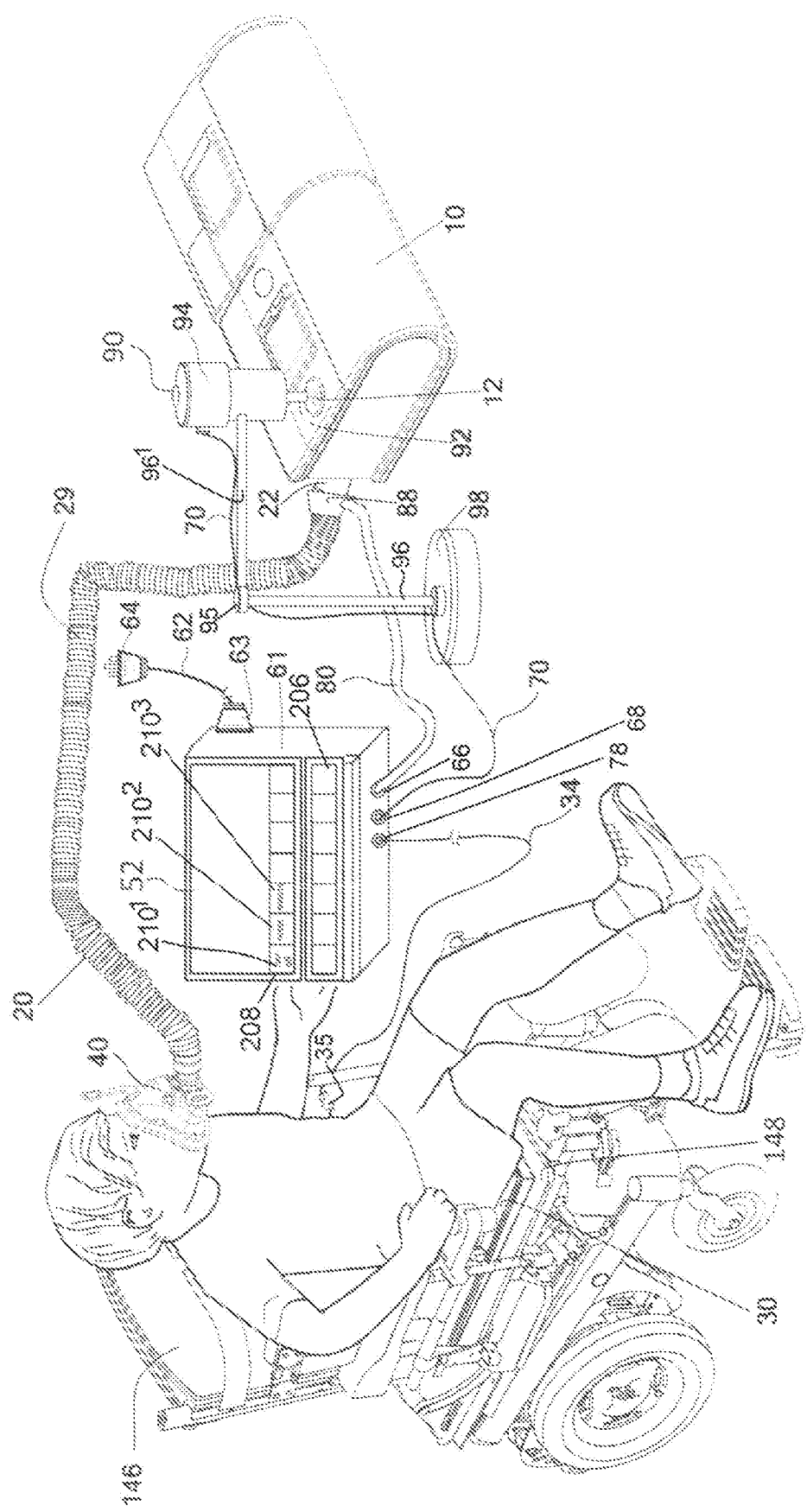
FIG. 9 shows a CPAP compliance notification apparatus implemented with the patient in a wheel chair, according to an embodiment of the disclosure.

A known conventional continuous positive airway pressure device (CPAP device) 10 in which the invention may be embodied is illustrated FIGS. 1A-1B and shown implemented with the CPAP notification compliance apparatus in FIGS. 7-9. The CPAP device 10 provides a flow of continuous positive air pressure to an airway of the patient P 120 to treat a medical sleep apnea disorder. The CPAP device 10 includes a flow generator 18 that creates a flow of breathing air pressure having a pressure greater than the ambient atmospheric pressure, referred to a flow of continuous positive air pressure.

As shown in FIG. 1A, a front perspective view of the conventional known CPAP device 10, the CPAP device 10 has a top side 11 and a bottom side 13, a front end 15 and a rear end 17. More particularly, the CPAP device 10 includes a flow generator 18 including an on/off button 12 positioned on the top side 11 of the CPAP device 10 wherein the on/off button selectively controls an on-mode and an off-mode of the CPAP device 10. In addition, as shown in FIG. 1B, a rear perspective view of the CPAP device 10, the CPAP device 10 includes a power port 16 compatible to be releasably connected with an external electrical power cable 62 which may be releasably connected to a conventional wall outlet. Further, the CPAP device 10 includes a CPAP hose 20 connection port 14 compatible to be releasably connected with a known conventional flexible CPAP hose 20, as shown in FIG. 2.

In an embodiment of the invention, the compliance and notification apparatus 50 may include a humidifier 19 releasably attached to the flow generator 18.

Referring to FIG. 2, the CPAP hose 20 includes a flexible plastic membrane 29, including two ends, a first end having a first connector cuff 22 circumventing a first opening 24 of the CPAP hose 20, and a second end having a second connector cuff 26 circumventing a second opening 28 of the CPAP hose 20, having a length L1 of flexible plastic membrane 29 therebetween for the functionality of channeling continuous positive air pressure (CPAP) therethrough the CPAP hose 20 from the CPAP device's 10 flow generator to a patient's CPAP mask 40. The first connector cuff 22 can be releasably connected to the CPAP device 10 and the second connector cuff 26 can be releasably connected to the CPAP mask (CPAP mask) 40, FIGS. 2-3 and FIGS. 7-9.

The CPAP mask 40 operates as an interface in which the patient P 120 lodges over his/her nose or nose and mouth to seal the CPAP mask 40 during his/her continuous positive air pressure therapy (CPAP therapy). In addition, the CPAP mask 40 includes a connector cuff 44 that is compatible to be releasably connected to the CPAP hose 20. The connector cuff 44 terminates at an opening 46 circumvented by the connector cuff 44.

In general, the CPAP device 10 flow generator 18 generates air flow of a breathable gas in the form of fresh air, or oxygen enriched air, having positive airway pressure that is greater than the pressure of the ambient air pressure that is delivered to the CPAP patient P 120 channeled through the CPAP hose 20 to the CPAP mask 40 when the CPAP mask is sealed over the nose, or over the nose and mouth of a patient P 120 during CPAP treatment.

In operation during CPAP therapy, the conventional CPAP device 10 flow generator 18 delivers a stream of compressed positive air pressure via the CPAP hose 20 to the CPAP mask 40 splinting the airway, and therefore, keeping the patient's P's 120 airway open under the operation of the continuous positive air pressure so that unobstructed breathing becomes possible for the patient P 120, reducing and/or preventing sleep apneas.

The CPAP mask 40 may be anyone of the types of CPAP masks including nasal mask, full facial mask, nasal pillow, hybrid, oral, total face. In an embodiment of the invention the CPAP mask 40 implemented for use with the CPAP compliance notification apparatus 50 is a full face CPAP mask 40. For means of clarity the embodiments disclosed shall refer to a face mask as the CPAP mask 40 and referenced as the CPAP mask 40 lodged onto the nose and/or nose and mouth of the patient.

Often times a patient P 120 may implement the CPAP device 10 by pressing the CPAP device on/off button 12 to the on-mode, get into bed 122, or a chair, or wheel chair 146, and read or watch t.v. and inevitably fall asleep, for example, because of fatigue associated with sleep apnea patients, before lodging the CPAP mask 40 onto his/her nose and/or nose and mouth. As a result, the patient P 120 has not complied with the physician prescribed CPAP therapy and thus, his/her sleep apnea may not improve.

In the following, a solution according to exemplary and non-limiting embodiments is disclosed and described in detail. The CPAP compliance notification apparatus 50 according to one embodiment of the invention is shown in FIGS. 5A-6B.

Figure 4:
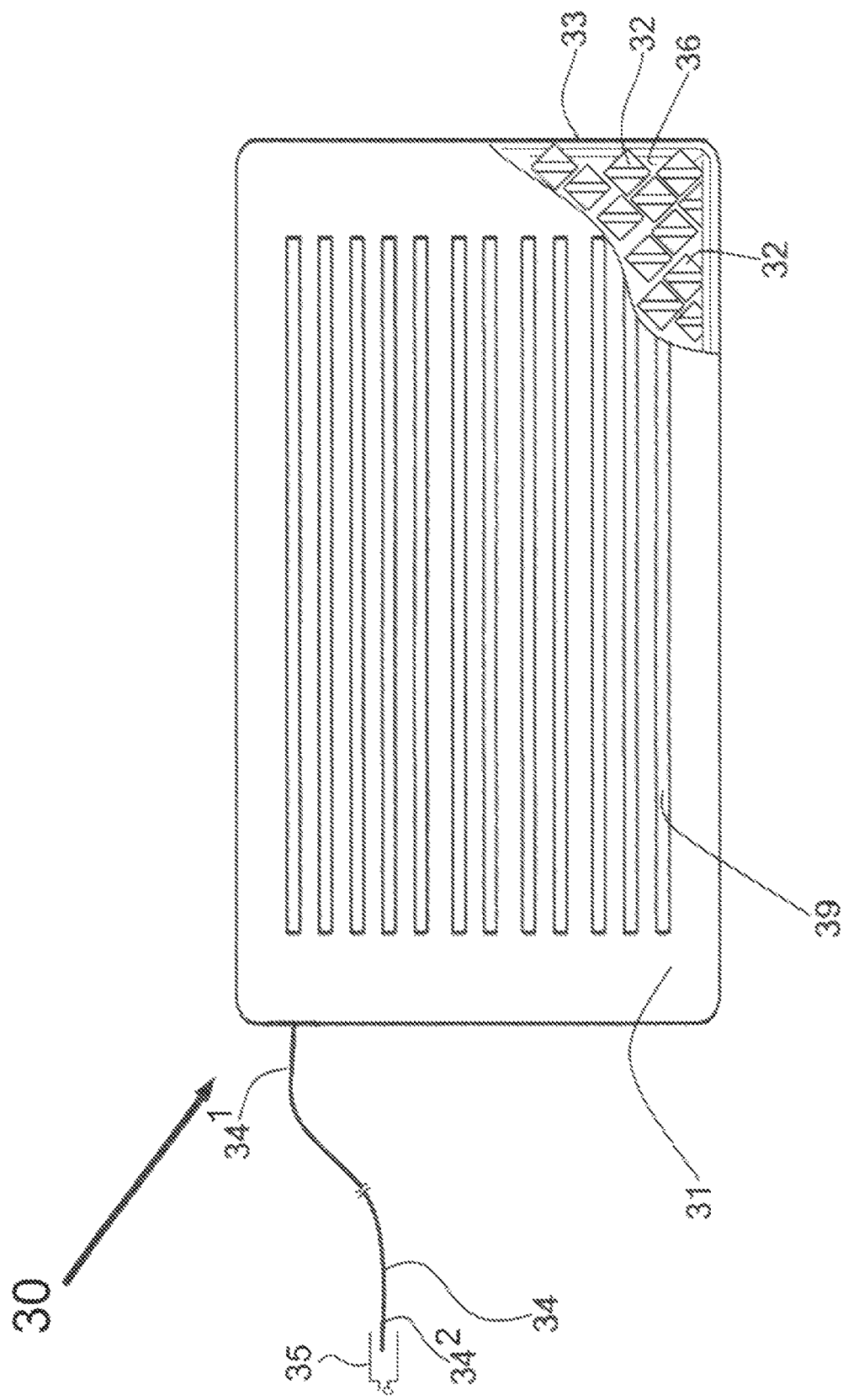
FIG. 4 shows a known conventional patient occupancy mat, according to an embodiment of the present disclosure.

The CPAP compliance notification apparatus 50 comprises the patient occupancy mat 30 having the weight pressure sensor 32 throughout a cavity 36 of the patient occupancy mat 30, as shown, more particularly, in FIG. 4. Wherein the patient occupancy mat 30 having the weight pressure sensor 32 including the weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

In addition, the CPAP compliance notification apparatus 50, includes the air pressure sensor 84 having an air pressure sensor switch SW2 86 therein positioned within the compliance notification controller unit 52 remotely from an airway of the patient P 120 and remotely from the blower outlet 18$^1$ of the flow generator 18 of the CPAP device 10, wherein the air pressure sensor 84 is operable to generate the air pressure sensor signal S2 triggered at the patient's P 120 lodgment of the CPAP mask 40 on the patient's P 120 face, wherein the air pressure sensor signal S2 is interrupted upon the patient's P 120 dislodgement of the CPAP mask 40 from the patient's P 120 face.

Figure 5A:
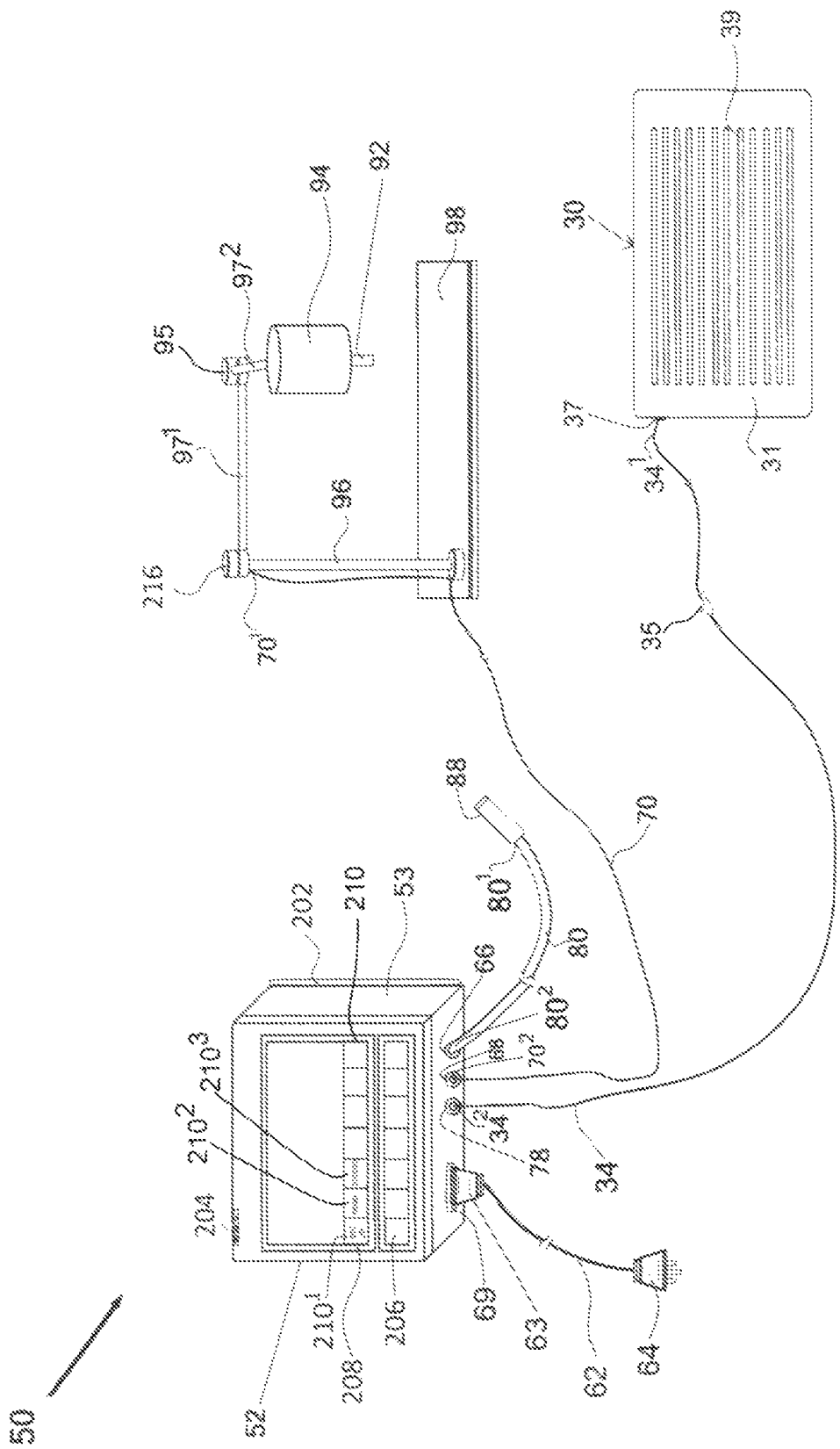
FIG. 5A shows continuous positive air pressure compliance notification apparatus (CPAP compliance notification apparatus), according to an embodiment of the present disclosure.
Figure 5B:
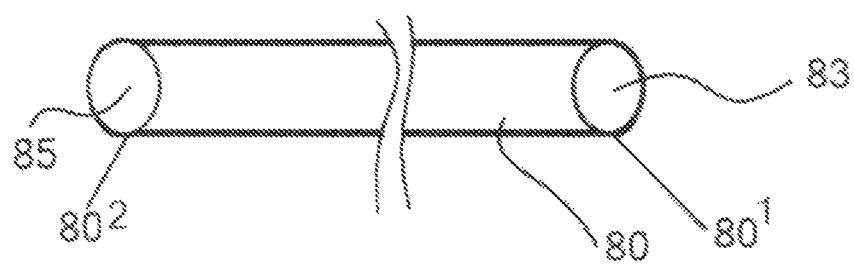
FIG. 5B shows a perspective view of an air pressure tube of the CPAP compliance notification apparatus, according to an embodiment of the present disclosure.

As shown in FIG. 5B, the air pressure tube 80 having an interior hollow channel limited by an open first end 80$^1$ having the first opening 83 can be releasable connected to the CPAP hose 20 by means of the air pressure tube adapter 88 proximate to the flow generator 18 and a second end 80$^2$ having the second opening 85 positioned releaseably connected to the air pressure sensor 84 housed within the compliance notification controller unit 52. The air pressure tube adapter 88 is the tube extender 88 having a first opening sized to be flush with the first end 80$^1$ opening of the air pressure tube 80 and an opposing second opening sized to be flush with an inlet on the CPAP hose 20, the inlet proximate to the flow generator 18. The second open end 80$^2$ of the air pressure tube communicates with an inlet port of the air pressure sensor 84.

In this exemplary embodiment, as shown in FIGS. 5A, 7-8, the solenoid 94 includes a plunger 92 coextensive with an anterior portion of the solenoid 94 and does not include a reset button 90.

Referring back to FIGS. 5A, 6A-6B, a housing 53 of the compliance notification controller unit 52, includes the housing 53 operable to maintain the compliance notification controller unit 52 components in one location proximate to each other. The compliance notification controller unit 52 components, including a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, and together with a patient P 120, to control parameters of the CPAP compliance notification apparatus 50 in implementing a compliant CPAP treatment to the patient P 120. In this exemplary embodiment of the disclosure the CPAP compliance notification apparatus 50 includes the programmable logic controller 200. As well known by the person of ordinary skill in the art, the National Electrical Manufacturers Association (NEMA) defines the programmable logic controller as a "digitally operating electronic apparatus which uses a programmable memory for the internal storage of instructions by implementing specific functions, such as logic, sequencing, timing, counting, and arithmetic to control through digital or analog I/O modules various types of machines or processes." The programmable logic controller is a "solid-state industrial control device which receives signals from user supplied controlled devices, such as sensors and switches, implements them in a precise pattern determined by ladder-diagram-based application progress stored in user memory, and provides outputs for control of processes or user-supplied devices, such as relays or motor starters." Basically, the programmable logic controller is a solid-state, programmable electrical/electronic interface that can manipulate, execute, and/or monitor, at a very fast rate, the state of a process or communication system. It operates on the basis of programmable data contained in an integral microprocessor-based system. The programmable logic controller is able to receive (input) and transmit (output) various types of electrical and electronic signals and can control and monitor practically any kind of mechanical and/or electrical system. Therefore, it has enormous flexibility in interfacing with computers, machines, and many other peripheral systems or devices. The programmable logic controller is usually programmed in ladder logic, as shown in FIGS. 11A-11C, as described in more detail below.

The one or more ports 78, 68, and 66, an electrical supply socket 69 of the type suitable for receiving a universal power cord plug 63 operable for supplying electrical power supply to the compliance notification controller unit 52; one or more DC power sources 110 operable to direct electrical power; a rechargeable battery 202; a mobile communication device docking station with charger 204; a buzzer 61; the buzzer 61 including a timer-output adapted and operable to direct an audible alarm to the patient P 120, the audible alarm having sufficient intensity to alert the patient P 120, whereby the buzzer 61 is adapted and operable to alert the patient P 120 during the patient's P 120 occupancy on the patient occupancy mat 30 of the interruption in air pressure at an interior channel of the air pressure tube 80 indicative that the patient P 120 has not lodged his/her CPAP mask 40 within one or more assigned time delay off-time(s).

The user interface 206 including a touch screen 208 includes one or more text displays 210. A first text display $210^1$ of the one or more text displays 210 includes an on/off text display $210^1$, wherein the on/off text display $210^1$ being adapted and operable when pressed to direct an "on-mode" and an "off-mode" of the CPAP device 10 via contact of the solenoid 94 plunger 92 against an on/off button of the CPAP device 10 when the patient P 120 occupies the patient occupancy mat 30.

A second text display $210^2$ of the one or more text displays 210 includes a reset text display $210^2$, wherein the reset text display $210^2$ being adapted and operable when pressed to direct an audible alarm of the buzzer 61 to turn off.

A third text display $210^3$ of the one or more text displays 210 includes a snooze text display $210^3$, wherein the snooze text display $210^3$ being adapted and operable when pressed to direct one or more timers 60 within the programmable logic controller 200 to delay the buzzer 61.

The programmable logic controller 200, as shown in FIG. 6B is configured and adapted to implement parameters to perform the CPAP compliance notification methodology 150 of a compliant continuous positive airway pressure treatment for the patient P 120, wherein the programmable logic controller 200, comprising one or more microprocessors is configured to receive instructions to implement the CPAP compliance notification method 150 of a CPAP treatment for the patient P 120, one or more timers 60, receive digital input data, receive analog input data; transmit digital output data; wherein digital input data includes identifying, parameters of the weight pressure sensor signal S1, the weight pressure sensor switch SW1 35, and parameters of the one or more timers 60, wherein analog input data includes identifying parameters of the air pressure sensor signal S2, the air pressure sensor switch SW2 86, and wherein the digital output includes identifying parameters of the buzzer 61, the solenoid 94, and the user interface 206.

As illustrated in FIG. 9, the solenoid 94 is supported by a stand 98 having a rigid vertical arm 96 and a movable horizontal arm $96^1$ manipulated by a thumb nut 95. In another embodiment, of the disclosure the solenoid 94 includes the stand 98 having the rigid vertical arm 96, and a first horizontal arm $97^1$ and a second horizontal arm $97^2$, the first horizontal arm $97^1$ and the second horizontal arm $97^2$ manipulated by a thumb nut 95, and the rigid vertical arm 96 and the first horizontal arm $97^1$ manipulated by a first thumb nut 216, as shown in FIG. 5A. In the preferred embodiment, the stand 98 is a rectangular mounting platform 98 for the CPAP compliance notification apparatus 50.

Referring to FIG. 6B the DC power supply 110 housed within the compliance notification controller unit 52 can be 110 VAC to 24 VDC 3 AMP. The DC power supply 110 can be releasably connected to the external electric power cable 62. In the exemplary embodiment of the disclosure the DC power supply 110 provides a voltage indicated by +24 voltage. The DC power supply 110 provides a power source to the to the compliance notification controller unit 52 and the components therewithin, including the rechargeable battery 202, the mobile communication device docking station 204, the buzzer 61, the air pressure sensor 84, a 12 volt battery 111, the rechargeable battery 202, the user interface 206, the programmable logic controller 200. In addition, the DC power supply 110 provides the power source to the solenoid 94. The battery of 12 volts is provided to supply a current of energy to the air pressure sensor 84.

As shown in FIGS. 5A and 6B the external electrical power cable 62 includes a first end, a terminal plug 64 configured to be compatible with a universal power socket, and a second end including the universal power cord plug 63, configured to be compatible with a receiving port, the electric supply socket 69, positioned on the exterior surface of the housing 53 of the compliance notification controller unit 52.

The compliance notification controller unit 52 comprises the circuitry implemented by the operation of the patient's P's 120 occupancy or vacation of the patient occupancy mat 30 including weight pressure sensor 32, the timer 60, the solenoid 94, to the compliance notification controller unit 52 and the components therewithin, including the rechargeable battery 202, the mobile communication device docking station 204, the buzzer 61, the air pressure sensor 84, a 12 volt battery 111, the rechargeable battery 202, the user interface 206, the programmable logic controller 200, the CPAP device 10, air pressure tube 80, and air pressure sensor 84 indicative of patient's compliance of lodging of his/her CPAP mask 40 sealed upon the patient's P's 120 nose and mouth to receive the prescribed continuous positive air pressure treatment.

In the embodiment of the compliance notification controller unit 52, referring to FIGS. 5A-9, the compliance notification controller unit 52 includes at least three receiving portals 66, 68, and 78. A first receiving port 66 provides a through port into the compliance notification controller unit 52 through which the air pressure tube 80 passes throughin and accordingly the air pressure tube 80 at the first end $80^1$ having the first opening 83 can be releasable connected to the CPAP hose 20 by means of the air pressure tube adapter 88 proximate to the flow generator 18 and the second end $80^2$ having the second opening 85 positioned releaseably connected to the air pressure sensor 84 housed within the compliance notification controller unit 52. The air pressure tube adapter 88 is the tube extender 88 having a first opening sized to be flush with the first end $80^1$ opening of the air pressure tube 80 and an opposing second opening sized to be flush with an inlet on the CPAP hose 20, the inlet proximate to the flow generator 18. The second open end $80^2$ of the air pressure tube communicates with an inlet port of the air pressure sensor 84.

A second receiving port 68 provides a through port through which a solenoid cable 70 is passed throughin and accordingly the solenoid 94 can be releasably connected to the programmable logic controller 200 within the compliance notification controller unit 52.

A third receiving port 78 provides a through port into the compliance notification controller unit 52 through which a patient occupancy mat cable 34 passes throughin and accordingly the patient occupancy mat 30 including the weight pressure sensor 32 can be releasably connected to the programmable logic controller 200 within the compliance notification controller unit 52.

Referring to FIGS. 5A-6B, the patient occupancy mat 30 is releasably connected to the compliance notification controller unit 52 by means of a hard wired cable, a patient occupancy mat cable 34 having a first end $34^1$ connecting to the patient occupancy mat and the second end $34^2$ connecting to the programmable logic controller 200.

The CPAP device 10 having the flow generator 18 is connected to the compliance notification controller unit 52 via the air pressure tube 80. The air pressure tube 80 is releasably connected to the air pressure sensor 84, which is housed in the compliance notification controller unit 52.

In the embodiment of the disclosure, as shown in FIGS. 5A-6B a reset feature, a reset text display $210^2$, from the touch screen 208 of the compliance notification controller unit 52 is used to silence the buzzer 61 and restart the CPAP compliance notification device 10.

In one embodiment, a reset button 90 can be positioned vertically anteriorly to a solenoid 94, as shown in FIG. 9, wherein the solenoid 94 is connected to the compliance notification controller unit 52 via a hard wired cable, a solenoid cable 70.

A first end of the solenoid cable $70^1$ is connected to the solenoid 94 and a second end of the solenoid cable $70^2$ is releasably connected to the programmable logic controller 200.

According to an exemplary embodiment of the invention, the patient occupancy mat 30 may be positioned approximate to a supportive substrate 124, for example, a bed mattress 122, or a seat 148 of a wheel chair 146. Other supportive substrates 124 contemplated in other embodiments include at least any one of sofa, couch, cushion, seat, chair, recliner chair, arm chair, infant crib, high chair, baby seat, vehicle car seat, an infant car seat, a carriage, a booster seat, seat on an airplane, a seat on a train, or a support substrate associated with an ambulance, air mattress, any sleep medium, any sitting medium, or any supportive substrate 124.

The patient occupancy mat 30 includes the weight pressure sensor 32 which in response to the patient's P's 120 weight upon the patient occupancy mat 30, generates a weight pressure sensor signal S1 which is generated immediately upon the patient P 120 occupying the patient occupancy mat 30, for example, when the patient P 120 gets into bed having a patient occupancy mat 30 including the weight pressure sensor 32 therein positioned approximate to the bed, and thereby the weight pressure sensor signal S1 is sustained during the patient's P's 120 occupancy of the bed 124.

The weight pressure sensor 32 includes the weight pressure sensor switch SW1 35 which closes upon receipt of the weight pressure sensor signal S1 and accordingly voltage is provided to the programmable logic controller 200. Accordingly, a timer 60 of one or more timers 60 within the programmable logic controller 200 is powered to an-on mode to count down to the pre-assigned delay off-time selected by the patient P 120. The assigned time delay off-time limit can be 30 seconds $t^1$ or 30 minutes $t^2$, or any time preselected from a variety of times customized for the patient P 120.

In the exemplary embodiment, in simultaneous communication with the programmable logic controller 200, in response to the weight pressure sensor signal S1 the conventional CPAP device 10 is powered to on-mode and accordingly the flow generator 18 starts to deliver the continuous positive air pressure through the CPAP hose 20 to the patient's P's 120 CPAP mask 40. In particular, voltage is provide to the solenoid 94 which powers the solenoid 94 such that the plunger 92 pushes down on the CPAP device 10 on/off button and accordingly, the conventional CPAP device 10 is placed in the on-mode and accordingly the flow generator 18 starts to deliver the continuous positive air pressure through the CPAP hose 20 to the patient's CPAP mask 40.

The buzzer 61 includes an audible alarm directed to a patient P 120 with sufficient volume to be heard by the patient P 120, housed within the compliance notification controller unit 52. The buzzer 61 includes a timer-output 72 which when closed provides a voltage to the buzzer 61. In another embodiment of the disclosure the buzzer 61 may include an audible alarm further comprising a vibration feature, a light feature.

A timer 60 of the one or more timers 60 within the programmable logic controller 200 includes a programmable time-delay off time t which can be selected and assigned by the patient P 120 such that the patient P 120 can delay a signal to sound the audible buzzer 61 to alert the patient P 120 in the event that the patient P 120 fails to initially lodge his/her CPAP mask 40, and in the event the patient P 120 fails to re-lodge his/her dislodged CPAP mask 40, or in the event that the seal around the CPAP mask 40 is leaking.

The timer 60 can be set to a first assigned time delay off-time limit $t^1$ or a second assigned time delay off-time limit $t^2$. The first assigned time delay off-time limit $t^1$ is selected by the patient P 120 and is established based upon the time the patient P 120 needs before he/she wishes to lodge the CPAP mask 40 prior to CPAP treatment as the patient P 120 is awake, and thereby, the buzzer 61 is sounded to alert the P 120 in the event that the patient P 120 does not initially lodge the CPAP mask 40 on his/her nose or nose and mouth prior to CPAP treatment in the event the patient P 120 forgets, gets distracted, or falls asleep.

The second assigned time delay off-time limit $t^2$ chosen by the patient P 120 can be longer or shorter time limit than the first assigned time delay off-time limit $t^1$.

The timer 60 provides the patient P 120 to select one or more pre-selected time delay off-times t to provide a time signal to the compliance notification controller unit 52 in order to delay the audible buzzer 61 in the event the patient's P's 120 mask 40 is not initially lodged or re-lodged within the end limit of the assigned time delay off-time limit t.

The patient P 120 can trigger the timer 60 to start counting down to the assigned time delay off-time limit t at the commencement of CPAP therapy by the patient P 120 taking the following steps, and described in more detail below, including, the patient P 120 setting the timer 60 of the one or more timers 60 to the assigned time delay off-time limit t; the patient occupying the patient occupancy mat 30 causing the timer 60 to start counting down towards the assigned time delay off-time limit t and in simultaneous communication causing the CPAP device 10 to power to the on-mode; and in the event of the patient's P's 120 failure to lodging the CPAP mask 40 onto the patient's P's 120 nose, and/or nose and mouth within the assigned time delay off-time limit t causing the audible alarm of the buzzer 61 to sound, or not re-lodging the CPAP mask 40 onto the patient's P's 120 nose, and/or nose and mouth within the assigned time delay off-time limit t causing the audible alarm of the buzzer 61 to sound so that the patient P 120 is alerted to lodge his/her CPAP mask 40 so that the patient P120 is compliant and receive the CPAP treatment.

The timer's 60 assigned time delay off-time limit t parameter need only be pre-set once by the patient P 120.

In an embodiment of the disclosure, it is known that a patient P 120 can prefer to watch t.v. or to read before a sleep cycle and accordingly before the P 120 lodges his/her CPAP mask 40 to receive the continuous positive air pressure prescribed treatment, the CPAP treatment. Because, the patient P 120 has occupied the patient occupancy mat 30, the CPAP device 10 is immediately triggered to the on-mode.

Thus, the patient P 120 can program the timer 60 to be set with the assigned time delay off-time limit of 30 minutes $t^2$ to allow the patient P 120 30 minutes $t^2$ to watch a t.v. program or to read before the audible alarm of the buzzer 61 alerts the patient P 120 that he/she has failed to initially lodge his/her CPAP mask 40.

Similarly, in the referred exemplary embodiment, the patient P 120 can occupy the patient occupancy mat 30 triggering the CPAP device 10 to the on-mode and accordingly the patient P 120 can initially lodge his/her CPAP mask 40. In the event the patient's P 120 CPAP mask 40 becomes dislodged thereafter and while the patient P 120 occupies the patient occupancy mat 30, the patient P 120 has 30 minutes $t^2$ to re-lodge the dislodged CPAP mask 40 before the buzzer 61 sounds the audible alarm to alert the patient P 120 to re-lodge his/her CPAP mask 40.

In another exemplary embodiment, the patient P 120 can pre-set a timer 60 of the one or more timers 60 to 30 seconds $t^1$, as the first assigned time delay off-time limit $t^1$.

The buzzer 60 can function to operate the implementation of the audible alarm having sound that has sufficient volume to alert an awake patient P 120, and a sleeping patient P 120. The audible alarm of the buzzer 61 is sounded in the event the patient P 120 does not initially lodge his/her CPAP mask 40, or re-lodge his/he CPAP mask 40 or adjust his/her leaking CPAP mask 40 before the end limit of the assigned time delay-off time limit t. When the audible alarm of the buzzer 61 is sounded the awake or asleep patient P 120 is alerted to lodge, re-lodge, or adjust his/her CPAP mask 40 and when the patient P 120 does relodge his/her CPAP mask 40 correctly, in simultaneous consideration the timer 60 stops counting down, and in response the patient P 120 can press the reset button 90, as shown in FIG. 9, or press the reset text display $210^2$ on the touchscreen 208 of the user interface 206, as shown in FIGS. 5A, 7-8, to silence the audible alarm of the buzzer 60.

The timer 60 can be assigned by the patient P 120 by means of programming the timer 60 one or more microprocessors of the programmable logic controller 200. As mentioned above, the patient can program the assigned time delay off-time limit to 30 seconds $t^1$ or to the assigned time delay off-time of 30 minutes $t^2$. As one skilled in the art will know, the assigned time delay off-time limit t can be calibrated to a variety of time periods. In one aspect of the embodiment of the disclosure, the assigned time delay off-time limit t, thereby, is the period of time the patient P 120, while occupied on the patient occupancy mat 30, would choose to allow himself/herself to be non-compliant in not lodging his/her CPAP mask 40 or not re-lodging a dislodged CPAP mask 40 before the patient P 120 is alerted by the buzzer's 61 audible alarm to notify the patient P 120 that his/her CPAP mask 40 is not lodged.

In operation when the patient P 120 occupies the patient occupancy mat 30 the weight pressure sensor signal S1 powers the weight pressure sensor switch SW1 35 to close providing voltage to the programmable logic controller 200, as shown in FIG. 11A and accordingly powering the timer 60 to start counting down to the end-limit of the 30 minutes $t^2$. In the embodiment of the disclosure, as shown in FIGS. 5A-6B a reset feature, a reset text display $210^2$, on the touch screen 208, of the user interface 206 of the compliance notification controller unit 52 is used to silence the audible alarm of the buzzer 61 and in simultaneous communication because the patient P 120 remains on the patient occupancy mat 30 the CPAP compliance notification device 10 remains in the on-mode.

In another embodiment of the disclosure, the reset button 90 is positioned immediately vertically superior to the solenoid 94, as shown in FIG. 9. The reset button 90 is provided for the function of implementing the operation of the CPAP device 10 on/off button, the operation of the buzzer 60, and restarting the timer 60.

The solenoid 94 including a plunger 92 is operationally positioned anteriorly vertically above the on/off button 12 of the conventional CPAP device 10 and accordingly when the patient P 120 depresses the reset button 90 the plunger 92 is pushed against the CPAP device 10 on/off button 12 such that the CPAP device 10 can be turned on and off.

In another embodiment of the disclosure, referring again to FIGS. 5A-8, the solenoid 94 does not include the reset button 90. The exemplary embodiment includes the patient P 120 pressing the reset feature, the reset text display $210^2$, on the touch screen 208 of the user interface 206 which implements the operation of the CPAP device 10 to turn on and off, and provides a function to silence the audible alarm of the buzzer 61 when sounded, and restart the timer 60 in the event the timer 60 has reached the assigned time delay off-time limit t in the event the patient P 120 has failed to initially lodge his/her mask within the assigned time delay off-time limit t, or in the event the patient P 120 has failed to re-lodge a dislodged mask, or adjust a leaking mask 40 within the assigned time delay off-time limit t.

The patient occupancy mat 30 includes a top shell 31 of the patient occupancy mat 30 and a bottom shell 33 of the patient occupancy mat 30 sealed along the entire periphery enclosing a cavity 36 therebetween, as shown in FIG. 4. The patient occupancy mat 30 includes the weight pressure sensor 32 positioned throughout the cavity 36 including the weight pressure sensor switch SW1 35, and the patient occupancy mat cable 34. The top side shell 31 and the bottom side shell 36 may be made of virtually any conventional material that is air or water-tight. Exemplary materials include but are not limited to any one of or combination of plastic, polyethylene, polypropylene, latex, vinyl, etc. and fabric, canvas, etc. Fabrics may be treated with a plastic or other coating to make them air or fluid-tight. The size of the patient occupancy mat 30 can be customized to use with a variety of supportive substrates 124 including: sofa, couch, cushion, seat, chair, recliner chair, arm chair, infant crib, high chair, baby seat, vehicle car seat, an infant car seat, a carriage, a booster seat, seat on an airplane, a seat on a train, or a support substrate associated with an ambulance, air mattress, any sleep medium, any sitting medium, or any supportive substrate 124.

The patient occupancy mat 30, having the weight pressure sensor 32, may be positioned approximate to a supportive substrate 124, for example, a bed mattress or bed 122, or a seat 148 of a wheel chair 146 as shown in FIGS. 7-9. The patient occupancy mat 32, including the weight pressure sensor 32 including the weight pressure sensor switch SW1 35 is provided for the function of detecting the occupancy or the vacancy of the patient P 120 upon the support substrate 124 prior to, during, and post patient P's 120 CPAP treatment. Weight sensors are usually sensitive to a patient's P's 120 occupancy pressure indicative of the patient's weight upon the patient occupancy mat 30 and/or patient's approximation to the sensing support substrate 124.

The patient occupancy mat 30 having the weight pressure sensor 32 is provided for the function of implementing the operation of the CPAP device 10, and the operation of the timer 60 and in simultaneous communication with the air pressure sensor 84 the operation of the buzzer 61.

The patient occupancy mat 30 is portable and is releasably connected to the compliance notification controller unit 52 and includes a rechargeable battery (not shown). The patient occupancy mat 30, utilizes the patient occupancy mat 30 which is portable and adapted to be placed between the patient P 120 and a support substrate 124, such as a bed mattress 122, or seat 148 of the wheel chair 146, and any one of the supportive substrates 124 as noted above. Other supportive substrates 124 contemplated, as mentioned above, in other embodiments include at least any one of sofa, couch, cushion, seat, chair, recliner chair, arm chair, infant crib, high chair, baby seat, vehicle car seat, an infant car seat, a carriage, a booster seat, seat on an airplane, a seat on a train, or a support substrate associated with an ambulance, air mattress, any sleep medium, any sitting medium, or any supportive substrate 124. Accordingly, the patient occupancy mat 30 can be configured and accordingly sized to extend the entirety of the large supporting substrate 124 or the entirety of the small supporting substrate 124 upon which the patient P 120 occupant is to occupy.

Referring to FIG. 4 the weight pressure sensor 32 is disposed throughout the cavity 36 of the patient occupancy mat 30 so that at any point of the patient occupancy mat 30 the patient P 120 can be detected upon the patient P 120 sitting or lying on the patient occupancy mat 30. The patient occupancy mat 30 is provided with at least one electrically conductive connecting means, a hard wired patient occupancy mat cable 34 having a first end $34^1$ and a second end $34^2$.

The patient occupancy mat cable 34 electrically connects the patient occupancy mat 30 to the compliance notification controller unit 52, as shown in FIGS. 5A, 7-9. The patient occupancy mat cable 34 includes a length $L^2$ limited by the first end $34^1$ and a second end $34^2$. The first end $34^1$ of the patient occupancy mat cable 34 is attached to the patient occupancy mat 30 by means of a first connector port 37 positioned at the weight pressure sensor 32; and the second end $34^2$ of the patient occupancy mat cable 34 is releasably attached to the compliance notification controller unit 52 by means of a second connector port 78 positioned at the compliance notification controller unit 52. The patient occupancy mat 30 may include ridges 39 on the exterior surface of the top shell 31.

In accordance with the patient occupancy mat 30, the weight pressure sensor 32 includes the weight pressure sensor switch SW1 35 which detects the weight pressure changes in the patient occupancy mat 30 in response to the patient's P's 120 occupancy upon the mat 30, and continues to detect the patient P 120 for the duration of time the patient P 120 occupies the patient occupancy mat 30, and detects changes in the weight pressure upon the patient occupancy mat 30 in response to the patient's P's 120 vacating the patient occupancy mat 30.

FIGS. 5A-9 is a perspective view together referenced with a schematic view of the CPAP compliance notification apparatus 50 illustrating the weight pressure sensor 32 within the patient occupancy mat 30 releasably connected to the compliance notification controller unit 52. The weight pressure sensor 32 is connected to the compliance notification controller unit 52 via the programmable logic controller 200 having one or more microprocessors which integrates electrical signals, and in particular, in response to the weight pressure sensor signal S1.

The patient occupancy mat 30 including the weight pressure sensor 32 provides implementation to operation of the CPAP device 10, and the timer 60. Upon the patient P 120 occupying the patient occupancy mat 30 the weight pressure sensor 32 generates weight pressure sensor signal S1 powering weight pressure sensor switch SW1 35 to close providing voltage so that the CPAP device 10 is powered to an on-mode and starts delivery of the continuous positive air pressure channeled through the CPAP hose 20 to the patient's P 120 CPAP mask 40 and subsequently to the patient P 120. In simultaneous communication with the weight pressure sensor signal S1, accordingly, one of the timers 60 of the one or more timers 60 starts counting down to the assigned time delay off-time limit t, for example, $t^2$ 30 minutes. And in simultaneous communication, the patient's P 120 CPAP mask 40 is not lodged on the patient's P 120 face the timer 60, accordingly, will continue to count down to the an end-limit of the assigned time delay off-time limit, for example, in this scenario of 30 minutes $t^2$. Thereby, if the patient P 120 has not lodged his/her CPAP mask 40 within the assigned time delay-off time limit $t^2$ 30 minutes, the buzzer 61 will sound the audible alarm.

Upon the patient P 120 vacating the patient occupancy mat 30 the weight pressure sensor switch SW1 35 opens interrupting the incoming weight pressure sensor signal. Accordingly the conventional CPAP 10 is powered to the off-mode in simultaneous communication when the CPAP mask 20 is dislodged from the patient such that the CPAP flow generator 18 stops the delivery of the continuous positive air pressure through the patient's P's 120 CPAP hose 20 and CPAP mask 40, and in simultaneous consideration the timer-ouput 72 opens and the timer 60 stops counting to the assigned time delay-off time limit $t^2$. Further when the patient P 120 dislodges his/her CPAP mask 40 the air pressure sensor switch SW2 86 opens.

Referring to FIGS. 7-9, the CPAP device 10 having the CPAP hose 20 attached to the flow generator 18 delivers the stream of continuous positive airway pressure to the patient's P's 120 CPAP mask 40 at a physician prescribed air pressure, which is referred to as the titration pressure. The CPAP device 10 is pre-set by the patient P 120 to a ramp pressure based upon the prescribed titration pressure.

Figure 5C:
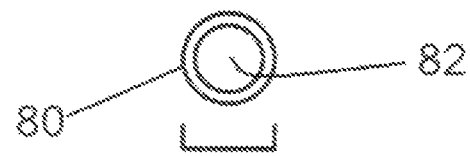
FIG. 5C shows a cross-sectional view of the air pressure tube of the CPAP compliance notification apparatus of FIG. 5B, according to an embodiment of the present disclosure.

As shown in FIGS. 5B-5C, and more particularly in FIG. 5B-5C, the air pressure tube 80 includes a first end $80^1$ circumventing a first opening 83 and a second end $80^2$ circumventing a second opening 85 and having a length $L^3$ of hollow tubular channel 82 therebetween. The air pressure tube 80 is positioned between the CPAP device 10 flow generator 18 and the compliance notification controller unit 52 for the purpose of channeling the flow of continuous positive air pressure from the flow generator 18 to the remotely positioned air pressure sensor 84 within the compliance notification controller unit 52 for the function of implementing operation of the buzzer 60. The air pressure tube 80 can be made of resilient flexible material including at least any one of or combination of a rubber, plastic, pvc, and flexible nylon tubing.

Referring to FIGS. 5A-9, the first end of the air pressure tube $80^1$ includes the air pressure tube adapter 88 tube extension 88 including an opening flush with the first opening 83 of the air pressure tube 80 which provides a connector cuff such that the air pressure tube's 80 first end $80^1$ can be releasably connected to the flow generator 18 of the CPAP device 10. The air pressure tube adapter 88 positions the first opening 83 of the air pressure tube 80 into the first end of the CPAP hose 20 immediately adjacent to the CPAP hose's 20 first connector cuff 22 which is releasably connected to the CPAP hose 20 receiving port 14 while the second end of the air pressure tube 80 is releasably connected to the air pressure sensor 84 housed in the compliance notification controller unit 52 for the functionality that changes in airway pressure indicative of the failure of the patient P 120 to lodge his/her CPAP mask 40, or re-lodge his/her mask 40, or a leaky CPAP mask 40 can be detected by the air pressure sensor 84.

As shown in FIG. 6B the air pressure sensor 84 is positioned remotely from the source of air pressure and positioned remotely from the airways of the patient P 120 sensed at the patient's P 120 CPAP mask 40 and remotely from the flow generator 18 such that the air pressure sensor 84 is disposed within the housing 53 of the compliance notification controller unit 52 connected to the air pressure tube 80 wherein a path of air pressure is channeled upstream from the flow generator 18 and downstream from the patient's P's 120 CPAP hose 20 connected to the patient's P's 120 CPAP mask 40, initiating from the patient's P's 120 nose and mouth airways so that the air pressure sensor 84 detects changes in air pressure in a continuous positive airway pressure. The air pressure sensor 84 can accurately monitor the air pressure during inhalation and/or during exhalation, before or during the patient's P's 120 CPAP therapy, accordingly.

The air pressure sensor 84 is positioned in the compliance notification controller unit 52 for the purpose of measuring air pressure at a location not proximate to the patient P 120 so that the patient P 120 is relieved from the cumbersome positioning of the air pressure sensor 84 on the CPAP hose 20 or the CPAP mask 40 having the potential of the structure of the air pressure sensor 84 from becoming obstructed or dislodged before, during or after the patient's P's 120 CPAP therapy. In addition, the air pressure sensor 84 is positioned remotely from the air pressure being sensed at the patient's P 120 CPAP mask 40 for the purpose of preventing the air pressure sensor 84 from becoming filled or clogged with the patient's P 120 liquid or mucus exudate.

As shown in FIG. 6B and FIGS. 7-8, the air pressure sensor 84 connected at a terminal portion of the second end 80$^2$ of the air pressure tube 80 includes means for continuous detecting air pressure which is indicative of air pressure disruptions consisting of changes in air pressure from the CPAP hose 20 or CPAP mask 40 indicative of the patient's P's 120 non-compliance that he/she has not initially lodge his/her CPAP mask 40, or changes in air pressure due to a blockage in the CPAP hose 20 or the CPAP mask 40, or changes air pressure due to leakage of air from the CPAP hose 20 or the CPAP mask 40.

When the patient lodges his/her CPAP mask 40 the air pressure sensor 84 detects a change in air pressure channeled through air pressure tube 80 and routes an air pressure sensor signal S2 powering the air pressure sensor switch SW2 86 to close.

In the embodiment of the invention, and explained in detail below, when the patient P 120 is in bed 122 equipped with the patient occupancy mat 30 having the weight pressure sensor 32 the CPAP device 10 is powered to the on-mode and the timer 60 begins to count down to the pre-assigned time delay off-time limit t selected by the patient P 120 so that the buzzer 61 will sound its audible alarm at the end-limit of the pre-assigned time delay off-time limit t in the event the patient P 120 fails to comply and lodge his/her CPAP mask 40 onto his/her nose or nose and/or mouth to receive the prescribed CPAP treatment.

First Scenario: In a first scenario of the embodiment of the invention, the patient P 120 is in bed 120 equipped with the patient occupancy mat 30 having a patient occupancy the weight pressure sensor 32 operating within the cavity 36 of the patient occupancy mat 30 and the patient P 120 decides to watch t.v. before lodging his/her mask and falls asleep before initially lodging his/her CPAP mask 40.

In particular, as depicted in FIG. 11A-11C, the patient occupancy mat 30 generates the weight pressure sensor signal S1 upon the patient occupancy of the mat 30 and the weight pressure sensor signal S1 is maintained during the time the patient P 120 is occupied on the patient occupancy mat 30. Accordingly the weight pressure sensor switch SW1 35 closes and accordingly the CPAP device 10 is turned to on-mode, and, concurrently, for the assigned time delay off-time limit of 30 minutes t$^2$ and accordingly the timer 60 is engaged and starts to count down to the assigned time delay-off time limit t$^2$ having an end-limit of 30 minutes. In the event, the patient P 120 falls asleep watching t.v. or reading, and he/she fails to comply and does not lodge his/her CPAP mask 40 and the air pressure is 12 volts current or falls to zero the air pressure sensor switch 86 opens, accordingly, the timer 60 remains engaged and continues counting down towards the time delay off-time of 30 minutes t$^2$. In the event the patient P 120 does not lodge his/her mask before the timer reaches the assigned time delay off-time limit of 30 minutes t$^2$ the timer-output 72 closes and accordingly the audible buzzer 61 is engaged such that the buzzer 61 sounds the audible alarm to alert the patient P 120 to lodge his/her CPAP mask 40.

While the patient P 120 remains occupied on the patient occupancy mat 30 and in the event the reset button 90 is pressed because the audible alarm of the buzzer 61 has sounded indicative of the patient's non-compliance of a failed CPAP mask 40 not corrected before the assigned time delay off-time limit t$^2$ of 30 minutes, the patient P 120 can press the reset feature, the reset feature being the reset text display 210$^2$, such that the plunger 92 is pushed against the CPAP device 10 on/off button 12 and accordingly the CPAP device 10 is powered remaining in the on-mode so that the conventional CPAP flow generator 18 continues to deliver continuous positive air pressure through connected CPAP hose 20 to patient's P 120 CPAP mask 40. In simultaneous consideration, when the plunger 92 is depressed against the CPAP device 10 on/off button 12 the buzzer 61 when sounding the audible alarm is silenced, and the timer 60 restarts. Accordingly, the CPAP device 10 is maintained in the on-mode because the patient remains on the patient occupancy mat 30 providing the weight pressure sensor signal S1 such that the weight pressure sensor switch SW1 35 remains closed powering the CPAP machine 10 to the on-mode.

The reset button 90 can be remotely positioned proximate to the patient P 120 so that when the remote reset button 90 is pressed the solenoid 94 plunger 92 pushes against the CPAP device 10 on/off button 12.

In use, the patient occupancy mat 30 having the weight pressure sensor 32 is placed between the patient P 120 and the support substrate 124 such as a bed mattress 122 or a wheel chair 146 seat 148 or any supportive substrate 124 mentioned above. When the patient P 120 laying on the patient occupancy mat 30 for, example, when the patient is lying in bed 122, or sitting in bed 122 when the patient P 120 is awake in bed 122, for example, watching t.v., or reading, the patient's P's 120 weight creates a pressure on the patient occupancy mat 30 that can propagate a force on the weight pressure sensor 32 generating the weight pressure sensor signal S1 powering the weight pressure sensor switch SW1 35 to close providing input data to the programmable logic controller 200 causing the plunger 92 of the solenoid 94 to press against the on/off button 12 of the CPAP device 10, and accordingly the CPAP device 10 starts automatically and in simultaneous consideration the timer 60 starts automatically.

In another scenario, the patient P 120 is awake and is in bed 124 equipped with the patient occupancy mat 30 including the weight pressure sensor 32 but has failed to initially lodge his/her CPAP mask 40 to receive his/her continuous positive air pressure therapy.

It is a known patient P 120 preference for the patient P 120 to read or watch t.v. while he/she is in bed 124 before he/she lodges the CPAP mask 40. However, one of the interfering factors of CPAP therapy compliance is the fact that the sleep apnea patient P 120 is chronically fatigued because of lack of sleep due to his/her sleep apnea. As a result, the patient, frequently, is in bed 124, or in a wheelchair 146 or in a recliner chair, or on an air mattress, or any supportive substrate 124, or sleep medium, and turns on the CPAP device 10 with intentions to use the CPAP device 10 for treatment, after reading or watching t.v. but falls asleep before the patient P 120 lodges the CPAP mask 40 onto nose and mouth. The effectiveness of the CPAP treatment for the sleep apnea patient P 120 is obviously diminished if the CPAP mask 40 is not initially lodged onto the patient's P 120 nose and mouth. If a patient P 120 is not alerted to the event of failure to initially lodge the mask then treatment for sleep apnea is, obviously, compromised.

Therefore, it is preferred that the CPAP compliance notification apparatus 50 includes a patient occupancy mat 30 connected therein which triggers the CPAP device 10 to switch automatically to the "on mode" when a patient P 120 is occupied on the patient occupancy mat 30 while in bed 124 in simultaneous consideration to the patient occupancy mat 30 automatically starting the timer 60 to start counting down to the assigned time delay off-time limit t, because the patient P 120 may fall asleep before he/she turns on the CPAP device 10 or turns on the timer 60 due to fatigue, or the patient simply forgets to turn on the CPAP device 10 or the timer 60 and, consequently, the patient P 120 does not receive his/her necessary prescribed CPAP therapy.

Similarly, it is preferred that the CPAP compliance notification apparatus 50 includes a patient occupancy mat 30 connected therein which triggers the CPAP device 10 to switch automatically to the "off mode" when the patient P 120 vacates his/her bed and dislodges his/her CPAP mask 40 and in simultaneous consideration automatically turns off the timer 60 in case the patient inadvertently forgets to do so.

In the scenario of use of the CPAP compliance and notification apparatus 50 the patient P 120 positions the patient occupancy mat 30 having a weight pressure sensor 32 approximate to the supportive substrate 124, for example, the mattress of the bed 122, a bed 122, as illustrated in FIGS. 7-8, or a wheel chair 146, as illustrated in FIG. 9. The patient P 120 pre-selects the assigned time delay off-time limit t and presets the timer 60 of the one or more timers 60 to the selected assigned time delay off-time limit t by programming one or more of the timers 60 of the programmable logic controller 200 at the patient's P 120 preferred assigned time delay off-time limit t.

As mentioned above, a known patient preference is to read or watch t.v. before the patient P 120 lodges his CPAP mask 40 to receive his/her continuous positive air pressure treatment during the subsequent sleep cycle. The patient P 120 can select the time delay off-time of 30 minutes $t^2$ and accordingly set the timer 60. Accordingly, the patient P 120 selects a time delay off-time of 30 minutes which means that the patient P 120 is provided with a 30 minute $t^2$ time limit within which he/she should lodge his/her CPAP mask 40, and in the event the patient P 120 fails to comply and lodge his/her CPAP mask 40 the buzzer 61 will sound the audible alarm to alert the patient P 120 to comply and lodge his/her CPAP mask 40 so that the patient P 120 receives the prescribed continuous positive air pressure treatment.

The patient occupancy mat 30 including the weight pressure sensor 32 is placed approximate to the patient's bed mattress 124 such that when the patient P 120 occupies the bed mattress 124 the weight pressure sensor 32 detects the change in weight pressure as a result of the patient's P's 120 weight upon the patient occupancy mat 30. Upon the patient occupying the bed mattress 124 having a patient occupancy mat 30 approximate to the bed mattress 124 the weight pressure sensor 32 detects a change in weight pressure. Accordingly, the weight pressure sensor switch SW1 35 closes generating weight pressure sensor signal S1 wherewith a leading edge of the weight pressure sensor signal S1 fires the solenoid 94 and accordingly powering the CPAP device 10 immediately automatically to start and accordingly the flow generator 18 delivers continuous positive air pressure channeled through the patient's P's 120 CPAP hose 20 and to the patient's P 120 CPAP mask 40.

The weight pressure sensor 32 and in simultaneous consideration the air pressure sensor 84 continues to detect weight pressure changes and air pressure changes, respectively. In the event, the patient P 120 remains occupied on the patient occupancy mat 30 and accordingly the weight pressure sensor switch SW1 35 remains closed, and in simultaneous consideration the patient's P's 120 CPAP mask 40 remains on his/her nose and mouth during a period of awake time, or remains on his/her nose and mouth throughout a period of sleep time, or, more particularly, during the night time sleep cycle, and accordingly the air pressure sensor switch SW2 86 remains closed, the patient P 120 is in compliance, and in simultaneous consideration the timer-output 72 opens and accordingly the buzzer 61 will not sound the audible alarm because there is no voltage to the buzzer 61 and particularly because there is no need to alert the patient P 120 and, accordingly, the patient P 120 receives the prescribed continuous positive air pressure therapy during the sleep cycle.

The weight pressure sensor 32 continues to detect the weight pressure of the patient P 120 indicative of the patient's P's 120 presence on the patient occupancy mat 30. Thus, at the end of the sleep cycle or in the event for another reason the patient P 120 vacates the bed 124 and accordingly when patient P 120 removes his/her mask 40 and vacates the patient occupancy mat 30 accordingly the weight pressure sensor 32 detects the change in weight pressure due to the absence of the patient P 120. Accordingly the weight pressure sensor switch SW1 35 opens powering the CPAP device 10 to be placed in the off-mode, and in simultaneous consideration the timer 60 automatically turns off and stops counting down to the pre-assigned time delay off time.

In detail, when the patient P 120 vacates the patient occupancy mat 30, the weight pressure sensor switch SW1 35 opens interrupting the incoming weight pressure sensor signal S1 providing zero voltage. In addition, the patient P 120 removes his/her CPAP mask 40 and accordingly the air pressure sensor switch SW2 86 opens causing zero voltage. Accordingly, the trailing edge of signal S1 fires powering accordingly the CPAP device 10 is powered to the off-mode via the solenoid 94 such that the CPAP flow generator 18 ceases delivery of the continuous positive air flow channeled through the CPAP hose 20 to the patient's P CPAP mask 40 for treatment of his/her sleep apnea, and in simultaneous consideration the timer 60 stops counting to time delay off time $t^1$.

The CPAP compliance notification apparatus 50 to deliver a CPAP treatment to the patient repeats when the patient P 120 re-occupies the patient occupancy mat 30 including the weight pressure sensor 32 and accordingly the CPAP device 10 powers to the on-mode to deliver the continuous positive air pressure and the timer 60 restarts. The patient P 120 in compliance lodges his/her CPAP mask 40 sealed upon his nose and mouth to receive the prescribed continuous positive air pressure in his/her airways while awake or asleep.

In another scenario, the patient P 120 is awake and reading or watching t.v. in bed 120 and accordingly occupies the patient occupancy mat 30 including the weight pressure sensor 32 and the patient P 120 fails to initially lodge his/her mask because he/she has fallen asleep, perhaps, because of fatigue characteristic of sleep apnea patients, and consequently, does not initially lodge his/her CPAP mask 40. The patient P 120 is non-compliant and will not receive the necessary prescribed CPAP therapy. In an embodiment of the CPAP compliance notification apparatus 50, the CPAP compliance notification apparatus 50 operates to notify the patient P 120 by means of the audible alarm of the buzzer 61 to initially lodge his/her CPAP mask 40 when the patient P 120 has fallen asleep and has failed to initially lodge his/her CPAP mask 40.

In this exemplary embodiment of the CPAP compliance notification apparatus 50, the patient P 120 assigns the time delay off-time t and presets the programmable logic controller 200 with the timer 60 to the assigned time delay off-time t at the preferred time delay off time t. As mentioned above, a known patient P 120 preference is to read or watch t.v. before the patient P 120 lodges his CPAP mask 40 to receive his/her continuous positive air pressure treatment during the subsequent sleep cycle.

Thus, the patient P 120 can assign the time delay off-time of 30 minutes $t^2$. Accordingly, the patient P 120 selects the time delay off-time of 30 minutes $t^2$ which means that the patient P 120 is provided with a 30 minute $t^2$ time limit within which he/she can lodge his/her CPAP mask 40 such that in the event the patient P 120 fails to comply and lodge his/her CPAP mask 40 sealed upon his/her nose and mouth within the time limit of 30 minutes $t^2$ the buzzer 61 will sound the audible alarm to alert the patient P 120 to comply and lodge his/her CPAP mask 40 so that the patient P 120 receives the prescribed continuous positive air pressure treatment.

In this exemplary scenario, the patient P 120 does not comply, perhaps because he/she fell asleep, or simply became distracted and forgot, and the patient P 120 does not initially lodge his/her CPAP mask 40 on his/her nose and mouth, within the 30 minute time delay off time $t^2$ and accordingly the buzzer 60 will sound to alert the patient P 120 to lodge his/her CPAP mask 40 so that the patient P 120 can lodge his/her CPAP mask 40 and receive the prescribed continuous positive air pressure therapy.

Immediately, thereafter the buzzer 61 sounds the audible alarm the patient P 120 can press the reset button 90 button, as shown in FIG. 9, or in the preferred embodiment shown in FIGS. 5-8, press the reset text display 210$^2$ of the touch screen 208 of the user interface 206 to stop the buzzer 61 audible alarm.

In detail, the patient occupancy mat 30 including the patient occupancy sensor 32 is placed approximate to the patient's bed mattress 122 such that when the patient P 120 occupies the bed mattress 122 the patient occupancy sensor 32 detects the change in weight pressure indicative of the patient's P's 120 weight upon the patient occupancy mat 30. Upon the patient occupying the bed mattress 122 having a patient occupancy mat 30 approximate to the bed mattress 124 the patient occupancy sensor 32 detects a change in weight pressure. Accordingly, the weight pressure sensor switch SW1 86 closes generating the weight pressure sensor signal S1 wherewith the leading edge of weight pressure sensor signal S1 fires powering the solenoid 94 to extend the plunger 92 to press against the on/off button 12 of the CPAP device 10 and accordingly the conventional CPAP device 10 immediately automatically starts and the flow generator 18 delivers continuous positive air pressure channeled through the patient's CPAP hose 20 and to the patient's P's 120 CPAP mask 40.

In simultaneous consideration, the generated weight pressure sensor signal S1 is routed to power the timer 60, the timer 60 starts and immediately starts to count down to the pre-assigned time delay off time 30 minutes $t^2$.

The patient occupancy sensor 32 and in simultaneous consideration the air pressure sensor 84 continues to detect weight pressure and air pressure, respectively, indicative of the patient's P's 120 compliance. In the event, the patient P 120 remains occupied on the patient occupancy mat 30 and in the event the patient P 120 fails to initially lodge his/her CPAP mask 40 on his/her nose and mouth within the end limit of the 30 minute time delay off-time $t^2$ the air pressure sensor switch 86 opens. In simultaneous communication, the timer-output 72 closes and the buzzer 61 will sound the audible alarm to alert the patient P 120 to comply and lodge his/her CPAP mask 40 so that the patient P 120 is in compliance and receive the prescribed continuous positive air pressure to treat his/her sleep apnea if the patient does not replace his/her mask before the assigned time delay off-time $t^2$.

The patient P 120 can also set the timer to 30 minutes $t^2$ if he/she chooses to not be alerted for by the buzzer 61 for at least 30 minutes in the event the CPAP mask 40 is disrupted during a longer sleep cycle during the night, for example for 5-8 hours. The buzzer 61 is sounded to alert the patient P 120 when the patient's P's 120 CPAP mask 40 becomes dislodged from his or her nose and mouth, or the patient's P's 120 CPAP mask 40 leaks, or if the patient P's 120 does not re-lodge or adjust his or her CPAP mask 40 within the end limit of the time delay off-time of 30 minutes $t^2$. In this scenario, the patient P's 120 has more time to detect the CPAP mask 40 has become dislodged and perhaps re-lodge the CPAP mask 40 him/herself before the buzzer 61 sounds the audible alarm without disturbing others around him/her.

The buzzer 61 can issue an audible sound that has sufficient volume to alert the sleeping patient P 120. When the buzzer 61 is sounded the sleeping patient P 120 is alerted to re-lodge his/her CPAP mask 40, and in simultaneous consideration the timer 60 has stopped and in simultaneous consideration the CPAP device 10 remains in the on-mode.

Immediately thereafter, the patient P 120 silences the buzzer 61 by pressing the reset feature, reset feature, reset text display 210$^2$ such that the plunger 92 directly pushes down against the CPAP device 10 start/off button 12, and accordingly the CPAP device 10 is shut off, and the audible alarm of the buzzer 61 is silenced, and the timer 60 resets and restarts counting to time delay off-time 30 minutes $t^2$.

Accordingly, because the patient P 120 remains occupied on the patient occupancy mat 30 the weight pressure sensor switch SW1 35 is closed providing voltage the timer and the CPAP device 10 starts automatically and in simultaneous consideration the timer 60 restarts because a timer output closes providing voltage to the timer.

In an exemplary scenario, the patient P 120 occupies the patient occupancy mat 30 for example, by getting into bed 122 having a patient occupancy mat 30 positioned approximate to the bed mattress 122, the patient P 120 correctly lodges his/her CPAP mask 40, falls asleep, and during the CPAP treatment the CPAP mask 40 is dislodged or leaks.

In another scenario of the embodiment of the disclosure, because the sleeping patient's P's 120 CPAP mask 40 has become unsealed from the patient's P's 120 face and has dislodged the patient P 120 is now non-compliant and will not receive the necessary prescribed CPAP therapy.

In the exemplary embodiment, of the CPAP compliance notification apparatus 50, the CPAP compliance notification apparatus operates 50 to notify the sleeping patient P 120 by means of the audible alarm of the buzzer 60 to re-lodge his/her CPAP mask 40 when his/her CPAP mask 40 has dislodged or the CPAP mask 40 seal is leaking positive air pressure and the patient P 120 has failed to re-lodge his/her mask before the end limit of the time delay off-time t.

In the exemplary embodiment of the CPAP compliance notification apparatus 50, the patient P 120 pre-assigns the time delay off-time t. In this embodiment, the patient P 120 is in bed 124 and implements the CPAP compliance notification apparatus 50 so that the patient P 120 while the patient P 120 is asleep can be notified within a short time that his/her CPAP mask 40 has dislodged or is leaking.

Thus, the patient P 120 can select the assigned time delay off-time limit of 30 seconds $t^1$ so that the patient P 120 can be alerted by the buzzer's 61 audible alarm from his/her sleep cycle within the 30 seconds time delay off-time $t^1$ so that the patient P 120 can re-lodge his/her CPAP mask 40 and accordingly resume the benefit of the continuous positive air pressure therapy without a prolonged delay.

Accordingly, the patient P 120 selected the assiged time delay off-time of 30 seconds $t^1$ which means that the patient P 120 is provided with a 30 seconds $t^1$ time limit within which he/she should can lodge his/her CPAP mask 40, and in the event the patient P 120 fails to comply and lodge his/her CPAP mask 40 within the time limit of 30 seconds $t^1$ the buzzer 61 will sound the audible alarm to alert the sleeping patient P 120 to comply and re-lodge his/her CPAP mask 40 so that the patient P 120 can resume the prescribed continuous positive air pressure treatment throughout his/her sleep cycle.

As mentioned above, the buzzer 60 can issue an audible sound that has sufficient volume to alert an awake patient P 120, and/or a sleeping patient P 120. The audible alarm of the buzzer 60 is sounded in the event the patient P 120 does not re-lodge his/he CPAP mask or adjust his or her CPAP mask before the preferred pre-set time limit of the time delay off-time 30 seconds $t^1$. When the buzzer 60 is sounded the sleeping patient P 120 is alerted to re-lodge his/her CPAP mask 40, and in simultaneous consideration the timer 60 has stopped and in simultaneous consideration the CPAP device 10 remains in the on-mode and the flow of continuous positive air pressure continues. Therefore, the embodiment requires the patient P 120 to press the reset button 90, as shown in FIG. 9, or the resest feature, the reset text display $210^2$, as shown in FIGS. 5A, and 7-8 so that the audible alarm of the buzzer is silenced, the CPAP device 10 remains in the on-mode because the patient P 120 remains on the patient occupancy mat 30, and accordingly the timer restarts counting down to the assigned time delay off-time limit 30 seconds $t^1$. Thereafter, the patient P 120 can re-lodge his/her CPAP mask 40 to comply and lodge his/her CPAP mask 40 and resume his/her CPAP therapy.

Moreover, in the event the patient P 120 presses the reset feature, the reset button 90, as shown in FIG. 9, positioned immediately superior to the solenoid 94 such that the plunger 92 directly pushes down against the CPAP on/off button 12, the CPAP device 10 is shut off, and the buzzer 61 is silenced, and the timer 60 resets and restarts counting to the assigned time delay off-time limit 30 seconds $t^1$.

Because the patient P 120 is still occupied on the patient occupancy mat 30 the weight pressure sensor 32 generates weight pressure sensor signal S1 and powers the weight pressure sensor switch SW1 35 to remain close and accordingly the CPAP device 10 remains in the on-mode and in simultaneous consideration the timer 60 restarts automatically.

In another exemplary scenario, the patient P 120 occupies the patient occupancy mat 30 including the weight pressure sensor 32 and shortly thereafter vacates the patient occupancy mat 30 for a period of time, and subsequently returns to the patient occupancy mat 30. In one scenario, the patient P 120 may fall out of bed 122.

Therefore, the CPAP compliance notification apparatus 50 is configured to maintain the CPAP device 10 in the on-mode so that the continuous positive air pressure continues to be delivered through the CPAP hose 20 and to the CPAP mask 40 of the patient P 120.

The CPAP compliance notification apparatus 50, prior to the patient P 120 occupying the patient occupancy mat 30 and prior to receiving his/her continuous positive air pressure therapy for sleep apnea, the patient P 120 can select the time delay off-time of 30 minutes $t^2$ and program the timer of the one or more timers 60 of the programmable logic controller 200. Accordingly, the patient P 120 can select the assigned time delay off-time limit of 30 minutes $t^2$ which means that the patient P 120 is provided with a 30 minute $t^2$ time limit within which he/she should return to bed 122 such that in the event the patient P 120 fails to comply and return on the patient occupancy mat 30 the buzzer 61 will sound the audible alarm to alert the patient P 120 to comply and return to the patient occupancy mat 30 so that the patient P 120 receives the prescribed continuous positive air pressure treatment.

Attention will be now made to FIG. 10 illustrating a schematic of a CPAP compliance notification method 150 of the operations to be performed for implementing and using a CPAP compliance notification apparatus 50, as shown in reference to FIGS. 5A-9, and disclosed in detail above, comprises a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, and together with a patient P 120, to control parameters of the CPAP compliance notification apparatus 50 in implementing a compliant CPAP treatment to the patient P 120 configured for use with a conventional known CPAP device 10, a CPAP hose 20, and a CPAP mask 40 for the treatment of a patient P 120 with a sleep apnea condition in accordance with an embodiment of the disclosure.

Particularly, at step 151 the patient P 120 positions the patient occupancy mat 30 having a patient occupancy sensor 32 approximate to the supportive substrate 124, for example, the mattress of the bed 122, or a wheel chair 146.

At step 152 the patient P 120 can pre-assign the time delay off-time t and presets the timer 60 to the selected time delay off-time t by programming the programmable logic controller 200. The timer 60 can be set to time delay off-time t of approximately 30 minutes $t^2$ or 30 seconds $t^1$. As one skilled in the art knows the time delay off-time t can be configured to a variety of time delay off-times t. In this embodiment, the patient can assign the time delay off-time to be 30 minutes $t^2$.

At step 154 the patient P 120 laying down or sitting on the patient occupancy mat 30 and accordingly generating weight pressure sensor signal S1 causing the weight pressure sensor switch 35 to close at step 155 in simultaneous consideration at step 156 causing the CPAP device 10 to start automatically and in simultaneous consideration at step 158 causing the timer 60 to automatically start to count down to the time delay off-time t of approximately 30 minutes $t^2$.

At step 160 the patient P 120 initially lodging his/her CPAP mask 40 within the end limit of the 30 minute $t^2$ time delay off-time t. Accordingly, causing the air pressure sensor switch SW2 86 to close 162 and in simultaneous consideration causing the timer-output 72 to open providing zero voltage to the buzzer 61 and accordingly at step 165 the buzzer 60 does not sound the audible alarm in the event the patient P 120 manages at step 164 to maintain his/her CPAP mask 40 sealed during the subsequent sleep cycle.

At step 166 the patient P 120 can restfully sleep through the sleep cycle. At step 167 the patient P 120 awakens and accordingly dislodging his/her CPAP mask 40 and at step 168 accordingly causing the air pressure sensor switch 35 opens at step 169. Subsequently, at step 170 the patient vacating the patient occupancy mat 30 and accordingly causing the weight pressure sensor switch 35 opens at step 172 and in simultaneous consideration causing the CPAP device 10 to power to the off-mode at step 174 and in simultaneous consideration causing the timer 60 to stop counting down at step to the time-delay off time t of approximately 30 minutes $t^2$, at step 176. Accordingly, the patient P 120 can choose not to go back to sleep on the patient occupancy mat 30 at step 178. After the execution of step 178 the method 150 implementing the compliance notification apparatus 50 may end.

In the event, at step 160 the patient P 120 fails to lodge or re-lodge his/her CPAP mask 40 within the pre-assigned delay time t, $t^1$–30 seconds, or $t^2$–30 minutes the air pressure sensor switch 86 opens at step 180 and accordingly providing zero voltage the buzzer 61 will sound the audible alarm at step 182 because the timer-output 72 closes providing voltage at step 184 accordingly the CPAP device 10 remains in the on-mode because the patient P 120 remains on the patient occupancy mat 30.

The patient P 120 can press the reset button 90, as shown in FIG. 9, or press the reset feature 210², the reset text display 210² of the user interface 206 of the compliance notification controller unit 52, as shown in FIGS. 5A, 7-8, P 120 at step 186 and accordingly causing the buzzer 61 from sounding at step 190, in simultaneous communication the CPAP device 10 is powered to remain in the on-mode at step 188 and accordingly the timer 60 restarts at step 158 and the patient P 120 can be engaged in the method 150 again.

In another embodiment of the invention, the CPAP compliance notification apparatus 50 further comprises a CPAP device 10, a CPAP hose 20 with the air pressure tube adapter 88 to adapt an air pressure tube 80, and a CPAP mask 40.

Even if reference has been made to the compliance controller unit, the concepts of the disclosure can be applied to other types of controller units, such as non-volatile memory fields, computers with one or more processors, programmable logic controller with one or more microprocessors.

Moreover, even if in the description the compliance notification controller unit circuitry is connected to a respective contact, the concepts of the invention apply to different arrangements; for example, the contact array may be provided with one or more types of time delay relays, or one or more sensors, one or more programmable logic controllers having one or more processors, or a computer.

As described in more detail below, the aspects described herein may accommodate various alternatives. For example, in an embodiment of the disclosure, a CPAP compliance notification system 300 is disclosed, as shown in FIGS. 11A-11B which is a functional diagram of a CPAP compliance notification system 300 in accordance with aspects of the subject matter of the disclosure.

In another embodiment of the disclosure the CPAP compliance notification apparatus 50 is implemented with a programmable controller unit 200. The disclosure of this embodiment is described using like numbers as in the previously described embodiment of the CPAP compliance notification apparatus 50 and the programmable logic controller 200 for continuity.

Figure 3:
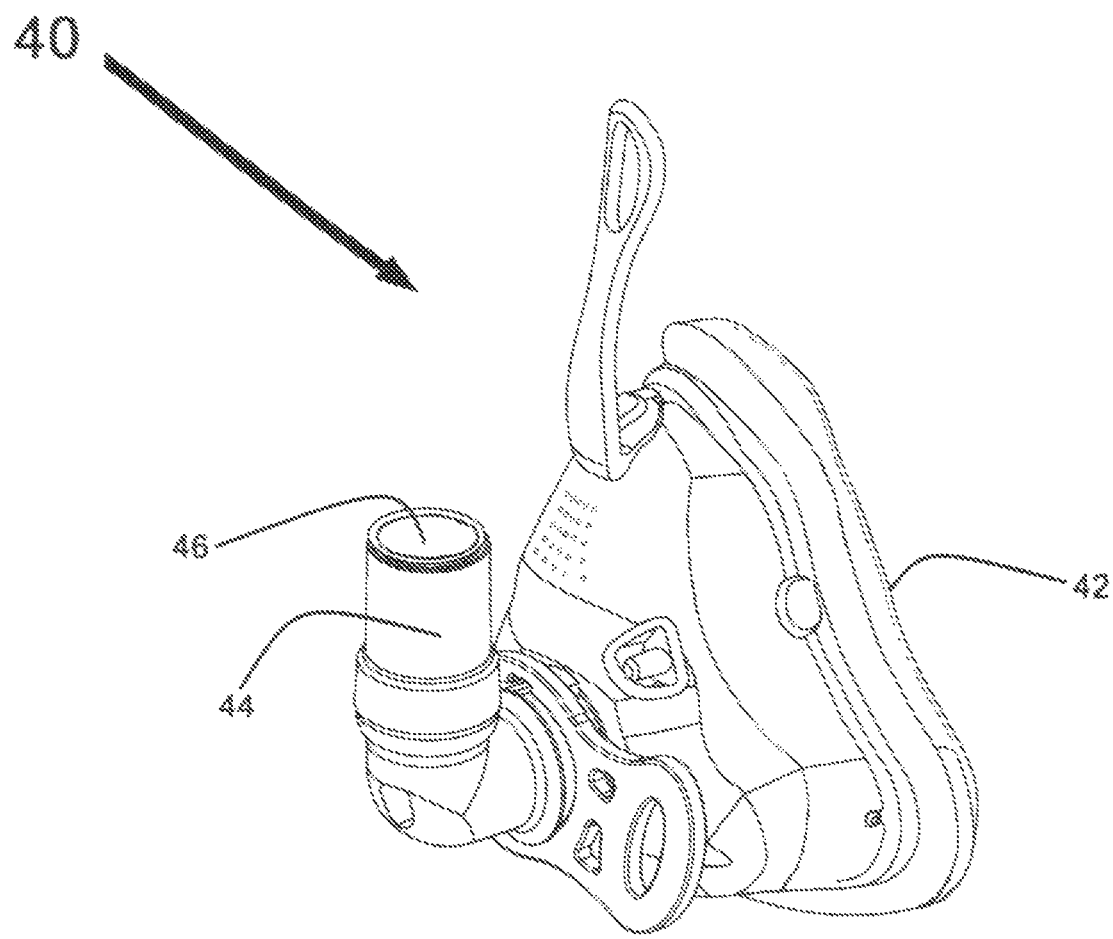
FIG. 3 shows a known conventional continuous positive air pressure mask (CPAP mask), a facial CPAP mask, according to an embodiment of the present disclosure.

In the embodiment of the disclosure of the subject matter the CPAP compliance notification apparatus 50, including the programmable logic controller 200, is shown in FIG. 5A-6B, for use with a CPAP device 10, as shown in FIG. 1A-1B having the flow generator 18, the CPAP hose 20, as shown in FIG. 2, and the CPAP mask 40, as shown in FIG. 3. The CPAP compliance notification apparatus 50, comprises a comprises a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, a programmable logic controller 200 and together with a patient P 120, to control parameters of the CPAP compliance notification apparatus 50 in implementing a compliant CPAP treatment to the patient P 120, as shown in FIGS. 5A-6B and FIGS. 7-9.

The patient occupancy mat 30 includes a weight pressure sensor 32 including a weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

The air pressure sensor 84 is positioned within the compliance notification controller unit 52, wherein the air pressure sensor 84 including an air pressure sensor switch SW2 86 therein is positioned remotely from an airway of the patient P 120 and remotely from a blower outlet 18¹ of the flow generator 18 of the CPAP device 10, wherein the air pressure sensor 84 is operable to generate an air pressure sensor signal S2 triggered at the patient's P 120 lodgment of the CPAP mask 40 on the patient's P 120 face, wherein the air pressure sensor signal S2 is interrupted upon the patient's P 120 dislodgement of the CPAP mask 40 from the patient's P 120 face.

The air pressure tube 80, as shown in FIG. 5B-5C having an interior hollow channel limited by an open first end 80$^1$ having the first opening 83 can be releasable connected to the CPAP hose 20 by means of the air pressure tube adapter 88 proximate to the flow generator 18 and a second end 80$^2$ having the second opening 85 positioned releaseably connected to the air pressure sensor 84 housed within the compliance notification controller unit 52. The air pressure tube adapter 88 is the tube extender 88 having a first opening sized to be flush with the first end 80$^1$ opening of the air pressure tube 80 and an opposing second opening sized to be flush with an inlet on the CPAP hose 20, the inlet proximate to the flow generator 18. The second open end 80$^2$ of the air pressure tube communicates with an inlet port of the air pressure sensor 84.

In this exemplary embodiment, the solenoid 94 includes a plunger 92 coextensive with an anterior portion of the solenoid 94 and does not include the reset button 90.

The compliance notification controller unit 52, as shown in FIGS. 5A-6B includes the housing 53 operable to maintain the compliance notification controller unit 52 components in one location proximate to each other. The compliance notification controller unit 52 components, including a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, a programmable logic controller 200 and together with a patient P 120, to control parameters of the CPAP compliance notification apparatus 50 in implementing a compliant CPAP treatment to the patient P 120.

The one or more ports 78, 68, and 66, an electrical supply socket 69 of the type suitable for receiving a universal power cord plug 63 operable for supplying electrical power supply to the compliance notification controller unit 52; one or more DC power sources 110 operable to direct electrical power; a rechargeable battery 202; the mobile communication device docking station with charger 204; a buzzer 61; the buzzer 61 including a timer-output 72 adapted and operable to direct an audible alarm to the patient P 120, the audible alarm having sufficient intensity to alert the patient P 120, whereby the buzzer 61 is adapted and operable to alert the patient P 120 during the patient's P 120 occupancy on the patient occupancy mat 30 of the interruption in air pressure at an interior channel of the air pressure tube 80 indicative that the patient P 120 has not lodged his/her CPAP mask 40 within one or more assigned time delay off-time(s). In addition, the buzzer can alert the P 120 in the event the P 120 has not occupied or re-occupied the patient occupancy mat 30 within the end limit of a time delay-off time t of one or more timers 61.

The compliance notification controller unit 52, also, includes a user interface 206 including a touch screen 208 which includes one or more text displays 210. A first text display 210$^1$ of the one or more text displays 210 includes an on/off text display 210$^1$, wherein the on/off text display 210$^1$ being adapted and operable when pressed to direct an "on-mode" and an "off-mode" of the CPAP device 10 via contact of the solenoid 94 plunger 92 against an on/off button of the CPAP device 10.

A second text display 210$^2$ of the one or more text displays 210 includes a reset text display 210$^2$, wherein the reset text display 210$^2$ being adapted and operable when pressed to direct an audible alarm of the buzzer 61 to turn off and to restart the timer 60 of the one or more timers 61.

A third text display 210$^3$ of the one or more text displays 210 includes a snooze text display 210$^3$, wherein the snooze text display 210$^3$ being adapted and operable when pressed to direct one or more timers 60 within the programmable logic controller 200 to delay the buzzer 61.

According to the embodiment of the CPAP compliance notification system 300, the programmable logic controller 200 is configured and adapted to implement parameters to perform a methodology of a compliant continuous positive airway pressure treatment for the patient P 120, wherein the programmable logic controller 200, comprising one or more microprocessors is configured to receive instructions to implement a method of a CPAP treatment for the patient P 120, one or more timers 60, receive digital input data, receive analog input data; transmit digital output data; wherein digital input data includes identifying, parameters of the weight pressure signal S1, the weight pressure sensor switch SW1 35, and parameters of the one or more timers 60, wherein analog input data includes identifying parameters of the air pressure sensor signal S2, the air pressure sensor switch SW2 86, and wherein the digital output includes identifying parameters of the buzzer 61, the solenoid 94, and the user interface 206.

The CPAP compliance notification apparatus 50, in accordance to the disclosure, the patient occupancy mat 30 is positioned approximate to the supportive substrate 124. The supportive substrate 124 comprises any one of the group comprising, bed mattress 122 or bed 122, wheelchair 146, recliner chair, air mattress, any sleep medium, any sitting medium, or any supportive substrate 124 including, as mentioned above, any one of the supportive substrates 124 contemplated in other embodiments, sofa, couch, cushion, seat, chair, recliner chair, arm chair, infant crib, high chair, baby seat, vehicle car seat, an infant car seat, a carriage, a booster seat, seat on an airplane, a seat on a train, or a support substrate associated with an ambulance, air mattress, any sleep medium, any sitting medium, or any supportive substrate 124.

The weight pressure sensor switch SW1 35 of the weight pressure sensor 32 is adapted and operative to power to a closed position via the programmable logic controller's 200 derivation of the weight pressure sensor signal S1 generated at the patient P 120 occupying the patient occupancy mat 30, whereby the weight pressure sensor switch SW1 35 in the closed position operably causes the CPAP device 10 to power to the on-mode so that the flow generator 18 delivers continuous positive airway pressure channeled through the CPAP hose 20 to the patient's CPAP mask 40, and in simultaneous communication operably causes the timer 60 to begin counting down to the one or more assigned time delay off-time(s) t.

The weight pressure sensor switch SW1 35 of the weight pressure sensor 32 is adapted and operative to power to the open position via the programmable logic controller's 200 derivation of the weight pressure sensor signal S1 being zero generated at the patient P 120 vacating the patient occupancy mat 30, and in simultaneous communication the air pressure sensor switch SW2 86 of the air pressure sensor 84 is adapted and operative to power to the open position via the programmable logic controller's 200 derivation of the air pressure sensor signal S2 being interrupted indicative of failure to lodge the patient's CPAP mask 40 onto the patient's P 120 face, or the dislodgement of the patient's P 120 CPAP mask 40, whereby the weight pressure sensor switch SW1 35 in the open position and in simultaneous communication the air pressure sensor switch SW2 86 in the open position operably causes the CPAP device 10 to power to the off-mode via the solenoid 94 so that the flow generator 18 ceases to deliver continuous positive airway pressure channeled through the CPAP hose 20 to the patient's CPAP mask 40, and in simultaneous communication operably causes the timer 60 to stop counting down to the one or more of the assigned time delay off-time(s) t.

The weight pressure sensor switch SW1 35 of the weight pressure sensor 32 is adapted and operative to power to the closed position via the programmable logic controller's 200 derivation of the weight pressure sensor signal S1 being generated at the patient P 120 occupying the patient occupancy mat 30, and in simultaneous communication the air pressure sensor switch SW2 86 of the air pressure sensor 84 is adapted and operative to power to the closed position via the programmable logic controller's 200 derivation of the air pressure sensor signal S2 being generated indicative of the lodgment of the patient's P 120 CPAP mask 40, whereby the weight pressure sensor switch SW1 35 in the closed position and in simultaneous communication the air pressure sensor switch SW2 86 in the closed position operably causes the CPAP device 10 to be maintained in the on-mode and in simultaneous consideration operably causes the timer 60 to stop counting down toward the one or more assigned time delay off-time(s) t and in simultaneous communication operably causes the timer-output 72 to open causing the buzzer 61 to be inoperable.

The weight pressure sensor switch SW1 35 of the weight pressure sensor 32 is adapted and operative to power to the closed position via the programmable logic controller's 200 derivation of the weight pressure sensor signal S1 being generated at the patient P 120 occupying the patient occupancy mat 30, and in simultaneous communication with the programmable logic controller 200 the air pressure sensor includes the air pressure sensor switch SW2 86 which based on the air pressure sensor signal S2 being interrupted indicative of the patient P 120 failing to lodge his/her CPAP mask 40, or dislodgement of his/her CPAP mask 40, or a leak in his/her CPAP mask 40, powers to an open position which operably causes the timer 60 to start counting down toward the one or more assigned time delay off-time(s) t and in simultaneous communication operably causes the timer-output 72 to close causing the buzzer 61 to be operable and sound the audible alarm to alert the patient P 120 in the event the patient P 120 does not lodge his/her CPAP mask 40 before the one or more of the assigned time delay off-time(s) t.

The air pressure sensor switch SW2 86 of the air pressure sensor 84 is adapted and operative to power to the closed position via the programmable logic controller's 200 derivation of the air pressure sensor signal S2 being generated indicative of the lodgment of the patient's CPAP mask 40, and in simultaneous communication the weight pressure sensor switch SW1 35 of the weight pressure sensor 32 is adapted and operative to power to the open position via the programmable logic controller's 200 derivation of the weight pressure sensor signal S1 being zero generated at the patient P 120 vacating the patient occupancy mat 30, which operably causes the timer 60 to start counting down toward the one or more assigned time delay off-time(s) t and in simultaneous communication operably causes the timer-output 72 to close causing the buzzer 61 to be operable and sound the audible alarm to alert the patient P 120 in the event the patient P 120 does not occupy the patient occupancy mat 30 before the one or more of the assigned time delay off-time(s) t, and in simultaneous communication the CPAP device 10 is maintained in the on-mode so that the flow generator 18 continues to deliver continuous positive airway pressure channeled through the CPAP hose 20 to the patient's CPAP mask 40.

As shown in FIGS. 7-9, the solenoid 94 is aligned vertically superior to a CPAP device 10 on/off button 12, wherein the solenoid 94 is configured having a plunger 92 coextensive from an anterior portion of the solenoid 94 and operable so that when the on-off text display $210^1$ of the user interface 206 is pressed, the plunger 92 is depressed against the CPAP device 10 on/off button 12 causing the CPAP device 10 in the off-mode to power to the on-mode.

Similarly, the solenoid 94 being aligned vertically superior to a CPAP device 10 on/off button 12, and the solenoid 94 configured having the plunger 92 coextensive from the anterior portion of the solenoid 94 and operable such that when the on-off text display $210^1$ is pressed the plunger 92 is depressed against the CPAP device 10 on/off button 12 causing the CPAP device 10 in the on-mode to power to the off-mode.

In a scenario, wherein the patient P 120 is occupied on the patient occupancy mat 30 and the CPAP mask 40 is not lodged upon the patient's P 120 face within the one or more assigned time-delay off time(s) t in combination causes the weight pressure sensor switch SW1 35 to close and the air pressure sensor switch SW2 86 to open, respectively, and in simultaneous communication with the programmable logic controller 200 causes the timer-output 72 to close so that the buzzer 61 sounds the audible alarm to alert the patient P 120 to lodge his/her CPAP mask 40.

When the buzzer 61 sounds the audible alarm the patient P 120 can press the reset text display $210^2$ of the user interface 206 causing the timer-output 72 to open and the buzzer 61 sounding the alarm is silenced while the CPAP device 10 is maintained in the on-mode so that the flow generator 18 continues to deliver continuous positive airway pressure channeled through the CPAP hose 20 to the patient's CPAP mask 40 to the patient P 120 so that the patient P 120 receives the CPAP therapy treatment.

When the patient P 120 is occupied on the patient occupancy mat 30 and the CPAP mask 40 is lodged upon the patient's P 120 face within the one or more assigned time-delay off time(s) t in combination causes the weight pressure switch SW1 35 to close and the air pressure sensor switch SW2 86 to close, respectively, and in simultaneous communication with the programmable logic controller 200 causes the timer-output 72 to open so that the buzzer 61 does not sound the audible alarm.

As shown in FIG. 5A, the solenoid 94 is supported by a rigid vertical arm 96 having a first horizontal arm $97^1$ and a second horizontal arm $97^2$, the first horizontal arm $97^1$ and the second horizontal arm $97^2$ being maneuverable via a thumb nut 95 and the rigid vertical arm 96 and the first horizontal arm $97^1$ manipulated by a first thumb nut 216.

The CPAP compliance notification apparatus 50 exemplified can further comprise a humidifier.

In another embodiment of the disclosure, a CPAP compliance notification system 300 is described. The CPAP compliance notification system 300 is shown in FIGS. 11A-11C. The CPAP compliance notification system 300 comprises one or more computer implemented programmable logic controller(s) 200, each programmable logic controller 200 having one or more microprocessors, wherein the one or more microprocessors are configured to receive instructions to provide a CPAP treatment to the patient P 120 identifying components. The components including a CPAP compliance notification apparatus 50 for use with a CPAP device 10 having a flow generator 18, a CPAP hose 20, a CPAP mask 40.

The CPAP compliance notification system 300 includes to provide the CPAP device 10 having a flow generator 18, provide the CPAP hose 20, provide the CPAP mask 40, provide the CPAP compliance notification apparatus 50, wherein the embodiment of the disclosure of the subject matter the CPAP compliance notification apparatus 50, comprises a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, a programmable logic controller 200 and together with a patient P 120, to control parameters of the CPAP compliance notification apparatus 50 in implementing a compliant CPAP treatment to the patient P 120.

The CPAP compliance notification apparatus 50, comprises the patient occupancy mat 30 having a weight pressure sensor 32 including a weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

The air pressure sensor 84 is positioned in the compliance notificaton controller unit 52, the air pressure sensor 84 having an air pressure sensor switch SW2 86 therein positioned remotely from an airway of the patient P 120 and remotely from a blower outlet 18$^1$ of the flow generator 18 of the CPAP device 10, wherein the air pressure sensor 84 is operable to generate the air pressure sensor signal S2 triggered at the patient's P 120 lodgment of the CPAP mask 40 on the patient's P 120 face, wherein the air pressure sensor signal S2 is interrupted upon the patient's P 120 dislodgement of the CPAP mask 40 from the patient's P 120 face.

The air pressure tube 80 having an interior hollow channel limited by an open first end 80$^1$ having the first opening 83 can be releasable connected to the CPAP hose 20 by means of the air pressure tube adapter 88 proximate to the flow generator 18 and a second end 80$^2$ having the second opening 85 positioned releaseably connected to the air pressure sensor 84 housed within the compliance notification controller unit 52. The air pressure tube adapter 88 is the tube extender 88 having a first opening sized to be flush with the first end 80$^1$ opening of the air pressure tube 80 and an opposing second opening sized to be flush with an inlet on the CPAP hose 20, the inlet proximate to the flow generator 18. The second open end 80$^2$ of the air pressure tube communicates with an inlet port of the air pressure sensor 84.

In this exemplary embodiment, as shown in FIGS. 5A, 7 and 8, the solenoid 94 includes a plunger 92 coextensive with an anterior portion of the solenoid 94 and does not include the reset button 90.

The compliance notification controller unit 52, includes the housing 53 operable to maintain the compliance notification controller unit 52 components in one location proximate to each other. The compliance notification controller unit 52 components, including one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, a programmable logic controller 200 and together with a patient P 120, to control parameters of the CPAP compliance notification apparatus 50 in implementing a compliant CPAP treatment to the patient P 120.

The one or more ports 78, 68, and 66, an electrical supply socket 69 of the type suitable for receiving a universal power cord plug 63 operable for supplying electrical power supply to the compliance notification controller unit 52; one or more DC power sources 110 operable to direct electrical power; a rechargeable battery 202; a mobile communication device docking station with charger 204; a buzzer 61; the buzzer 61 including a timer-output 72 adapted and operable to direct an audible alarm to the patient P 120, the audible alarm having sufficient intensity to alert the patient P 120, whereby the buzzer 61 is adapted and operable to alert the patient P 120 during the patient's P 120 occupancy on the patient occupancy mat 30 of the interruption in air pressure at an interior channel of the air pressure tube 80 indicative that the patient P 120 has not lodged his/her CPAP mask 40 within one or more assigned time delay off-time(s) t. The buzzer 61 is, also, adapted and operable to alert the patient P 120 in the event the patient P 120 vacates the patient occupancy mat 30 and does not re-occupy the patient occupancy mat 30 within one or more assigned time delay off-times t.

The user interface 206 including a touch screen 208 includes one or more text displays 210. A first text display 210$^1$ of the one or more text displays 210 includes an on/off text display 210$^1$, wherein the on/off text display 210$^1$ being adapted and operable when pressed to direct an "on-mode" and an "off-mode" of the CPAP device 10 via contact of the solenoid 94 plunger 92 against an on/off button of the CPAP device 10.

A second text display 210$^2$ of the one or more text displays 210 includes a reset text display 210$^2$, wherein the reset text display 210$^2$ being adapted and operable when pressed to direct an audible alarm of the buzzer 61 to turn off and to restart one or more timers 60.

A third text display 210$^3$ of the one or more text displays 210 includes a snooze text display 210$^3$, wherein the snooze text display 210$^3$ being adapted and operable when pressed to direct one or more timers 60 within the programmable logic controller 200 to delay the buzzer 61 and from sounding the audible alarm.

The programmable logic controller 200 of the CPAP compliance notification system 300 is configured and adapted to implement parameters to perform a methodology of a compliant continuous positive airway pressure treatment for the patient P 120, wherein the programmable logic controller 200, comprising one or more microprocessors is configured to receive instructions to implement a method of a CPAP treatment for the patient P 120, one or more timers 60, receive digital input data, receive analog input data; transmit digital output data; wherein digital input data includes identifying, parameters of the weight pressure sensor signal S1, the weight pressure sensor switch SW1 35, and parameters of the one or more timers 60, wherein analog input data includes identifying parameters of the air pressure sensor signal S2, the air pressure sensor switch SW2 86, and wherein the digital output data includes identifying parameters of the buzzer 61, the solenoid 94, and the user interface 206.

In addition, the CPAP compliance notification system 300, implementing the programmable logic controller 200 receives a first digital input data identifying the patient P 120 detected on the patient occupancy mat 30, the first digital input data including the weight pressure sensor signal S1 generated from the weight pressure sensor 32 integrally connected within the patient occupancy mat 30; derive the weight pressure sensor signal S1, wherein deriving the weight pressure sensor signal S1 includes causing the weight pressure sensor switch SW1 35 to close; receive a second digital input data, identifying the patient P 120 vacating the patient occupancy mat 30. The second digital input data including a weight pressure sensor signal S1 at zero generated from the weight pressure sensor 32 integrally connected within the patient occupancy mat 30.

Continuing, derive the weight pressure sensor signal S1, wherein deriving the weight pressure sensor signal S1 at zero includes causing the weight pressure sensor switch SW1 35 to open; use the closure of the weight pressure sensor switch SW1 35; transmit a first digital output data to the solenoid 94 including the closure of the weight pressure sensor switch SW1 35 to cause the CPAP device 10 to power to the on-mode via the solenoid 94 whereby the plunger 92 of the solenoid 94 presses against the on/off button 12 of the CPAP device 10 causing the flow generator 18 to deliver continuous positive airway pressure channeled through the CPAP hose 20 to the CPAP mask 40 to the patient P 120; receive a third digital input data to cause a timer 60 of the one or more timers 60 to start counting down an assigned delay off-time of the one or more assigned time delay off-time(s) t; receive a fourth digital input data to cause the timer 60 of the one or more timers 60 to stop counting down to the assigned delay off-time of the one or more assigned time-delay off time(s) 60; receive a first analog input data, the first analog input data identifying an air pressure within the air pressure tube 80 releasably attached to the air pressure sensor 84 and interconnected to the CPAP hose 20 proximate to a blower outlet 18$^1$ of the flow-generator 18 identifying the CPAP mask 40 detected lodged on the patient's P 120 face, the first analog input data including the air pressure sensor signal S2 generated from the air pressure sensor 84 disposed within the compliance notification controller unit 52; derive the air pressure sensor signal S2, wherein deriving the air pressure sensor signal S2 includes causing the air pressure sensor switch SW2 86 to close; receive a second analog input data, the second analog input data identifying an air pressure within the air pressure tube 80 proximate to the air pressure sensor 84 identifying the CPAP mask 40 detected dislodged from the patient's P 120 face, wherein the second analog input data including the air pressure sensor signal S2 generated from the air pressure sensor 84 disposed within the compliance notification controller unit 52 is interrupted; derive the air pressure sensor signal S2, wherein deriving the air pressure sensor signal S2 interrupted includes causing the air pressure sensor switch SW2 86 to open; derive the air pressure sensor signal S2, wherein deriving the air pressure sensor signal S2 at zero includes causing the air pressure sensor switch SW2 86 to open; receive a fifth digital input data identifying one or more assigned time-delay off time(s) t before the patient P 120 must comply and lodge his/her CPAP mask 40 sealing over his/her nose and mouth to prevent the buzzer 61 from sounding the audible alarm; receive a sixth digital input data identifying an assigned time delay off-time t of the one or more time delay off-time(s) t before the patient P 120 must comply and re-occupy the patient occupancy mat 30 after vacating the patient occupancy mat 30 to prevent the CPAP device 10 from powering to the off-mode; determine the closure of the weight pressure sensor switch SW1 35 on a comparison to the closure of the air pressure sensor switch SW2 86, wherein the determination of the closure of the weight pressure sensor switch SW1 35 and the closure of the air pressure sensor switch SW2 86 together causes the timer-output 72 to open and the timer 60 stops counting down to the end of one or more of the time delay-off times t; use the open timer-output 72; transmit a second digital output data to the solenoid 94 of the open timer-output 72 to cause the buzzer 61 not to sound the audible alarm; receive the second analog input data, the second analog input data identifying an air pressure within the air pressure tube 80 proximate to the air pressure sensor 84, identifying the CPAP mask 40 detected dislodged from the patient's P 120 face; the second analog input data including the air pressure sensor signal S2 generated from the air pressure sensor 84 disposed within the compliance notification controller unit 52 is interrupted; determine the closure of the weight pressure sensor switch SW1 35 on a comparison to the open air pressure sensor switch SW2 86, wherein the determination of the closure of the weight pressure sensor switch SW1 35 and the opening of the air pressure sensor switch SW2 86 together causes the timer-output 72 to close; use the closed timer-output 72; use the closed timer-output 72 to continue the one or more timers 60 to counting down to the one or more time delay off-times t; transmit a third digital output data to the solenoid 94 of the closed timer-output 72 to cause the buzzer 61 to sound the audible alarm at an end of the one or more assigned time-delay off time(s) t to alert the patient P 120 to lodge his/her CPAP mask 40; derive the fourth digital input data to cause the timer 60 of the one or more timers 60 to stop counting down to the one or more assigned time-delay off time(s) t; identify a reset feature, a reset text display 210$^2$, from the touch screen 208 of the compliance notification controller unit 52; trigger the reset feature, press the reset text display 210$^2$, transmit a fourth digital output data to the solenoid 94 identifying the reset feature, reset text display 210$^2$, is triggered; use the triggered reset feature, reset text display 210$^2$, so that the closed timer-output 72 is open; use the open timer-output 72; transmit the second digital output data to the solenoid 94 of the open timer-output 72 to cause the buzzer 61 not to sound the audible alarm so that the buzzer 61 is silenced; derive the third digital input data to cause a timer 60 of the one or more timers 60 to start counting down to the one or more assigned time-delay off time(s) t; resume the CPAP treatment for the patient P 120; receive the second digital input data, identifying the patient P 120 vacating the patient occupancy mat 30; the second digital input data including the weight pressure sensor signal S1 at zero generated from the weight pressure sensor 32 integrally connected within the patient occupancy mat 30; derive the weight pressure sensor signal S1, wherein deriving the weight pressure sensor signal S1 at zero includes causing the weight pressure sensor switch SW1 35 to open in simultaneous communication derive the air pressure sensor signal S2, wherein deriving first analog input data the air pressure sensor signal S2 includes causing the air pressure sensor switch SW2 to remain closed and in simultaneous communication the CPAP device 10 to be maintained in the on-mode so that the flow generator continues to deliver continuous positive airway pressure channeled through the CPAP hose 20 to the CPAP mask 40 to the patient P 120; use the open weight pressure sensor switch SW1 35 in simultaneous communication use the closed air pressure sensor switch SW2 86; determine the open weight pressure sensor switch SW1 35 on a comparison to the closed air pressure sensor switch SW2 86, wherein the determination of the open weight pressure sensor switch SW1 35 and the closed air pressure sensor switch SW2 86 together causes the timer-output 72 to open; receive the sixth digital input data identifying the assigned time-delay off time t of the one or more time-delay off time(s) t before the patient P 120 must comply and re-occupy the patient occupancy mat 30 after vacating the patient occupancy mat 30 to prevent the CPAP device 10 from powering to the off-mode; receive the third digital input data to cause the one or more timers 60 to continue to count down to the one or more time delay-off times t causing the timer-out 72 put to close, use the closed timer-output 72 so that the buzzer 61 sounds the audible alarm at the end of the one or more of the assigned time-delay off time(s) t to alert the patient P 120 to occupy the patient occupancy mat 30; receive the fourth digital input data to cause the timer 60 of the one or more timers 60 to stop counting down to the one or more assigned time-delay off time(s); transmit a fifth digital output data to the solenoid 94 of the closed timer-output 72 to cause the buzzer 61 to sound the alarm at an end of the one or more assigned time-delay off time(s) to alert the patient P 120 to reoccupy the patient occupancy mat 30; derive the fourth digital input data to cause the timer 60 of the one or more timers 60 to stop counting down to the one or more assigned time-delay off time(s) t; identify the reset feature from the compliance notification controller unit 52; trigger the reset feature 210$^2$, reset text display 210$^2$; transmit the fourth digital output data to the solenoid 94 identifying the reset feature, reset text display 210$^2$, is triggered; use the triggered reset feature 210$^2$, reset text display 210$^2$, so that the closed timer-output 72 is open; use the open timer-output 72; transmit the second digital output data to the solenoid 94 of the open timer-output 72 to cause the buzzer 61 not to sound the audible alarm so that the buzzer 61 is silenced; derive the third digital input data to cause a timer 60 of the one or more timers 60 to start counting down to the one or more assigned time-delay off time(s) t; resume the CPAP treatment for the patient P 120; receive the second digital input data, identifying the patient P 120 vacating the patient occupancy mat 30; the second digital input data including a weight pressure sensor signal S1 at zero generated from the weight pressure sensor 32 integrally connected within the patient occupancy mat 30; derive the weight pressure sensor signal S1, wherein deriving the weight pressure sensor signal S1 at zero includes causing the weight pressure sensor switch SW1 35 to open; receive the second analog input data, the second analog input data identifying an air pressure within the air pressure tube 80 interconnected to the CPAP hose 20 proximate to the blower outlet of the flow generator 18 identifying a CPAP mask 40 detected dislodged from the patient's P 120 face; derive the air pressure sensor signal S2; transmit to the solenoid 94 the air pressure sensor signal S2 at zero includes causing an air pressure sensor switch SW2 86 to open; use the open weight pressure sensor switch SW1 35 in simultaneous communication use the open air pressure sensor switch SW2 86; determine the open weight pressure sensor switch SW1 35 on a comparison to the open air pressure sensor switch SW2 86, wherein the determination of the open weight pressure sensor switch SW1 35 and the open air pressure sensor switch SW2 86 together causes the timer-output 72 to open; use the open weight pressure sensor switch SW1 35 in simultaneous communication use the open air pressure sensor switch SW2 86; use the sixth digital input data identifying the assigned time-delay off time t of the one or more time-delay off time(s) t before the patient P 120 must comply and re-occupy the patient occupancy mat 30 after vacating the patient occupancy mat 30 to prevent the CPAP device 10 from powering to the off-mode; transmit a sixth digital output data to the solenoid 94 to cause the CPAP device 94 to power to the off-mode via the solenoid 94 causing cessation of the flow generator to deliver continuous positive airway pressure channeled through the CPAP hose 20 to the CPAP mask 40 to the patient P 120; transmit the second digital output data to the solenoid 94 of the open timer-output 72 to cause the buzzer 61 not to sound the audible alarm so that the buzzer 61 is silenced; derive the fourth digital input data to cause the timer 60 of the one or more timers 60 to stop counting down to the one or more assigned time-delay off time(s) t; and end the CPAP treatment for the patient P 120.

In the exemplary embodiment of the disclosure, the CPAP compliance notification system 300, is disclosed wherein the one or more microprocessors are further configured to: receive data by a mobile communication device (not shown) having one or more microprocessors; wherein the mobile communication device is a cell phone (not shown); wherein the cell phone is maintained on a docking station 204, the docking station 204, as shown in FIGS. 5A and 6B, integrally machined into the compliance notification controller unit 52.

In another embodiment of the CPAP compliance notification apparatus 50, in accordance with the subject matter of the disclosure, the compliance notification controller unit 52 is integrally machined in the rectangular mounting platform 98 so that the solenoid 94 is coextensive with an exterior surface of the rectangular mounting platform 98, wherein the exterior surface of the rectangular mounting platform 98 includes one or more icons implementing a CPAP treatment for the patient, wherein the one or more icons are communicable with the programmable logic controller 200 housed therewithin the rectangular mounting platform 98.

In another embodiment of the disclosure, a CPAP compliance notification method 400 is described and disclosed, as shown in FIGS. 12A-12D, the CPAP compliance notification method 400 comprising one or more computer implemented programmable logic controller(s) 200, each programmable logic controller 200 having one or more microprocessors, the one or more microprocessors on which instructions are stored, the instructions when executed by one or more actions of the user causes the one or more processors together with the user to perform a CPAP compliance notification method 400, the CPAP compliance notification method 400 comprising, receiving instructions to provide a CPAP treatment to a patient P 120 identifying components, the components including: a CPAP compliance notification apparatus 50 for use with a CPAP device 10 having a flow generator 18, a CPAP hose 20, a CPAP mask 40; providing the CPAP device 10 having a flow generator 18, providing the CPAP hose 20; providing the CPAP mask 40; providing the CPAP compliance and notification apparatus 50, the CPAP compliance and notification apparatus 50, comprising: a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, a programmable logic controller 200 and together with a patient P 120, to control parameters of the CPAP compliance notification apparatus 50 in implementing a compliant CPAP treatment to the patient P 120, as shown in FIG. 5A-6B, for use with a CPAP device 10 having the flow generator 18, the CPAP hose 20, and the CPAP mask 40.

Wherein the CPAP compliance notification apparatus 50, comprises the patient occupancy mat 30 having a weight pressure sensor 32 including a weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

The air pressure sensor 84 is positioned remotely within the compliance notification controller unit 52, the air pressure sensor 84 having an air pressure sensor switch SW2 86 therein positioned remotely from an airway of the patient P 120 and remotely from a blower outlet $18^1$ of the flow generator 18 of the CPAP device 10, wherein the air pressure sensor 84 is operable to generate the air pressure sensor signal S2 triggered at the patient's P 120 lodgment of the CPAP mask 40 on the patient's P 120 face, wherein the air pressure sensor signal S2 is interrupted upon the patient's P 120 dislodgement of the CPAP mask 40 from the patient's P 120 face.

The air pressure tube 80 having an interior hollow channel limited by an open first end $80^1$ having the first opening 83 can be releasable connected to the CPAP hose 20 by means of the air pressure tube adapter 88 proximate to the flow generator 18 and a second end $80^2$ having the second opening 85 positioned releaseably connected to the air pressure sensor 84 housed within the compliance notification controller unit 52. The air pressure tube adapter 88 is the tube extender 88 having a first opening sized to be flush with the first end $80^1$ opening of the air pressure tube 80 and an opposing second opening sized to be flush with an inlet on the CPAP hose 20, the inlet on the CPAP hose 20 proximate to the flow generator 18. The second open end $80^2$ of the air pressure tube 80 communicates with an inlet port of the air pressure sensor 84.

In this exemplary embodiment, as shown in FIGS. 5A, 7 and 8, the solenoid 94 includes a plunger 92 coextensive with an anterior portion of the solenoid 94 and does not include the reset button 90.

The compliance notification controller unit 52, includes the housing 53 operable to maintain the compliance notification controller unit 52 components in one location proximate to each other. The compliance notification controller unit 52 components, including a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, a programmable logic controller 200 and together with a patient P 120, to control parameters of the CPAP compliance notification apparatus 50 in implementing a compliant CPAP treatment to the patient P 120.

The one or more ports 78, 68, and 66, an electrical supply socket 69 of the type suitable for receiving a universal power cord plug 63 operable for supplying electrical power supply to the compliance notification controller unit 52; one or more DC power sources 110 operable to direct electrical power; a rechargeable battery 202; a mobile communication device docking station with charger 204; a buzzer 61; the buzzer 61 including a timer-output 72 adapted and operable to direct an audible alarm to the patient P 120, the audible alarm having sufficient intensity to alert the patient P 120, whereby the buzzer 61 is adapted and operable to alert the patient P 120 during the patient's P 120 occupancy on the patient occupancy mat 30 of the interruption in air pressure at an interior channel of the air pressure tube 80 indicative that the patient P 120 has not lodged his/her CPAP mask 40 within one or more assigned time-delay off time(s) t. The buzzer 61 is, also, adapted and operable to alert the patient P 120 during the patient's vacating the patient occupancy mat 30 indicative that the P 120 has not returned to the patient occupancy mat 30 within one or more assigned time-delay off time(s) t.

The user interface 206 including a touch screen 208 includes one or more text displays 210. A first text display $210^1$ of the one or more text displays 210 includes an on/off text display $210^1$, wherein the on/off text display $210^1$ being adapted and operable when pressed to direct an "on-mode" and an "off-mode" of the CPAP device 10 via contact of the solenoid 94 plunger 92 against an on/off button of the CPAP device 10.

A second text display $210^2$ of the one or more text displays 210 includes a reset text display $210^2$, wherein the reset text display $210^2$ being adapted and operable when pressed to direct an audible alarm of the buzzer 61 to turn off and to restart one or more timers 60.

A third text display $210^3$ of the one or more text displays 210 includes a snooze text display $210^3$, wherein the snooze text display $210^3$ being adapted and operable when pressed to direct one or more timers 60 within the programmable logic controller 200 to delay the buzzer 61 from sounding an audible alarm.

The programmable logic controller 200 is configured and adapted to implement parameters to perform a methodology of a compliant continuous positive airway pressure treatment for the patient P 120, wherein the programmable logic controller 200, comprising one or more microprocessors is configured to receive instructions to implement a method of a CPAP treatment for the patient P 120, one or more timers 60, receive digital input data, receive analog input data; transmit digital output data; wherein digital input data includes identifying, parameters of the weight pressure sensor signal S1, the weight pressure sensor switch SW1 35, and parameters of the one or more timers 60, wherein analog input data includes identifying parameters of the air pressure sensor signal S2, the air pressure sensor switch SW2 86, and wherein the digital output includes identifying parameters of the buzzer 61, the solenoid 94, and the user interface 206.

Continued within the CPAP compliance notification method 400 is positioning the patient occupancy mat 30 having the weight pressure sensor 35 approximate to the supportive substrate 124, for example a bed, or any one of the supportive substrates 124 mentioned above; occupying the patient occupancy mat 30 by the patient P 120; lodging the patient CPAP mask 40 so that the CPAP mask 40 seals over the patient's P 120 nose and mouth.

The one or more processors of the programmable logic controller 200: receiving a first digital input data identifying a patient P 120 detected on a patient occupancy mat 30, the first digital input data including a weight pressure sensor signal S1 generated from the weight pressure sensor 35 integrally connected within the patient occupancy mat 30;

deriving the weight pressure sensor signal S1, wherein deriving the weight pressure sensor signal S1 includes causing a weight pressure sensor switch SW1 35 to close; deriving the weight pressure sensor signal S1, wherein deriving the weight pressure sensor signal S1 includes causing a timer-output 72 to close; deriving the timer-output 72 being closed, wherein deriving the timer-output 72 being closed includes causing the timer 60 to start counting down to the one or more assigned time-delay off time(s) t; deriving the weight pressure sensor signal S1, wherein deriving the weight pressure sensor signal S1 at zero includes causing the weight pressure sensor switch SW1 35 to open.

Further, the one or more microprocessors of the programmable logic controller 200 using the closure of the weight pressure sensor switch SW1 35 to cause a CPAP device 10 to power to the on-mode via the solenoid 94 whereby the plunger 92 of the solenoid 94 presses against the on/off button 12 of the CPAP device 10 causing the flow generator 18 to deliver continuous positive airway pressure channeled through the CPAP hose 20 to the patient's CPAP mask 40 and simultaneously cause a timer 60 of the one or more timers 60 to start counting down to the one or more assigned time-delay off time(s) t; receiving a second data, the second data identifying an air pressure within an air pressure tube 80 interconnected to the CPAP hose 20 proximate to a blower outlet of the CPAP flow generator 18 identifying a CPAP mask 40 detected lodged on the patient's P 120 face, the second data including an air pressure sensor signal S2 generated from an air pressure sensor 84 integrally positioned remotely into the compliance notification controller unit 52; deriving the air pressure sensor signal S2, wherein deriving the air pressure sensor signal S2 includes causing an air pressure sensor switch SW2 86 to close; receiving a third data identifying one or more assigned time-delay off time(s) t before the patient P 120 must comply and lodge his/her CPAP mask 40 sealing over his/her nose and mouth to prevent the buzzer 61 from sounding the audible alarm; receiving a fourth data identifying a time-delayed off time t of one or more assigned time-delay off time(s) t before the patient P 120 must comply and re-occupy the patient occupancy mat 30 after vacating the patient occupancy mat 30 to prevent the CPAP device 10 from powering to the off-mode; determining the closure of the weight pressure sensor switch SW1 35 on a comparison to the closure of the air pressure sensor switch SW2 86, wherein the determination of the closure of the weight pressure sensor switch SW1 35 and the closure of the air pressure sensor switch SW2 86 together causes a timer-output 72 to open; using the opening of the timer-output 72 so that the buzzer 61 does not sound the audible alarm.

Further, dislodging the patient's P 120 CPAP mask 40; deriving the air pressure sensor signal S2, wherein deriving the air pressure sensor signal S2 at zero includes causing the air pressure sensor switch SW2 86 to open; determining the closure of the weight pressure sensor switch SW1 35 on a comparison to an open air pressure sensor switch SW2 86, wherein the determination of the closure of the weight pressure sensor switch SW1 35 and the open air pressure sensor switch SW2 86 together causes a timer-output 72 to close; using the closed timer-output 72 so that the buzzer 61 sounds the audible alarm at an end of the one or more of the assigned time-delay off time(s) t to alert the patient P 120 to lodge his/her CPAP mask 40.

Identifying a reset feature $210^2$, the reset text display $210^2$, of the touch screen 208 of the user interface 206 of the compliance controller notification unit 52; receiving a fifth data identifying the reset feature $210^2$, the reset text display $210^2$, is triggered; using the triggered reset feature $210^2$, the reset text display $210^2$, so that the closed timer-output 72 is open; using the open timer-output 72 so that the audible alarm of the buzzer 61 is silenced; resuming the CPAP therapy for the patient P 120.

Receiving a sixth data, identifying the patient P 120 vacated the patient occupancy mat 30, the sixth data including a weight pressure sensor signal S1 at zero generated from the weight pressure sensor 32 integrally connected within the patient occupancy mat 30; deriving the weight pressure sensor signal S1, wherein deriving the weight pressure sensor signal S1 at zero when the patient P 120 vacates the patient occupancy mat 30 includes causing the weight pressure sensor switch SW1 35 to open; and deriving the weight pressure sensor signal S1, wherein deriving the weight pressure sensor signal S1 at zero includes causing the timer-output 72 to open; using the open weight pressure sensor switch SW1 35 in simultaneous communication use the closed air pressure sensor switch SW2 86 when the patient P 120 has successfully lodged his/her CPAP mask 40.

Determining the open weight pressure sensor switch SW1 35 on a comparison to a closed air pressure sensor switch SW2 86, wherein the determination of the open weight pressure sensor switch SW1 35 and the closed air pressure sensor switch SW2 86 together causes the timer-output 72 to close; using the closed timer-output 72 so that the buzzer 61 sounds the audible alarm at an end of the one or more of the assigned time-delay off time(s) to alert the patient P 120 to occupy the patient occupancy mat 30; identifying the reset feature, the reset text display $210^2$, of the touch screen 208 of the user interface 206 from the compliance notification controller unit 52; receiving a seventh data identifying the reset feature is triggered; using the triggered reset feature, the reset text display $210^2$, so that the closed timer-output 72 is open; using the open timer-output 72 so that the audible alarm of the buzzer 61 is silenced; resuming the CPAP treatment for the patient P 120.

Deriving the air pressure sensor signal S2 to be zero, wherein deriving the air pressure sensor signal at zero includes causing the air pressure sensor switch SW2 86 to open; using the open weight pressure sensor switch SW1 35 and in simultaneous communication using the open air pressure switch SW2 86 causing the CPAP device to power to the off-mode via the solenoid 94 whereby the plunger 92 of the solenoid 94 presses against the on/off button 12 of the CPAP device 12 causing cessation of the flow generator 18 to deliver continuous positive airway pressure channeled through the CPAP hose 20 to the patient's CPAP mask 40 to the patient P 120; using the open timer-output 72 to cause the timer 60 to cease counting down to the one or more assigned time-delay off time(s) t; and causing the CPAP treatment for the patient P 120 to end.

In another embodiment of the subject matter of the disclosure is a CPAP compliance notification method 500, as shown in FIGS. 13A-13D, with use with a CPAP device 10 having a CPAP hose 20 and a CPAP mask 40, the CPAP compliance notification method 500, comprising the steps of: providing instructions to a programmable logic controller 200 of a CPAP notification compliance apparatus 50 to provide a CPAP treatment to a patient P 120; providing a CPAP compliance notification apparatus 50 for use with a CPAP device 10 having a flow generator 18, a CPAP hose 20, a CPAP mask 40; providing the CPAP device 10 having the flow generator 18; providing the CPAP hose 20; providing the CPAP mask 40; providing the CPAP compliance notification apparatus 50, the CPAP compliance notification apparatus 50, comprises a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, and together with a patient P 120, to control parameters of the CPAP compliance notification apparatus 50 in implementing a compliant CPAP treatment to the patient P 120.

The patient occupancy mat 30 includes a weight pressure sensor 32 including a weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

The air pressure sensor 84 includes an air pressure sensor switch SW2 86 therein positioned within the compliance notification controller unit 52 remotely from an airway of the patient P 120 and remotely from a blower outlet $18^1$ of the flow generator 18 of the CPAP device 10, wherein the air pressure sensor 84 is operable to generate the air pressure sensor signal S2 triggered at the patient's P 120 lodgment of the CPAP mask 40 on the patient's P 120 face, wherein the air pressure sensor signal S2 is interrupted upon the patient's P 120 dislodgement of the CPAP mask 40 from the patient's P 120 face.

The air pressure tube 80 having an interior hollow channel limited by an open first end $80^1$ having the first opening 83 can be releasable connected to the CPAP hose 20 by means of the air pressure tube adapter 88 proximate to the flow generator 18 and a second end $80^2$ having the second opening 85 positioned releaseably connected to the air pressure sensor 84, the air pressure sensor 84 housed within the compliance notification controller unit 52. The air pressure tube adapter 88 is the tube extender 88 having a first opening sized to be flush with the first end $80^1$ opening of the air pressure tube 80 and an opposing second opening sized to be flush with an inlet on the CPAP hose 20, the inlet proximate to the flow generator 18. The second open end $80^2$ of the air pressure tube communicates with an inlet port of the air pressure sensor 84.

In this exemplary embodiment, as shown in FIGS. 5A, 7 and 8, the solenoid 94 includes a plunger 92 coextensive with an anterior portion of the solenoid 94 and does not include the reset button 90.

The compliance notification controller unit 52, includes the housing 53 operable to maintain the compliance notification controller unit 52 components in one location proximate to each other. The compliance notification controller unit 52 components, including a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, and together with a patient P 120, to control parameters of the CPAP compliance notification apparatus 50 in implementing a compliant CPAP treatment to the patient P 120.

The one or more ports 78, 68, and 66, an electrical supply socket 69 of the type suitable for receiving a universal power cord plug 63 operable for supplying electrical power supply to the compliance notification controller unit 52; one or more DC power sources 110 operable to direct electrical power; a rechargeable battery 202; a mobile communication device docking station with charger 204; a buzzer 61; the buzzer 61 including a timer-output 72 adapted and operable to direct an audible alarm to the patient P 120, the audible alarm having sufficient intensity to alert the patient P 120, whereby the buzzer 61 is adapted and operable to alert the patient P 120 during the patient's P 120 occupancy on the patient occupancy mat 30 of the interruption in air pressure at an interior channel of the air pressure tube 80 indicative that the patient P 120 has not lodged his/her CPAP mask 40 within one or more assigned time delay off-time(s) t.

The user interface 206 including a touch screen 208 includes one or more text displays 210. A first text display $210^1$ of the one or more text displays 210 includes an on/off text display $210^1$, wherein the on/off text display $210^1$ being adapted and operable when pressed to direct an "on-mode" and an "off-mode" of the CPAP device 10 via contact of the solenoid 94 plunger 92 against an on/off button of the CPAP device 10.

A second text display $210^2$ of the one or more text displays 210 includes a reset text display $210^2$, wherein the reset text display $210^2$ being adapted and operable when pressed to direct an audible alarm of the buzzer 61 to turn off and to restart a timer 60 of the one or more timers 60.

A third text display $210^3$ of the one or more text displays 210 includes a snooze text display $210^3$, wherein the snooze text display $210^3$ being adapted and operable when pressed to direct one or more timers 60 within the programmable logic controller 200 to delay the buzzer 61 from sounding the audible alarm.

The programmable logic controller 200 is configured and adapted to implement parameters to perform a methodology of a compliant continuous positive airway pressure treatment for the patient P 120, wherein the programmable logic controller 200, comprising one or more microprocessors is configured to receive instructions to implement a method of a CPAP treatment for the patient P 120, one or more timers 60, receive digital input data, receive analog input data; transmit digital output data; wherein digital input data includes identifying, parameters of the weight pressure sensor signal S1, the weight pressure sensor switch SW1 35, and parameters of the one or more timers 60, wherein analog input data includes identifying parameters of the air pressure sensor signal S2, the air pressure sensor switch SW2 86, and wherein the digital output includes identifying parameters of the buzzer 61, the solenoid 94, and the user interface 206.

Now continuing with the exemplary CPAP compliance notification method 500, includes the patient P 120 positioning the patient occupancy mat 30 having the weight pressure sensor 32 approximate to the supportive substrate 124; programming a time-delay off time t of one or more time-delay off times; the patient P 120 occupying the patient occupancy mat 30 causing the weight pressure sensor 32 to generate a weight pressure sensor signal S1; causing the weight pressure sensor switch SW1 35 to close; causing the timer-output 72 to close; causing the CPAP device 10 to power to on-mode and in simultaneous communication causing the timer 60 of the one or more timers 60 automatically to start and countdown to one or more time-delay off time(s) t; lodging the CPAP mask 40 onto the patient's P 120 face so that the CPAP mask 40 seals over his/her nose and mouth within an end limit of an assigned time-delay off time t of the one or more time-delay off time(s) t; causing the air pressure sensor 84 to generate an air pressure sensor signal S2; causing the air pressure sensor switch SW2 86 to close and in simultaneous communication causing the timer-output 72 to open so that the buzzer 61 does not sound the audible alarm in the event the patient P 120 manages to maintain his/her CPAP mask 40 sealed during the subsequent sleep cycle; the patient P 120 resting through the sleep cycle duration wherein the patient P 120 receives a prescribed continuous air pressure treatment for a sleep apnea; the patient P 120 waking and removing his/her CPAP mask 40 and accordingly causing an interruption in the air pressure sensor signal S2; causing the air pressure sensor switch SW2 86 to open; the patient P 120 vacating the patient occupancy mat 30; causing an interruption in the weight pressure sensor signal S1; causing the weight pressure sensor SW1 35 to open; using the open weight pressure sensor switch SW1 35 in simultaneous communication using the open air pressure sensor switch SW2 86; determining the open weight pressure sensor switch SW1 35 on a comparison to the open air pressure sensor switch SW2 86, wherein the determination of the open weight pressure sensor switch SW1 35 and the open air pressure sensor switch SW2 86 together causes the timer-output 72 to close; using the closed timer-output 72 so that the buzzer 61 sounds the audible alarm at the end of the assigned time-delay off time(s) t to alert the patient P 120 to re-occupy the patient occupancy mat 30 and to re-lodge his/her CPAP mask 40; identifying the reset feature, the reset text display 210² of the touchscreen 208 of the compliance controller unit 52; receiving data identifying the reset feature, reset text display 210², is triggered; using the triggered reset feature, reset text display 210², so that the closed timer-output 72 is open; using the open timer-output 72 so that the audible alarm of the buzzer 61 is silenced; resuming the CPAP treatment for the patient P 120; the patient P 120 vacating the patient occupancy mat 30 causing the weight pressure sensor switch SW1 35 to open; the patient P 120 dislodging his/her CPAP mask 40 causing the air pressure sensor switch SW1 86 to open; using the determination of the open weight pressure sensor switch SW1 35 and the determination of the open air pressure sensor switch SW2 86 in simultaneous communication; causing the CPAP device 10 to power to the off-mode; causing the timer 60 to stop counting down to the assigned time-delay off time t; and causing the CPAP treatment to end.

The CPAP compliance notification method 500, further comprising the steps of the patient P 120 positioning the patient occupancy mat 30 having a weight pressure sensor 32 approximate to the supportive substrate 124; programming the time delay off-time t; the patient P 120 occupying the patient occupancy mat 30; causing the weight pressure sensor 32 to generate the weight pressure sensor signal S1; causing weight pressure sensor switch SW1 35 to close; causing the CPAP device 10 to power to on-mode; causing the timer-output 72 to close; causing the timer 60 automatically to start and count down to the programmed time delay off-time t; failing to lodge the CPAP mask 40 onto the patient's face so that the CPAP mask 40 does not seal over his/her nose and mouth within an end limit of the programmed time delay off-time; causing the air pressure sensor switch SW2 86 to open; causing the buzzer 86 to sound the audible alarm to alert the patient P 120 to lodge his/her CPAP mask 40; pressing the reset text display 210³; and causing the timer-output 72 to open; causing the buzzer 61 to silence the audible alarm, and in simultaneous communication causing the timer 60 to restart; and resuming the CPAP treatment for the patient P 120.

The CPAP compliance notification method 500, further comprising the steps: the patient P 120 occupying the patient occupancy mat 30 including the weight pressure sensor 32 and shortly thereafter vacates the patient occupancy mat 30 for a period of time, and subsequently returns to the patient occupancy mat 30. In one scenario, the patient P 120 may fall out of bed 122. Therefore, the CPAP compliance notification apparatus 50 is configured to maintain the CPAP device 10 in the on-mode so that the continuous positive air pressure continues to be delivered through the CPAP hose 20 and to the CPAP mask 40 of the patient P 120.

In this scenario, the patient P 120 waking and maintaining his/her CPAP mask 40 over his/her mouth and nose and accordingly maintaining the air pressure sensor signal S2; causing the air pressure sensor switch SW2 86 to remain closed; the patient P 120 vacating the patient occupancy mat 30 because he/she has fallen out of bed 122 causing an interruption in the weight pressure sensor signal S1 causing the weight pressure sensor switch SW1 32 to open; using the open weight pressure sensor switch SW1 35 in simultaneous communication with the closed air pressure sensor switch SW2 86; determining the open weight pressure sensor switch SW1 35 on a comparison to the closed air pressure sensor switch SW2 86, wherein the determination of the open weight pressure sensor switch SW1 35 and the closed air pressure sensor switch SW2 86 together causes the timer-output 72 to close; using the closed timer-output 72 so that the buzzer 61 sounds an alarm at an end of the one or more of the assigned programmed time-delay off time t to alert the patient P 120 to re-occupy the patient occupancy mat 30; identifying the reset feature, reset text display 210², from the touchscreen 208 of the compliance controller unit 52; receiving data identifying the reset feature 210², reset text display 210², is triggered; using the triggered reset feature 210², reset text display 210², so that the closed timer-output 72 is open; using the open timer-output 72 so that the audible alarm of the buzzer 61 is silenced; and resuming the CPAP treatment for the patient P 120.

Figure 14:
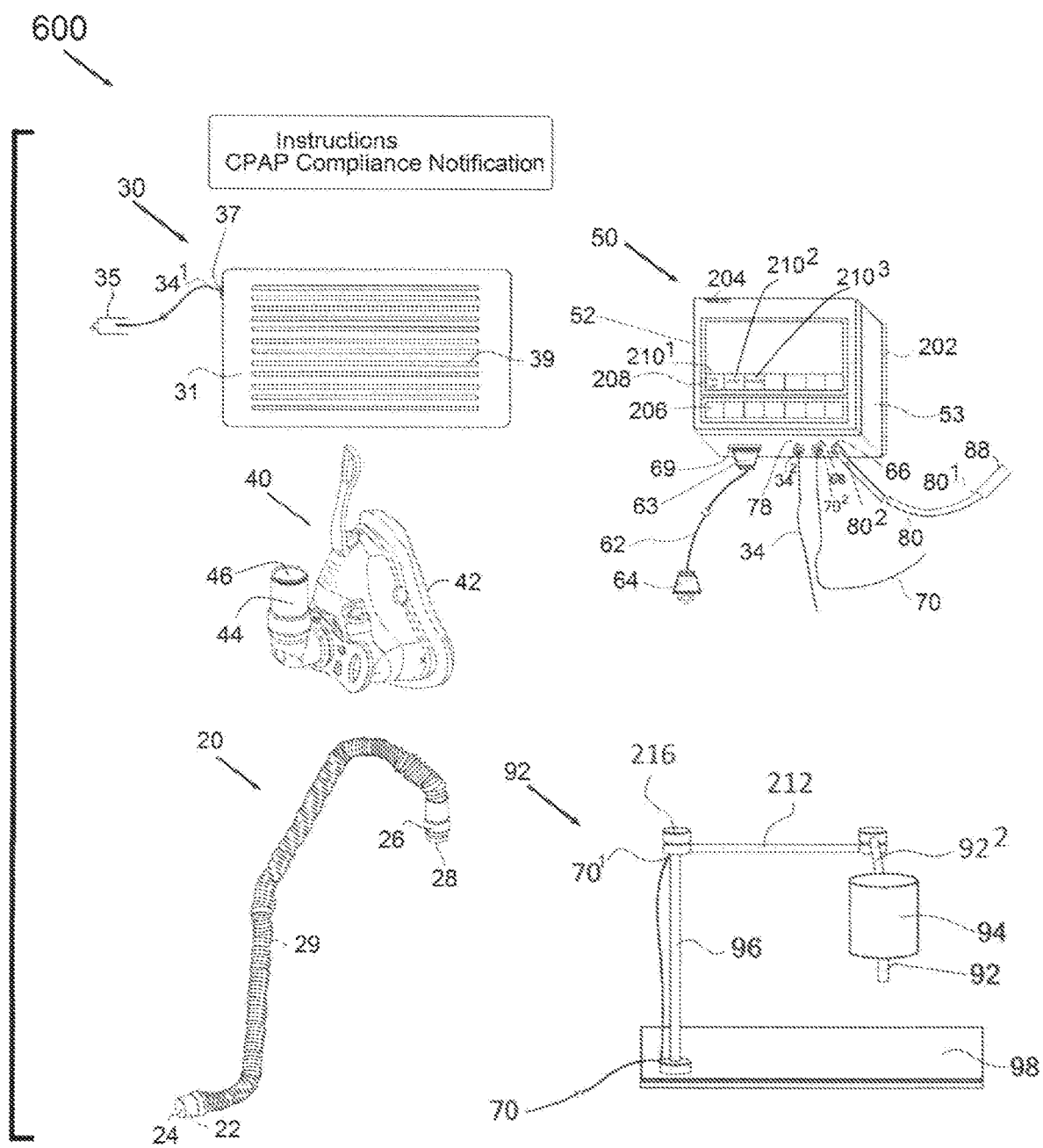
FIG. 14 shows a CPAP compliance notification system kit.

In another embodiment of the subject matter of the disclosure is a CPAP compliance notification kit 600, as shown in FIG. 14, for use with a CPAP device 10 having a flow generator 18, a CPAP hose 20, and a CPAP mask 40, the CPAP compliance notification kit 600 comprising instructions of use of a CPAP compliance notification apparatus 50; the compliance notification apparatus 50 comprising the programmable logic controller 200, as shown in FIG. 5A-6B for use with a CPAP device 10 having the flow generator 18, the CPAP hose 20, and the CPAP mask 40. The CPAP compliance notification apparatus 50, comprises, a patient occupancy mat 30, an air pressure sensor 84, an air pressure tube 80, a solenoid 94, a compliance notification controller unit 52, the compliance notification controller unit 52 including, a housing operable to maintain compliance notification controller components comprising, one or more ports 66, 68, 78, a programmable logic controller 200, an electrical supply socket 69, one or more DC power sources 110, a rechargeable battery 202, a mobile communication device docking station 204, the air pressure sensor 84, a buzzer 61, a user interface 206, and together with a patient P 120, to control parameters of the CPAP compliance notification apparatus 50 in implementing a compliant CPAP treatment to the patient P 120.

The patient occupancy mat 30 includes a weight pressure sensor 32 including a weight pressure sensor switch SW1 35 therein for detecting the patient P 120 upon the patient occupancy mat 30, the weight pressure sensor 32 operable to generate a weight pressure sensor signal S1 triggered at the patient's P 120 occupancy of the patient occupancy mat 30, wherein the weight pressure sensor signal S1 is interrupted upon the patient P 120 vacating the patient occupancy mat 30.

The air pressure sensor 84 positioned within the compliance notification controller unit 52, the air pressure sensor 84 having an air pressure sensor switch SW2 86 therein, the air pressure sensor 84 positioned remotely from an airway of the patient P 120 and remotely from a blower outlet 18$^1$ of the flow generator 18 of the CPAP device 10, wherein the air pressure sensor 84 is operable to generate the air pressure sensor signal S2 triggered at the patient's P 120 lodgment of the CPAP mask 40 on the patient's P 120 face, wherein the air pressure sensor signal S2 is interrupted upon the patient's P 120 dislodgement of the CPAP mask 40 from the patient's P 120 face.

The air pressure tube 80 having an interior hollow channel limited by an open first end 80$^1$ having the first opening 83 which can be releasable connected to the CPAP hose 20 by means of the air pressure tube adapter 88 proximate to the flow generator 18 and a second end 80$^2$ having the second opening 85 positioned releaseably connected to the air pressure sensor 84 housed within the compliance notification controller unit 52. The air pressure tube adapter 88 is the tube extender 88 having a first opening sized to be flush with the first end 80$^1$ opening of the air pressure tube 80 and an opposing second opening sized to be flush with an inlet on the CPAP hose 20, the inlet proximate to the flow generator 18. The second open end 80$^2$ of the air pressure tube communicates with an inlet port of the air pressure sensor 84.

In this exemplary embodiment, the solenoid 94 includes a plunger 92 coextensive with an anterior portion of the solenoid 94 and does not include the reset button 90.

The compliance notification controller unit 52, includes the housing 53 operable to maintain the compliance notification controller unit 52 components in one location proximate to each other. The compliance notification controller unit 52 components, including the one or more ports 78, 68, and 66, the electrical supply socket 69 of the type suitable for receiving a universal power cord plug 63 operable for supplying electrical power supply to the compliance notification controller unit 52; one or more DC power sources 110 operable to direct electrical power; the rechargeable battery 202; the mobile communication device docking station with charger 204; the buzzer 61; the buzzer 61 including a timer-output 72 adapted and operable to direct an audible alarm to the patient P 120, the audible alarm having sufficient intensity to alert the patient P 120, whereby the buzzer 61 is adapted and operable to alert the patient P 120 during the patient's P 120 occupancy on the patient occupancy mat 30 of the interruption in air pressure at an interior channel of the air pressure tube 80 indicative that the patient P 120 has not lodged his/her CPAP mask 40 within one or more assigned time delay off-time(s) t.

The user interface 206 including a touch screen 208 includes one or more text displays 210. A first text display 210$^1$ of the one or more text displays 210 includes an on/off text display 210$^1$, wherein the on/off text display 210$^1$ being adapted and operable when pressed to direct an "on-mode" and an "off-mode" of the CPAP device 10 via contact of the solenoid 94 plunger 92 against an on/off button of the CPAP device 10.

A second text display 210$^2$ of the one or more text displays 210 includes a reset text display 210$^2$, wherein the reset text display 210$^2$ being adapted and operable when pressed to direct an audible alarm of the buzzer 61 to turn off and reset a timer 60 of one or more timers 60.

A third text display 210$^3$ of the one or more text displays 210 includes a snooze text display 210$^3$, wherein the snooze text display 210$^3$ being adapted and operable when pressed to direct one or more timers 60 within the programmable logic controller 200 to delay the buzzer 61 sounding the audible alarm.

The programmable logic controller 200 is configured and adapted to implement parameters to perform a methodology of a compliant continuous positive airway pressure treatment for the patient P 120, wherein the programmable logic controller 200, comprising one or more microprocessors is configured to receive instructions to implement a method of a CPAP treatment for the patient P 120, one or more timers 60, receive digital input data, receive analog input data; transmit digital output data; wherein digital input data includes identifying, parameters of the weight pressure sensor signal S1, the weight pressure sensor switch SW1 35, and parameters of the one or more timers 60, wherein analog input data includes identifying parameters of the air pressure sensor signal S2, the air pressure sensor switch SW2 86, and wherein the digital output includes identifying parameters of the buzzer 61, the solenoid 94, and the user interface 206.

Naturally, a person skilled in the art may apply to the solution described above many logical and/or physical modifications and alterations. More specifically, although the disclosure describes with a certain degree of particularity some embodiments, it should be understood that various omissions, substitutions and changes in the form and details as well as other embodiments are possible. Particularly, the proposed solution may even be practiced without the specific details (such as the specific voltages) set forth in the preceding description to provide a more thorough understanding thereof; conversely, well-known features may have been omitted or simplified in order not to obscure the description with unnecessary particulars. Moreover, it is expressly intended that specific element and/or method steps described in connection with any disclosed embodiment may be incorporated in any other embodiment as a matter of general design choice.

From the foregoing it will be appreciated that, although, specific embodiments of the invention have been described herein for purposes of illustration, various modifications may be made without deviating from the spirit and scope of the invention. Accordingly, the invention is not limited except as by the appended claims.

What is claimed is:

1. A CPAP compliance notification apparatus for use with a CPAP device having a flow generator, a CPAP hose, and a CPAP mask, the CPAP compliance notification apparatus, comprising:

a patient occupancy mat having a weight pressure sensor including a weight pressure sensor switch (SW1) therein for detecting a patient upon the patient occupancy mat, the weight pressure sensor operable to generate a weight pressure sensor signal (S1) triggered at the patient's occupancy of the patient occupancy mat, wherein the weight pressure sensor signal (S1) is interrupted upon the patient vacating the patient occupancy mat;

a compliance notification controller unit including components;

the compliance notification controller unit components, comprising:
      an air pressure sensor;
      one or more ports;

an electrical supply socket of a type suitable for receiving a universal power cord plug operable for supplying electrical power supply to the compliance notification controller unit;
one or more DC power sources operable to direct electrical power;
a rechargeable battery;
a mobile communication device docking station with charger;
a buzzer;
an air pressure sensor having an air pressure sensor switch (SW2) therein, the air pressure sensor positioned within the compliance notification controller unit remotely from an airway of the patient and remotely from a blower outlet of the flow generator, the air pressure sensor operable to generate an air pressure sensor signal (S2) triggered at the patient's lodgment of the CPAP mask on the patient's face, wherein the air pressure sensor signal (S2) is interrupted upon the patient's dislodgement of the CPAP mask from the patient's face;
an air pressure tube having an interior hollow channel limited by an open first end and an opposing open second end, the first open end communicating with the CPAP hose via a tube extender at a position proximate to the flow generator, the second open end communicating with an inlet port of the air pressure sensor;
a solenoid including a plunger coextensive with an anterior portion of the solenoid;
a housing operable to maintain the compliance notification controller unit components in one location proximate to each other;
the buzzer including a timer-output adapted and operable to direct an audible alarm to alert the patient during the patient's occupancy on the patient occupancy mat of interruption in air pressure at the interior hollow channel of the air pressure tube indicative that the patient has not lodged his/her CPAP mask within an assigned time delay off-time of one or more assigned time delay off-time(s);
a user interface including a touch screen including one or more text displays;
a first text display of the one or more text displays includes an on/off text display, wherein the on/off text display being adapted and operable when pressed to direct an "on-mode" and an "off-mode" of the CPAP device via contact of the plunger against an on/off button of the CPAP device;
a second text display of the one or more text displays includes a reset text display, wherein the reset text display being adapted and operable when pressed to direct the audible alarm of the buzzer to turn off;
a third text display of the one or more text displays includes a snooze text display, wherein the snooze text display being adapted and operable when pressed to delay the buzzer;
a programmable logic controller configured and adapted to implement parameters to perform a methodology of a compliant continuous positive airway pressure treatment for the patient;
the programmable logic controller, comprising:
one or more microprocessors configured to:
receive instructions to implement the methodology of the compliant continuous positive airway pressure treatment for the patient;
receive instructions to implement one or more timers assigned to any one of the one or more assigned time delay off-times;
receive input data;
transmit output data;
receive digital input data;
receive analog input data;
transmit digital output data;
wherein digital input data includes identifying parameters of the weight pressure sensor signal (S1), the weight pressure sensor switch (SW1), and parameters of any one of the one or more timers;
wherein analog input data includes identifying parameters of the air pressure sensor signal (S2), the air pressure sensor switch (SW2); and
wherein digital output data includes identifying parameters of the buzzer, the solenoid, and the user interface.

2. The CPAP compliance notification apparatus, according to claim 1, wherein the patient occupancy mat is positioned proximate to a supportive substrate.

3. The CPAP compliance notification apparatus, according to claim 2, wherein the supportive substrate comprises any one of the group comprising, bed mattress, wheelchair, recliner chair, air mattress, a sleep medium, a sitting medium.

4. The CPAP compliance notification apparatus, according to claim 1, wherein the weight pressure sensor switch (SW1) of the weight pressure sensor is adapted and operative to power to its closed position via the programmable logic controller's derivation of the weight pressure sensor signal (S1) generated at the patient occupying the patient occupancy mat, whereby the weight pressure sensor switch (SW1) in its closed position operably causes the CPAP device to power to the on-mode so that the flow generator delivers continuous positive airway pressure channeled through the CPAP hose to the CPAP mask to the patient, and in simultaneous communication operably causes the timer of any one of the one or more timers to begin counting down to the assigned time delay off-time of any one of the one or more assigned time delay off-time(s).

5. The CPAP compliance notification apparatus, according to claim 1, wherein the weight pressure sensor switch (SW1) of the weight pressure sensor is adapted and operative to power to its open position via the programmable logic controller's derivation of the weight pressure sensor signal (S1) being zero generated at the patient vacating the patient occupancy mat, and in simultaneous communication the air pressure sensor switch (SW2) of the air pressure sensor is adapted and operative to power to its open position via the programmable logic controller's derivation of the air pressure sensor signal (S2) being interrupted indicative of failure to lodge the patient's CPAP mask onto the patient's face, or the dislodgement of the patient's CPAP mask, whereby the weight pressure sensor switch (SW1) in its open position and in simultaneous communication the air pressure sensor switch (SW2) in its open position operably causes the CPAP device to power to the off-mode via the solenoid so that the flow generator ceases to deliver continuous positive airway pressure channeled through the CPAP hose to the CPAP mask to the patient, and in simultaneous communication operably causes the timer of any one of the one or more timers to stop counting down to the assigned time delay off-time of any one of the one or more assigned time delay off-time(s).

6. The CPAP compliance notification apparatus according to claim 1, wherein the weight pressure sensor switch (SW1) of the weight pressure sensor is adapted and operative to power to its closed position via the programmable logic controller's derivation of the weight pressure sensor signal (S1) being generated at the patient occupying the patient occupancy mat, and in simultaneous communication the air pressure sensor switch (SW2) of the air pressure sensor is adapted and operative to power to its closed position via the programmable logic controller's derivation of the air pressure sensor signal (S2) being generated indicative of the lodgment of the CPAP mask upon the patient's face, whereby the weight pressure sensor switch (SW1) in its closed position and in simultaneous communication the air pressure sensor switch (SW2) in its closed position operably causes the CPAP device to be maintained in the on-mode and in simultaneous consideration operably causes the timer of any one of the one or more timers to stop counting down toward the assigned time delay off-time of any one of the one or more assigned time delay off-time(s) and in simultaneous communication operably causes the timer-output to open causing the buzzer to be inoperable and the audible alarm not to sound.

7. The CPAP compliance notification apparatus according to claim 1, wherein the weight pressure sensor switch (SW1) of the weight pressure sensor is adapted and operative to power to its closed position via the programmable logic controller's derivation of the weight pressure sensor signal (S1) being generated at the patient occupying the patient occupancy mat, and in simultaneous communication with the programmable logic controller's derivation of the air pressure sensor switch (SW2) of the air pressure sensor is adapted and operative to power to its open position based on the air pressure sensor signal (S2) being interrupted indicative of the patient failing to lodge the CPAP mask, or dislodgement of his/her CPAP mask, or a leak in the CPAP mask, which operably causes the timer of any one of the one or more timers to start counting down toward the assigned time delay off-time of any of the one or more assigned time delay off-time(s) and in simultaneous communication with the timer-output operably causes the timer-output to close causing the buzzer to be operable and sound the audible alarm to alert the patient in the event the patient does not lodge the CPAP mask before the assigned time delay off-time of any one of the one or more assigned time delay off-time(s).

8. The CPAP compliance notification apparatus according to claim 1, wherein the air pressure sensor switch (SW2) of the air pressure sensor is adapted and operative to power to its closed position via the programmable logic controller's derivation of the air pressure sensor signal (S2) being generated indicative of the lodgment of the CPAP mask on the patient's face, and in simultaneous communication the weight pressure sensor switch (SW1) of the weight pressure sensor is adapted and operative to power to its open position via the programmable logic controller's derivation of the weight pressure sensor signal (S1) being zero generated at the patient vacating the patient occupancy mat, which operably causes the timer of any one of the one or more timers to start counting down toward the assigned time delay off-time of the one or more assigned time delay off-time(s) and in simultaneous communication operably causes the timer-output to close causing the buzzer to be operable and sound the audible alarm to alert the patient in the event the patient does not occupy the patient occupancy mat before the assigned time delay off-time of the one or more assigned time delay off-time(s), and in simultaneous communication the CPAP device is maintained in the on-mode so that the flow generator continues to deliver continuous positive airway pressure channeled through the CPAP hose to the CPAP mask to the patient.

9. The CPAP compliance notification apparatus according to claim 1, wherein the solenoid is aligned vertically superior to the CPAP device on/off button, the solenoid configured to have the plunger coextensive from the anterior portion of the solenoid and operable so that when the on/off text display of the user interface is pressed, the plunger is depressed against the CPAP device on-off button causing the CPAP device in the off-mode to power to the on-mode.

10. The CPAP compliance notification apparatus according to claim 1, wherein the solenoid is aligned vertically superior to the CPAP device on/off button, the solenoid configured to have the plunger coextensive from the anterior portion of the solenoid and operable when the on/off text display is pressed the plunger is depressed against the CPAP device on/off button causing the CPAP device in the on-mode to power to the off-mode.

11. The CPAP compliance notification apparatus, according to claim 1, wherein when the patient is occupied on the patient occupancy mat and the CPAP mask is not lodged upon the patient's face within an assigned time delay off-time of the one or more assigned time delay off-time(s) in combination causes the weight pressure sensor switch (SW1) to close and the air pressure sensor switch (SW2) to open, respectively, and in simultaneous communication with the programmable logic controller causes the timer-output to close so that the buzzer sounds the audible alarm to alert the patient to lodge the CPAP mask.

12. The CPAP compliance notification apparatus, according to claim 1, wherein when the buzzer sounds the audible alarm, the patient can press the reset text display of the user interface causing the buzzer sounding the audible alarm to be silenced and causing the timer of any one of the one or more timers to restart while the CPAP device is maintained in the on-mode so that the flow generator continues to deliver continuous positive airway pressure channeled through the CPAP hose to the CPAP mask to the patient.

13. The CPAP compliance notification apparatus, according to claim 1, wherein the buzzer sounds the audible alarm when the patient vacates the patient occupancy mat and does not reoccupy the patient occupancy mat before the assigned time delay off-time of the one or more time delay off-times whereby the patient can press the reset text display of the user interface causing the buzzer sounding the audible alarm to be silenced while the CPAP device is maintained in the on-mode so that the flow generator continues to deliver continuous positive airway pressure channeled through the CPAP hose to the patient.

14. The CPAP compliance notification apparatus, according to claim 1, wherein when the patient is occupied on the patient occupancy mat and the CPAP mask is lodged upon the patient's face within the assigned time delay off-time of the one or more assigned time delay off-time(s) in combination causes the weight pressure sensor switch (SW1) to close and the air pressure sensor switch (SW2) to close, respectively, and in simultaneous communication with the programmable logic controller causes the timer-output to open so that the buzzer does not sound the audible alarm.

15. The CPAP compliance notification apparatus according to claim 1, wherein the solenoid is supported by a stand having a rigid vertical arm, a first horizontal arm and a second horizontal arm, wherein the first horizontal arm and the second horizontal arm is maneuverable via a thumb nut.

16. The CPAP compliance notification apparatus according to claim 1, further comprising a humidifier.

17. A CPAP compliance notification system, comprising:
one or more computer implemented programmable logic controller(s);
   wherein each of the one or more computer implemented programmable logic controllers of the one or more computer implemented programmable logic controllers includes one or more microprocessors;
a CPAP compliance notification apparatus having components;
wherein any one of the one or more microprocessors is configured to receive instructions from the components of the CPAP compliance notification apparatus to implement a CPAP treatment to a patient;
the CPAP compliance notification apparatus components comprising:
   a CPAP device having a flow generator, a CPAP hose, a CPAP mask;
   a patient occupancy mat having a weight pressure sensor including a weight pressure sensor switch (SW1) therein for detecting the patient upon the patient occupancy mat, the weight pressure sensor operable to generate a weight pressure sensor signal (S1) triggered at the patient's occupancy of the patient occupancy mat, wherein the weight pressure sensor signal (S1) is interrupted upon the patient vacating the patient occupancy mat;
   a compliance notification controller unit including components;
   the compliance notification controller unit components comprising:
      a housing operable to maintain the compliance notification controller unit components in one location proximate to each other;
      an air pressure sensor;
      one or more ports;
      an electrical supply socket of a type suitable for receiving a universal power cord plug operable for supplying electrical power supply to the compliance notification controller unit;
      one or more DC power sources operable to direct electrical power;
      a rechargeable battery;
      a mobile communication device docking station with charger;
      a buzzer;
      an air pressure tube having an interior hollow channel limited by an open first end and an opposing open second end, the first open end communicating with the CPAP hose via a tube extender at a position proximate to the flow generator, the second open end communicating with an inlet port of the air pressure sensor;
      a solenoid including a plunger coextensive with an anterior portion of the solenoid;
      the air pressure sensor having an air pressure sensor switch (SW2) therein, the air pressure sensor positioned within the compliance notification controller unit remotely from an airway of the patient and remotely from a blower outlet of the flow generator, the air pressure sensor operable to generate an air pressure sensor signal (S2) triggered at the patient's lodgment of the CPAP mask on the patient's face, wherein the air pressure sensor signal (S2) is interrupted upon the patient's dislodgement of the CPAP mask from the patient's face;
      the buzzer including a timer-output adapted and operable to direct an audible alarm to alert the patient;
      a user interface including a touch screen including one or more text displays;
      a first text display of the one or more text displays includes an on/off text display, wherein the on/off text display being adapted and operable when pressed to direct an "on-mode" and an "off-mode" of the CPAP device via contact of the plunger against an on/off button of the CPAP device;
      a second text display of the one or more text displays includes a reset text display, wherein the reset text display being adapted and operable when pressed to direct the audible alarm of the buzzer to turn off;
      a third text display of the one or more text displays includes a snooze text display, wherein the snooze text display being adapted and operable when pressed to delay the buzzer;
the microprocessor of the one or more microprocessors configured to:
   receive instructions to implement the methodology of a CPAP treatment for the patient;
   receive instructions to implement a timer of one or more timers assigned to a time delayed off-time of one or more assigned time delayed off-time(s);
   receive input data;
   transmit output data;
   receive digital input data;
   receive analog input data;
   transmit digital output data;
wherein digital input data includes identifying parameters of the weight pressure sensor signal (S1), the weight pressure sensor switch (SW1), and parameters of the timer of any one of the one or more timers;
wherein analog input data includes identifying parameters of the air pressure sensor signal (S2), the air pressure sensor switch (SW2);
wherein digital output data includes identifying parameters of the buzzer, the solenoid, and the user interface;
receive a first digital input data identifying the patient detected on the patient occupancy mat, the first digital input data input including the weight pressure sensor signal (S1) generated from the weight pressure sensor integrally connected within the patient occupancy mat;
derive the weight pressure sensor signal (S1), wherein deriving the weight pressure sensor signal (S1) includes causing the weight pressure sensor switch (SW1) to close;
receive a second digital input data identifying the patient vacating the patient occupancy mat, wherein the second digital input data including a weight pressure sensor signal (S1) at zero generated from the weight pressure sensor integrally connected within the patient occupancy mat;
derive the weight pressure sensor signal (S1), wherein deriving the weight pressure sensor signal (S1) at zero includes causing the weight pressure sensor switch (SW1) to open;
derive the closure of the weight pressure sensor switch (SW1);
transmit a first digital output data to the solenoid including the closure of the weight pressure sensor switch (SW1) to cause the CPAP device to power to the on-mode via the solenoid causing the flow generator to deliver continuous positive airway pressure channeled through the CPAP hose to the CPAP mask to the patient;

receive a third digital input data to cause the timer of any one of the one or more timers to start counting down to the assigned time delay off-time of the one or more assigned time delay off-time(s);

receive a fourth digital input data to cause the timer of any one of the one or more timers to stop counting down to the assigned time delay off-time of the one or more assigned time-delay off time(s);

receive a first analog input data, the first analog input data identifying an air pressure within the air pressure tube releasably attached to the air pressure sensor and interconnected to the CPAP hose proximate to a blower outlet of the flow generator identifying a CPAP mask detected lodged on the patient's face, the first analog input data including an air pressure sensor signal (S2) generated from the air pressure sensor disposed within the compliance notification controller unit;

derive the air pressure sensor signal (S2), wherein deriving the air pressure sensor signal (S2) includes causing the air pressure sensor switch (SW2) to close;

receive a second analog input data, the second analog input data identifying an air pressure within the air pressure tube releasably attached to the air pressure sensor and interconnected to the CPAP hose proximate to the blower outlet of the flow generator identifying the CPAP mask detected dislodged from the patient's face, the second analog input data including the air pressure sensor signal (S2) generated from the air pressure sensor disposed within the compliance notification controller unit is interrupted;

derive the air pressure sensor signal (S2), wherein deriving the air pressure sensor signal (S2) interrupted includes causing the air pressure sensor switch (SW2) to open;

derive the air pressure sensor signal (S2), wherein deriving the air pressure sensor signal (S2) at zero includes causing the air pressure sensor switch (SW2) to open;

receive a fifth digital input data identifying one or more assigned time delay off-time(s) before the patient must comply and lodge the CPAP mask sealing over the nose and mouth to prevent the buzzer from sounding the audible alarm;

receive a sixth digital input data identifying an assigned time delay off-time of the one or more time delay off-time(s) before the patient must comply and re-occupy the patient occupancy mat after vacating the patient occupancy mat to prevent the CPAP device from powering to the off-mode;

determine the closure of the weight pressure sensor switch (SW1) on a comparison to the closure of the air pressure sensor switch (SW2), wherein the determination of the closure of the weight pressure sensor switch (SW1) and the closure of the air pressure sensor switch (SW2) together causes a timer-output to open;

determine the open timer-output;

transmit a second digital output data to the solenoid of the open timer-output to cause the buzzer not to sound the audible alarm;

receive the second analog input data, the second analog input data identifying an air pressure within the air pressure tube, identifying the CPAP mask detected dislodged from the patient's face, the second analog input data including the air pressure sensor signal (S2) generated from the air pressure sensor disposed within the compliance notification controller unit is interrupted;

determine the closure of the weight pressure sensor switch (SW1) on a comparison to the open air pressure sensor switch (SW2), wherein the determination of the closure of the weight pressure sensor switch (SW1) and the opening of the air pressure sensor switch (SW2) together causes the timer-output to close;

derive the closed timer-output;

derive the closed timer-output to continue the one or more timers to counting down to the one or more assigned time delay off-times;

transmit a third digital output data to the solenoid of the closed timer-output to cause the buzzer to sound the audible alarm at an end of the one or more assigned time delay off-time(s) to alert the patient to lodge the CPAP mask;

derive the fourth digital input data to cause the timer of any one of the timers of the one or more timers to stop counting down to the one or more assigned time delay off-time(s);

identify a reset feature from the compliance notification controller unit;

trigger the reset feature;

transmit a fourth digital output data to the solenoid identifying the reset feature is triggered;

derive the triggered reset feature so that the closed timer-output is open;

derive the open timer-output;

transmit the second digital output data to the solenoid of the open timer-output to cause the buzzer not to sound the audible alarm so that the buzzer is silenced;

derive the third digital input data to cause the timer of any one of the timers of the one or more timers to start counting down to the one or more assigned time-delay off time(s);

resume the CPAP treatment for the patient;

receive the second digital input data, identifying a patient vacating the patient occupancy mat;

the second digital input data including the weight pressure sensor signal (S1) at zero generated from the weight pressure sensor integrally connected within the patient occupancy mat;

derive the weight pressure sensor signal (S1), wherein deriving the weight pressure sensor signal (S1) at zero includes causing the weight pressure sensor switch (SW1) to open in simultaneous communication derive the air pressure sensor signal (S2), wherein deriving the air pressure sensor signal (S2) includes causing the air pressure sensor switch (SW2) to remain closed and in simultaneous communication the CPAP device to be maintained in the on-mode so that the flow generator continues to deliver continuous positive airway pressure channeled through the CPAP hose to the CPAP mask to the patient;

derive the open weight pressure sensor switch (SW1) in simultaneous communication derive the closed air pressure sensor switch (SW2);

determine the open weight pressure sensor switch (SW1) on a comparison to the closed air pressure sensor switch (SW2), wherein the determination of the open weight pressure sensor switch (SW1) and the closed air pressure sensor switch (SW2) together causes the timer-output to close;

receive a sixth digital input data identifying the assigned time delay off-time of the one or more time-delay off time(s) before the patient must comply and re-occupy the patient occupancy mat after vacating the patient occupancy mat to prevent the CPAP device from powering to the off-mode;

receive the third digital input data to cause the timer of any one of the one or more timers to continue to count down to the one or more time delay off-times causing the timer-output to close;

determine the closed timer-output so that the buzzer sounds the audible alarm at the end of the one or more of the assigned time-delay off time(s) to alert the patient to occupy the patient occupancy mat;

receive the fourth digital input data to cause the timer of any one of the one or more timers to stop counting down to the one or more assigned time-delay off time(s);

transmit a fifth digital output data to the solenoid of the closed timer-output to cause the buzzer to sound the audible alarm at an end of the one or more assigned time delay off-time(s) to alert the patient to reoccupy the patient occupancy mat;

derive the fourth digital input data to cause the timer of any one of the one or more timers to stop counting down to the one or more assigned time-delay off time(s);

identify the reset feature from the compliance notification controller unit;

trigger the reset feature;

transmit the fourth digital output data to the solenoid identifying the reset feature is triggered;

determine the triggered reset feature so that the closed timer-output is open;

derive the open timer-output:

transmit the second digital output data to the solenoid of the open timer-output to cause the buzzer not to sound the audible alarm;

derive the third digital input data to cause a timer of any one of the one or more timers to start counting down to the one or more assigned time-delay off time(s);

resume the CPAP treatment for the patient;

receive the second digital input data, identifying the patient vacating the patient occupancy mat, the second digital input data including a weight pressure sensor signal (S1) at zero generated from the weight pressure sensor integrally connected within the patient occupancy mat;

derive the weight pressure sensor signal (S1), wherein deriving the weight pressure sensor signal (S1) at zero includes causing the weight pressure sensor switch (SW1) to open;

receive the second analog input data, the second analog input data identifying an air pressure within the air pressure tube removably attached to the air pressure sensor and interconnected to the CPAP hose proximate to the blower outlet of the flow generator identifying the CPAP mask detected dislodged from the patient's face;

derive the air pressure sensor signal (S2), wherein deriving the air pressure sensor signal (S2) at zero includes causing an air pressure sensor switch (SW2) to open;

determine the open weight pressure sensor switch (SW1) in simultaneous communication derive the open air pressure sensor switch (SW2);

determine the open weight pressure sensor switch (SW1) on a comparison to the open air pressure sensor switch (SW2), wherein the determination of the open weight pressure sensor switch (SW1) and the open air pressure sensor switch (SW2) together causes the timer-output to open;

derive the open weight pressure sensor switch (SW1) in simultaneous communication derive the open air pressure sensor switch (SW2);

determine the sixth digital input data identifying the assigned time delay off-time of the one or more time-delay off time(s) before the patient must comply and re-occupy the patient occupancy mat after vacating the patient occupancy mat to prevent the CPAP device from powering to the off-mode;

transmit a sixth digital output data to the solenoid to cause the CPAP device to power to the off-mode via the solenoid causing cessation of the flow generator to deliver continuous positive airway pressure channeled through the CPAP hose to the CPAP mask to the patient;

transmit the second digital output data to the solenoid of the open timer-output to cause the buzzer not to sound the audible alarm;

derive the fourth digital input data to cause the timer of any one of the one or more timers to stop counting down to the one or more assigned time-delay off time(s);

end the CPAP treatment for the patient.

18. The CPAP compliance notification system, according to claim 17, wherein the one or more microprocessors are further configured to:

receive input data and transmit output data by a mobile communication device having one or more mobile communication device microprocessors;

wherein the mobile communication device is a cell phone; and wherein the cell phone is maintained on a docking station integrally machined into the compliance notification controller unit.

19. The CPAP compliance notification apparatus, according to claim 17, wherein the compliance notification controller unit is integrally machined within a rectangular mounting platform so that the solenoid is coextensive with an exterior surface of the rectangular mounting platform, wherein the exterior surface of the rectangular mounting platform includes one or more icons implementing the CPAP treatment for the patient, wherein the one or more icons are communicable with the computer implemented programmable logic controller housed there within the rectangular mounting platform.

20. A CPAP compliance notification method, comprising one or more computer implemented programmable logic controller(s), each computer implemented programmable logic controller of the one or more computer implemented programmable logic controllers having one or more microprocessors, the one or more microprocessors on which instructions are stored, the instructions when executed by one or more actions of a user causes the one or more microprocessors together with the user to perform a CPAP compliance notification method, the CPAP compliance notification method comprising:

receiving instructions identifying components to provide a compliant continuous positive airway pressure treatment to a patient, the components including: a CPAP compliance notification apparatus for use with a CPAP device having a flow generator, a CPAP hose, a CPAP mask;
providing the CPAP device having a flow generator;
providing the CPAP hose;
providing the CPAP mask;
providing the CPAP compliance notification apparatus, the CPAP compliance and notification apparatus, comprising:
  a patient occupancy mat having a weight pressure sensor including a weight pressure sensor switch (SW1) therein for detecting a patient upon the patient occupancy mat, the weight pressure sensor operable to generate a weight pressure sensor signal (S1) triggered at the patient's occupancy of the patient occupancy mat, wherein the weight pressure sensor signal (S1) is interrupted upon the patient vacating the patient occupancy mat;
  an air pressure sensor having an air pressure sensor switch (SW2) therein, the air pressure sensor positioned within a compliance notification controller unit remotely from an airway of the patient and remotely from a blower outlet of the flow generator, the air pressure sensor operable to generate an air pressure sensor signal (S2) triggered at the patient's lodgment of the CPAP mask on the patient's face, wherein the air pressure sensor signal (S2) is interrupted upon the patient's dislodgement of the CPAP mask from the patient's face;
  an air pressure tube having an interior hollow channel limited by an open first end and an opposing open second end, the first open end communicating with the CPAP hose via a tube extender at a position proximate to the flow generator, the second open end communicating with an inlet port of the air pressure sensor;
  a solenoid including a plunger coextensive with an anterior portion of the solenoid;
  a compliance notification controller unit, including components;
  the compliance notification controller unit components, comprising:
    a housing operable to maintain compliance notification controller unit components in one location proximate to each other;
    the air pressure sensor;
    one or more ports;
    an electrical supply socket of the type suitable for receiving a universal power cord plug operable for supplying electrical power supply to the compliance notification controller unit;
    one or more DC power sources operable to direct electrical power;
    a rechargeable battery;
    a mobile communication device docking station with charger;
    a buzzer;
    the buzzer including a timer-output adapted and operable to direct an audible alarm to alert the patient during the patient's occupancy on the patient occupancy mat of interruption in air pressure at the interior hollow channel of the air pressure tube indicative that the patient has not lodged the CPAP mask within an assigned time delay off-time of the one or more assigned time delay off-time(s);
    a user interface including a touch screen including one or more text displays;
    a first text display of the one or more text displays includes an on/off text display, wherein the on/off text display being adapted and operable when pressed to direct an "on-mode" and an "off-mode" of the CPAP device via contact of the plunger against an on/off button of the CPAP device;
    a second text display of the one or more text displays includes a reset text display, wherein the reset text display being adapted and operable when pressed to direct the audible alarm of the buzzer to turn off;
    a third text display of the one or more text displays includes a snooze text display, wherein the snooze text display being adapted and operable when pressed to delay the buzzer;
    the one or more microprocessors configured to:
      receive instructions to implement the methodology of the compliant continuous positive airway pressure treatment for the patient;
      assign a time delay-off time of one or more assigned time delay-off times;
      receive input data;
      transmit output data;
      receive digital input data;
      receive analog input data;
      transmit digital output data;
    wherein digital input data includes identifying, parameters of the weight pressure sensor signal (S1), the weight pressure sensor switch (SW1), and parameters of the timer of any one of the one or more timers;
    wherein analog input data includes identifying parameters of the air pressure sensor signal (S2), the air pressure sensor switch (SW2);
    wherein digital output data includes identifying parameters of the buzzer, the solenoid, and the user interface;
  positioning the patient occupancy mat having a weight pressure sensor proximate to a supportive substrate;
  occupying the patient occupancy mat by the patient;
  lodging the patient CPAP mask so that the CPAP mask seals over the patient's nose and mouth;
  receiving a first digital input data identifying the patient detected on the patient occupancy mat, the first digital input data including the weight pressure sensor signal (S1) generated from the weight pressure sensor integrally connected within the patient occupancy mat;
  deriving the weight pressure sensor signal (S1), wherein deriving the weight pressure sensor signal (S1) includes causing the weight pressure sensor switch (SW1) to close;
  receiving a second digital input data, identifying the patient vacating the patient occupancy mat;
  the second digital input data including the weight pressure sensor signal (S1) at zero generated from the weight pressure sensor integrally connected within the patient occupancy mat;
  deriving the weight pressure sensor signal (S1), wherein deriving the weight pressure sensor signal (S1) includes causing the timer-output to close;
  deriving the timer-output being closed, wherein deriving the timer-output being closed includes causing the timer of any one of the one or more timers to start counting down to the one or more assigned time-delay off time;

deriving the weight pressure sensor signal (S1), wherein deriving the weight pressure sensor signal (S1) at zero includes causing the weight pressure sensor switch (SW1) to open;

deriving the closure of the weight pressure sensor switch (SW1);

transmitting a first digital output data to the solenoid including the closure of the weight pressure sensor switch (SW1) to cause the CPAP device to power to the on-mode via the solenoid causing the flow generator to deliver continuous positive airway pressure channeled through the CPAP hose to the CPAP mask to the patient;

receiving a third digital input data to cause the timer of any one of the one or more timers to start counting down to the one more assigned time-delay off time(s);

receiving a fourth digital input data to cause the timer of any one of the one or more timers to stop counting down to the one or assigned time-delay off time(s);

receiving a first analog input data, the first analog input data identifying an air pressure within the air pressure tube releasably attached to the air pressure sensor and interconnected to CPAP hose proximate to a blower outlet of the flow generator identifying the CPAP mask detected lodged on the patient's face;

the first analog input data including the air pressure sensor signal (S2) generated from the air pressure sensor disposed within the compliance notification controller unit;

deriving the air pressure sensor signal (S2), wherein deriving the air pressure sensor signal (S2) includes causing the air pressure sensor switch (SW2) to close;

receiving a second analog input data, the second analog input data identifying an air pressure within the air pressure tube, identifying the CPAP mask detected dislodged from the patient's face;

the second analog input data including the air pressure sensor signal (S2) generated from the air pressure sensor disposed within the compliance notification unit is interrupted;

deriving the air pressure sensor signal (S2), wherein deriving the air pressure sensor signal (S2) interrupted includes causing the air pressure sensor switch (SW2) to open;

deriving the air pressure sensor signal (S2), wherein deriving the air pressure sensor signal (S2) at zero includes causing the air pressure sensor switch (SW2) to open;

receiving a fifth digital input data identifying one or more assigned time-delay off time(s) before the patient must comply and lodge the CPAP mask sealing over his/her nose and mouth to prevent the buzzer from sounding the audible alarm;

receiving a sixth digital input data identifying an assigned delay off-time of one or more assigned time-delay off time(s) before the patient must comply and re-occupy the patient occupancy mat after vacating the patient occupancy mat to prevent the CPAP device from powering to the off-mode;

determining the closure of the weight pressure sensor switch (SW1) on a comparison to the closure of the air pressure sensor switch (SW2), wherein the determination of the closure of the weight pressure sensor switch (SW1) and the closure of the air pressure sensor switch (SW2) together causes the timer-output to open;

deriving the opening of the timer-output;

transmitting a second digital output data to the solenoid including the open timer-output to cause the buzzer not to sound the audible alarm;

receiving the second analog input data, the second analog input data identifying an air pressure within the air pressure tube, identifying the CPAP mask detected dislodged from the patient's face; the second analog input data including the air pressure sensor signal (S2) generated from the air pressure sensor disposed within the compliance notification unit is interrupted;

determining the closure of the weight pressure sensor switch (SW1) on a comparison to the open air pressure sensor switch (SW2), wherein the determination of the closure of the weight pressure sensor switch (SW1) and the opening of the air pressure sensor switch (SW2) together causes the timer-output to open;

deriving the open timer-output;

deriving the open timer-output to stop the timer of any one of the one or more timers from counting down;

transmitting a third digital output data to the solenoid of the open timer-output to cause the buzzer to sound the audible alarm at an end of the one or more assigned time-delay off time(s) to alert the patient to lodge the CPAP mask;

deriving the fourth digital input data to cause the timer of any one of the one or more timers to stop counting down to the one or more assigned time-delay off time(s);

identifying a reset feature from a compliance controller unit;

triggering the reset feature;

transmitting a fourth digital output data to the solenoid identifying the reset feature is triggered;

deriving the triggered reset feature so that the closed timer-output is open;

deriving the open timer-output is open;

transmitting the second digital output data to the solenoid of the open timer-output to cause the buzzer not to sound the audible alarm so that the buzzer is silenced;

deriving the third digital input data to cause the timer of any one of the one or more timers to start counting down to the one or more assigned time-delay off time(s);

resuming the CPAP treatment for the patient;

transmitting a fifth digital output data to the solenoid to cause the CPAP device to power to the off-mode via the solenoid causing cessation of the flow generator to deliver continuous positive airway pressure channeled through the CPAP hose to the CPAP mask to the patient;

transmitting the second digital output data to the solenoid of the open timer-output to cause the buzzer not to sound the audible alarm;

deriving the fourth digital input data to cause the timer of the one or more timers to stop counting down to the one or more assigned time-delay off time(s); and causing the compliant continuous positive airway pressure treatment to the patient to end.

21. A CPAP compliance notification method, for use with a CPAP device having a CPAP hose and a CPAP mask, the CPAP compliance notification method, comprising the steps of:

providing instructions to provide a CPAP treatment to a patient;

providing a CPAP compliance notification apparatus for use with a CPAP device having a flow generator, a CPAP hose, a CPAP mask;

providing the CPAP device having a flow generator;

providing the CPAP hose;

providing the CPAP mask;

providing the CPAP compliance notification apparatus;

the CPAP compliance notification apparatus, comprising:

a patient occupancy mat having a weight pressure sensor including a weight pressure sensor switch (SW1) therein for detecting a patient upon the patient occupancy mat, the weight pressure sensor operable to generate a weight pressure sensor signal (S1) triggered at the patient's occupancy of the patient occupancy mat, wherein the weight pressure sensor signal (S1) is interrupted upon the patient vacating the patient occupancy mat;

an air pressure sensor having an air pressure sensor switch (SW2) therein positioned, the air pressure sensor positioned remotely from an airway of the patient and remotely from a blower outlet of the flow generator, the air pressure sensor operable to generate an air pressure sensor signal (S2) triggered at the patient's lodgment of the CPAP mask on the patient's face, wherein the air pressure sensor signal (S2) is interrupted upon the patient's dislodgement of the CPAP mask from the patient's face;

an air pressure tube having an interior hollow channel limited by an open first end and an opposing open second end, the first open end communicating with the CPAP hose via an extension tubing at a position proximate to the flow generator, the second open end communicating with an inlet port of the air pressure sensor;

a solenoid including a plunger coextensive with an anterior portion of the solenoid;

a compliance notification controller unit, including components;

a housing operable to maintain the compliance notification controller unit components in one location proximate to each other;

the compliance notification controller unit components, including:

one or more ports;

an electrical supply socket of the type suitable for receiving a universal power cord plug operable for supplying electrical power supply to the compliance notification controller unit;

one or more DC power sources operable to direct electrical power;

a rechargeable battery;

a mobile communication device docking station with charger;

a buzzer;

the buzzer including a timer-output adapted and operable to direct an audible alarm to alert the patient during the patient's occupancy on the patient occupancy mat of interruption in air pressure at the hollow interior channel of the air pressure tube indicative that the patient has not lodged the CPAP mask within an assigned time delay off-time of the one or more assigned delay-off time(s);

the user interface including a touch screen including one or more text displays;

a first text display of the one or more text displays includes an on/off text display, wherein the on/off text display being adapted and operable when pressed to direct an "on-mode" and an "off-mode" of the CPAP device via contact of the plunger against an on/off button of the CPAP device;

a second text display of the one or more text displays includes a reset text display, wherein the reset text display being adapted and operable when pressed to direct an audible alarm of the buzzer to turn off;

a third text display of the one or more text displays includes a snooze text display, wherein the snooze text display being adapted and operable when pressed to delay the buzzer;

a programmable logic controller configured and adapted to implement parameters to perform a methodology of a compliant continuous positive airway pressure treatment for a patient;

the programmable logic controller, comprising:

one or more microprocessors configured to:

receive instructions to implement a method of a CPAP treatment for the patient;

assign one or more timers to one or more time delay off-times;

receive digital input data;

receive analog input data;

to transmit transmitting digital output data;

wherein digital input data includes identifying, parameters of the weight pressure sensor signal (S1), the weight pressure sensor switch (SW1), and parameters of the timer of any one of the one or more timers;

wherein analog input data includes identifying parameters of the air pressure sensor signal (S2), the air pressure sensor switch (SW2);

wherein digital output data includes identifying parameters of the buzzer, the solenoid, and the user interface;

positioning the patient occupancy mat having a weight pressure sensor proximate to a supportive substrate;

programming the time delay off-times assigned to any one of the one or more timers;

patient occupying the patient occupancy mat;

causing weight pressure sensor to generate a weight pressure sensor signal (S1);

causing the weight pressure sensor switch (SW1) to close;

causing the timer-output to close;

causing the CPAP device to power to on-mode and in simultaneous communication causing the timer of any one of the one or more timers automatically to start and countdown to one or more time delay off-time(s);

lodging the patient CPAP mask so that the CPAP mask seals over the nose and mouth within an end limit of the one or more time delay off-time(s);

causing the air pressure sensor to generate an air pressure sensor signal (S2);

causing the air pressure sensor switch (SW2) to close and in simultaneous communication causing the timer-output to open so that the buzzer does not sound the audible alarm in the event the patient manages to maintain the CPAP mask sealed during a subsequent sleep cycle;

resting through the sleep cycle duration wherein patient receives a prescribed continuous air pressure treatment for a sleep apnea;

patient waking and removing the CPAP mask and accordingly causing interruption in the air pressure sensor signal (S2);

causing the air pressure sensor switch (SW2) to open;

patient vacating the patient occupancy mat;

causing interruption in the weight pressure sensor signal (S1);

causing the weight pressure sensor switch (SW1) to open;

deriving the open weight pressure sensor switch (SW1) in simultaneous communication derive the open air pressure sensor switch (SW2);

determining the open weight pressure sensor switch (SW1) on a comparison to a closed air pressure sensor switch (SW2), wherein the determination of the open weight pressure sensor switch (SW2) and the closed air pressure sensor switch (SW2) together causes the timer-output to close;

deriving the closed timer-output so that the buzzer sounds the audible alarm at an end of the one or more of the assigned time-delay off time(s) to alert the patient to occupy the patient occupancy mat;

identifying the reset feature from a compliance controller unit;

receiving data identifying the reset feature is triggered;

deriving the triggered reset feature so that the closed timer-output is open;

deriving the open timer-output so that the buzzer is silenced and does not sound the audible alarm;

resuming the CPAP treatment for the patient;

the patient vacating the patient occupancy mat causing the weight pressure sensor switch (SW1) to close;

the patient dislodging the CPAP mask causing the air pressure sensor (SW2) to open;

deriving the determination of the open weight pressure sensor switch (SW1) and the determination of the open air pressure sensor switch (SW2) in simultaneous communication causing the CPAP device to power to the off-mode;

causing the timer of any one of the one or more timers to stop counting down to the assigned time-delay off time; and causing the CPAP treatment to the patient to end.

22. The CPAP compliance notification method, according to claim 21, further comprising the steps of:

positioning the patient occupancy mat having the weight pressure sensor proximate to the supportive substrate;

programming the time delay off-time;

patient occupying the patient occupancy mat;

causing the weight pressure sensor to generate weight pressure sensor signal (S1);

causing the weight pressure sensor switch (SW1) to close;

causing the CPAP device to power to on-mode;

causing the timer-output to close;

causing the timer of one of any of the one or more timers automatically to start and count down to one or more time delay off-time(s);

failing to lodge the patient CPAP mask onto the patient's face so that the CPAP mask does not seal over the nose and mouth within an end limit of the one or more time delay off-time (s);

causing the air pressure sensor switch (SW2) to open;

causing the buzzer to sound the audible alarm to alert the patient to lodge the CPAP mask;

pressing the reset text display;

causing the timer-output to open;

causing the buzzer to silence the audible alarm, and in simultaneous communication causing the timer of the any one of the one or more timers to restart; and resuming the CPAP treatment to the patient.

23. The CPAP compliance notification method according to claim 21, further comprising the steps:

patient waking and removing the CPAP mask and accordingly causing interruption in the air pressure sensor signal (S2);

causing the air pressure sensor switch (SW2) to open;

patient vacating the patient occupancy mat;

causing interruption in the weight pressure sensor signal (S1);

causing the weight pressure sensor switch (SW1) to open;

deriving the open weight pressure sensor switch (SW1) in simultaneous communication with the open air pressure sensor switch (SW2);

determining the open weight pressure sensor switch (SW1) on a comparison to a closed air pressure sensor switch (SW2), wherein the determination of the open weight pressure sensor switch (SW1) and the closed air pressure sensor switch (SW2) together causes the timer-output to close;

deriving the closed timer-output so that the buzzer sounds the audible alarm at an end of the one or more of the assigned time-delay off time(s) to alert the patient to occupy the patient occupancy mat;

identifying the reset feature from a compliance controller unit;

receiving data identifying the reset feature is triggered;

deriving the triggered reset feature so that the closed timer-output is open;

deriving the open timer-output so that the buzzer is silenced and does not sound the audible alarm; and resuming the CPAP treatment to the patient.

24. A CPAP compliance notification kit for use with a CPAP device having a flow generator, a CPAP hose, and a CPAP mask, the CPAP compliance notification kit comprising:

a CPAP compliance notification apparatus;

instructions for use for the CPAP compliance notification apparatus;

the compliance notification apparatus comprising:

a patient occupancy mat having a weight pressure sensor including a weight pressure sensor switch (SW1) therein for detecting a patient upon the patient occupancy mat, the weight pressure sensor operable to generate a weight pressure sensor signal (S1) triggered at the patient's occupancy of the patient occupancy mat, wherein the weight pressure sensor signal (S1) is interrupted upon the patient vacating the patient occupancy mat;

an air pressure sensor having an air pressure sensor switch (SW2) therein positioned remotely from an airway of the patient and remotely from a blower outlet of the flow generator, the air pressure sensor operable to generate an air pressure sensor signal (S2) triggered at the patient's lodgment of the CPAP mask on the patient's face, wherein the air pressure sensor signal (S2) is interrupted upon the patient's dislodgement of the CPAP mask from the patient's face;

an air pressure tube having an interior hollow channel limited by an open first end and an opposing open second end, the first open end communicating with the CPAP hose via an extension tubing at a position proximate to the flow generator, the second open end communicating with an inlet port of the air pressure sensor;

a solenoid including a plunger coextensive with an anterior portion of the solenoid;

a compliance notification controller unit;

a housing operable to maintain compliance notification controller unit components in one location proximate to each other;

the compliance notification controller unit components, comprising:

one or more ports;

an electrical supply socket of the type suitable for receiving a universal power cord plug operable for supplying electrical power supply to the compliance notification controller unit;

one or more DC power sources operable to direct electrical power;

a rechargeable battery;

a mobile communication device docking station with charger;

a buzzer;

a buzzer including a timer-output adapted and operable to direct an audible alarm to the patient to alert the patient during the patient's occupancy on the patient occupancy mat of interruption in air pressure at the interior hollow channel of the air pressure tube indicative that the patient has not lodged the CPAP mask within an assigned time delay off-time of any one of the one or more assigned time delay off-time(s);

the user interface including a touch screen including one or more text displays;

a first text display of the one or more text displays includes an on/off text display, wherein the on/off text display being adapted and operable when pressed to direct an "on-mode" and an "off-mode" of the CPAP device via contact of the plunger against an on/off button of the CPAP device;

a second text display of the one or more text displays includes a reset text display, wherein the reset text display being adapted and operable when pressed to direct the audible alarm of the buzzer to turn off;

a third text display of the one or more text displays includes a snooze text display, wherein the snooze text display being adapted and operable when pressed to delay the buzzer;

one or more programmable logic controllers configured and adapted to implement parameters to perform a methodology of a compliant continuous positive airway pressure treatment for a patient;

the programmable logic controller of the one or more programmable logic controllers, comprising:

one or more microprocessors configured to receive instructions to implement the methodology of a CPAP treatment for the patient;

one or more timers; the one or more microprocessors configured to:

receive digital input data;

receive analog input data;

transmit digital output data;

wherein digital input data includes identifying, parameters of the weight pressure sensor signal (S1), the weight pressure sensor switch (SW1), and parameters of the timer of any one of the one or more timers;

wherein analog input data includes identifying parameters of the air pressure sensor signal (S2), the air pressure sensor switch (SW2); and wherein digital output includes identifying parameters of the buzzer, the solenoid and the user interface.

* * * * *